US007880059B2

(12) United States Patent
Dixon et al.

(10) Patent No.: US 7,880,059 B2
(45) Date of Patent: Feb. 1, 2011

(54) PRODUCTION OF PROANTHOCYANIDINS TO IMPROVE FORAGE QUALITY

(75) Inventors: Richard A. Dixon, Ardmore, OK (US); Luzia V. Modolo, Castelo (ES); Gregory Peel, Ardmore, OK (US)

(73) Assignee: The Samuel Roberts Noble Foundation, Ardmore, OK (US)

( * ) Notice: Subject to any disclaimer, the term of this patent is extended or adjusted under 35 U.S.C. 154(b) by 73 days.

(21) Appl. No.: 12/108,332

(22) Filed: Apr. 23, 2008

(65) Prior Publication Data

US 2009/0083874 A1 Mar. 26, 2009

Related U.S. Application Data

(60) Provisional application No. 60/914,279, filed on Apr. 26, 2007.

(51) Int. Cl.
| A01H 5/00 | (2006.01) |
| C12N 5/14 | (2006.01) |
| C12N 15/63 | (2006.01) |
| C07H 21/04 | (2006.01) |

(52) U.S. Cl. .................. 800/295; 800/298; 435/419; 435/320.1; 536/23.1; 536/23.6
(58) Field of Classification Search ........................ None
See application file for complete search history.

(56) References Cited

U.S. PATENT DOCUMENTS

| 7,244,599 B2 | 7/2007 | Tanner et al. ............... 435/189 |
| 2004/0093632 A1 | 5/2004 | Dixon et al. ................ 800/278 |
| 2005/0278800 A1 | 12/2005 | Elton ........................... 435/6 |
| 2006/0123508 A1 | 6/2006 | Dixon et al. ................ 800/278 |

FOREIGN PATENT DOCUMENTS

| WO | WO 02/10412 | 2/2002 |
| WO | WO 02/39809 | 5/2002 |
| WO | WO 03/031622 | 4/2003 |
| WO | WO 03/040306 | 5/2003 |
| WO | WO 03/093464 | 11/2003 |
| WO | WO 2004/090136 | 10/2004 |
| WO | WO 2006/010096 | 1/2006 |
| WO | WO 2007/009181 | 1/2007 |
| WO | WO 2007/027105 | 3/2007 |

OTHER PUBLICATIONS

Yang et al. (PNAS, 98:11438-11443, 2001; abstract; pp. 11442-11443).*
McConnell et al. (Nature, 411:709-713, 2001).*
Chan et al. (Biochimica et Biophysica Acta, 1442:1-19, 1998).*
Guo et al. (PNAS, 101: 9205-9210, 2004).*
Keskin et al. (Protein Science, 13:1043-1055, 2004).*
Wells, Biochemistry 29:8509-8517, 1990.*
Lin et al. (NCBI, GenBank, Sequence Accession No. AC152405; Published Mar. 21, 2006).*
Ray et al. (Plant Physiol., 132:1448-1463; Published 2003).*
Ngo et al., (The Protein Folding Problem and Tertiary Structure Prediction, K. Merz., and S. Le Grand (eds.) pp. 492-495, 1994).*
Thornton et al. (Nature structural Biology, structural genomics supplement, Nov. 2000).*
Aharoni et al., "The strawberry FaMYB1 transcription factor suppresses anthocyanin and flavonol accumulation in transgenic tobacco," *Plant J.*, 28(3):319-332, 2001.
Aziz et al., "Trascriptome analysis of alfalfa glandular trichomes," *Planta*, 221:28-38, 2005.
Borevitz et al., "Activation tagging identifies a conserved MYB regulator of phenylpropanoid biosysnthesis," *Plant Cell*, 12:2383-2393, 2000.
de Majnik et al., "Anthocyanin regulatory gene expression in transgenic white clover can result in an altered pattern of pigmentation," *Aust. J. Plant Physiol.*, 27:659-667, 2000.
Debeaujon et al., "The Transparent Testa 12 gene of *Arabidopsis* encodes a multidrug secondary transporter-like protein required for flavonoid sequestration in vacuoles of the seed coat endothelium," *Plant Cell*, 13:853-871, 2001.
Deluc et al., "Characterization of a grapevine R2R3-MYB transcription factor that regulates the phenylpropanoid pathway$^1$," *Plant Physiology*, 140:499-511, 2006.
Dixon et al., "Tansley review—Proanthocyanidins—a final frontier in flavonoid research," *New Phytologist*, 165:9-28, 2005.
GenBank Accession No. AC135317, dated Apr. 26, 2008.
GenBank Accession No. AC152405, dated Aug. 24, 2007.
GenBank Accession No. AC172742, dated Mar. 24, 2007.
GenBank Accession No. AF325123, dated Feb. 7, 2001.
GenBank Accession No. CT573509, dated Feb. 6, 2006.
GenPept Accession No. AAG25927, dated Oct. 25, 2000.
Jackson et al., "The extractable and bound condensed tannin content of leaves from tropical tree, shrub and forage legumes," *J. Sci. Food Agric.*, 71:103-110, 1996.
Kitamura et al., "Transparent Testa 19 is involved in the accumulation of both anthocyanins and proanthocyanidins in *Arabidopsis*," *Plant J.*, 37:104-114, 2004.
Koupai-Abyazani et al., "Purification and characterization of a proanthocyanidin polymer from seed of alfalfa (*Medicago sativa*)," *J. Agric. Food Chem.*, 41:565-569, 1993.
Lees, "Condensed tannins in some forage legumes: their role in the prevention of ruminant pasture bloat," *Basic Life Sci.*, 59:915-934, 1992.

(Continued)

*Primary Examiner*—Vinod Kumar
(74) *Attorney, Agent, or Firm*—SNR Denton US LLP

(57) ABSTRACT

The invention provides method and compositions for the modulation of anthocyanin and proanthocyanidin production in plants. The methods of the invention allow creation of plants having novel phenotypes. Increased expression of anthocyanins and proanthocyanidins in plants may be used to increase the nutritional value of food plants for both human and animal consumption. Increased proanthocyanidin content also reduces the potential for bloat in animals fed certain forage plants low in condensed tannin content. The invention may also be used to modify plant pigmentation, and for nutraceutical and food colorant production.

19 Claims, 20 Drawing Sheets

OTHER PUBLICATIONS

Liu et al., "Bottlnecks for metabolic engineering of isoflavone glycoconjugates in *Arabidopsis*," *Proc. Natl. Acad. Sci. USA*, 99:14578-14583, 2002.

Mathews et al., "Activation tagging in tomato identifies a transcriptional regulator of anthocyaninbiosynthesis, modification, and transport," *Plant Cell*, 15:1689-1703, 2003.

McKhann et al., "Isolation of chalcone synthase and chalcone isomerase cDNAs from alfalfa (*Medicago sativa* L.): highest transcript levels occur in young roots and root tips," *Plant Mol. Biol*, 24(5):767-777, 1994.

Modolo et al., "A functional genomics approach to (iso)flavonoid glycosylation in the model legume *Medicago truncatula*," *Plant Mol. Biol.*, 64:499-518, 2007.

Pourcel et al., "Transparent Testa 10 encodes a laccase-like enzyme involved in oxidative polymerization of flavonoids in *Arabidopsis* seed coat," *Plant Cell*, 17:2966-2980, 2005.

Quattrocchio et al., "Molecular analysis of the anthocyanin2 gene of petunia and its role in the evolution of flower color," *Plant Cell*, 11:1433-1444, 1999.

Ray et al., "Expression of anthocyanins and proanthocyanidins after transformation of alfalfa with maize Lc[1,2]," *Plant Physiology*, 132:1448-1463, 2003.

Sharma et al., "Metabolic engineering of proanthocyanidins by ectopic expression of transcription factors in *Arabidopsis thaliana*," *Plant J.*, 44:62-75, 2005.

Skadhauge et al., "Leucocyanidin reductase activity and accumulation of proanthocyanidins in developing legume tissues," *American J. of Bot.*, 84:494, Abstract, 1997.

Tanner et al., "Proanthocyanidin biosynthesis in plants: purification of legume leucoanthocyanidin reductase and molecular cloning of its cDNA," *J. Biol. Chem.*, 278:31647-31656, 2003.

TIGR Clone TC105632, undated.

Tohge et al., "Functional genomics by integrated analysis of metabolome and transcriptome of *Arabidopsis* plants overexpressing a MYB transcription factor," *Plant J.*, 42:218-235, 2005.

Xie et al., "Metabolic engineering of proanthocyanidins through co-expression of anthocyanidin reductase and the PAP1 MYB transcription factor," *Plant J.*, 45:895-907, 2006.

Xie et al., "Proanthocyanidin biosynthesis—still more questions than answers," *Phytochemistry*, 66:2126-2143, 2005.

Xie et al., "Role of anthocyanidin reductase, encoded by Banyuls in plant flavonoid biosynthesis," *Science*, 299:396-399, 2003.

Robbins et al., "Sn, a maize bHLH gene, modulates anthocyanin and condensed tannin pathways in *Lotus corniculatus*," *J. of Exper. Bot.*, 54(381):239-248, 2003.

* cited by examiner

SEQUENCE LISTING

```
<160> NUMBER OF SEQ ID NOS: 98

<210> SEQ ID NO 1
<211> LENGTH: 735
<212> TYPE: DNA
<213> ORGANISM: Medicago truncatula

<400> SEQUENCE: 1
atggagaata   ccggaggtgt   gagaaaaggc   gcatggactt   acaaggaaga   tgagctactc      60
aaggcttgca   ttaacacgta   cggtgaagga   aaatggaatt   tagttcctca   gagatctgga     120
ttgaatagat   gcagaaaaag   ttgtagattg   aggtggttaa   attacttaag   ccccaacatc     180
aacagaggaa   gattttctga   ggatgaagaa   gatttgatcc   taaggttaca   caaactacta     240
ggaaatagat   ggtcattgat   tgctggaagg   cttccgggta   gaacagctaa   tgatgtgaag     300
aactattggc   acacaaattt   ggcaaagaaa   gtggtttcag   aaaaggaaga   agagaaagaa     360
aacgataaac   ctaaggaaac   catgaaagct   catgaagtta   ttaaacctcg   tcctataact     420
```

```
ttgtcaagtc attcaaattg gttgaagggg aaaaatagta ttcctagaga tcttgattac    480
tcagagaata tggcttcaaa tcaaattggt agagagtgtg cttctacttc aaaaccagat    540
ctaggtaatg ccccaatacc atgtgaaatg tggtgtgaca gtttgtggaa cttgggagaa    600
catgtagaca gtgagaaaat tgggtcatgc tcttcattac aagaggagaa cttaatggag    660
tttccaaatg ttgatgatga ctccttttgg gatttcaacc tttgtgattt gaattctctt    720
tgggatctac cttga                                                     735

<210> SEQ ID NO 2
<211> LENGTH: 765
<212> TYPE: DNA
<213> ORGANISM: Medicago truncatula

<400> SEQUENCE: 2
atggagatga ccagaggcgt gagaaaaggt gcatggacat atgaggaaga caagctactc     60
aaggcttgta tacagaagta tggtgaagga aaatggcatt tagttccaca agagcagga    120 ttgataggt gccgaaaaag ctgtagattg aggtggttaa attatttaac ccccaacatc    180 aaagggaaa gctttgctga ggatgaagtt gatatgatgc taaggttaca caacttcta    240 ggaatagat ggtcattgat tgctgcaagg cttccgggta aacagctaa tgatgtgaag    300 aattattggc acacacattt gagaagaag atggtttcaa gaacactaga gaaaagaaa    360 gaaaaaccta ggaaaccat gaaagttcat gaaattatta acctaaaacc tcgaactttc    420
tcaactcatc caccttcgtt gaactggaaa cataatatta atgtgacacc aattgtggcg    480
gtttcaactc aacacggtga agtctcgcca atcgtgata taaagagat tacggattca    540 aaccaaattg gtagagatat tgttggtgtt tcccaaccaa gtcttggtag tgctccaata    600
ccgtgtgcaa tgttgtggga cagtttattg aacttggagg agcataaaag tagtgagaaa    660
attgggtcag gctcttttatt acaagaggag aacttcattt ctgagtttcc aaatgtggat    720
gactcctttt gggattttcaa cctttgtgat ttcgattctc tttga                   765

<210> SEQ ID NO 3
<211> LENGTH: 774
<212> TYPE: DNA
<213> ORGANISM: Medicago truncatula

<400> SEQUENCE: 3
atggataata ccataggcgt gaaaaaaggt gcatggacat acgaggaaga caacttactc     60
aaggcttaca ttaacaagta tggtgaagga aaatggcatt taattcctca agagcaggt    120 tcaggattga atagatgtcg aaaagttgt agattgaggg gataaatta tttaaagccc    180 aacatcaata gaaaaagctt ttctgaggat gaagttgata tgatcctaag gttacacaaa    240
ctcttaggaa atagatggtc attgattgct ggaaggcttc cgggtagaac agctaatagt    300
gtgaaaaact attggaacac acacttgttg aagaaggtgg tttcaaaaca gaagaagaa    360 aaagagaaac caatggagac aatgaaagct caccaagtta ttaaacctag acctataact    420
ttttcaactc aatcatcttg gttgaatgtg aaacacaata attttgtgac acaaccatta    480
ttggcttcaa acaatgatgg ttgttttcct agagatcgtg atgacaaaat gactatggtt    540
gttcctaacc aaaattggta aagattgtgct tcttcttcac aaccaattct aggtaatgtc    600
ccaatacctt gtacaatgtg gtcagaaagt ttatggaact tggggagca agtgatagt    660 gagataattg gatcgtcctc ttcattacaa gtggagaact atgaggagtt ttcaattgtt    720
```

-continued

```
gatgactttt gggatttcaa catttgtgat tatgattctc tttgggatct ttag      774
```

<210> SEQ ID NO 4
<211> LENGTH: 795
<212> TYPE: DNA
<213> ORGANISM: Medicago truncatula

<400> SEQUENCE: 4

```
atggagaagt gtaagactag aggtgtgaga aaggtgcat ggacatatga ggaagacaag      60
ctactcaagg cttgtatgca gaagtatggt gaaggaaaat ggcatttagt tccacaaaga    120
gcaggattga ataggtgccg gaaaagttgt agattgaggt ggttaaatta tttaaacccc    180
accatcaata gagagagttt ttctgaggat gaagttgata tgattttaag gttacacaag    240
cttttaggga acagatggtc attgattgct gcaagactcc cgggtagaac agctaatgat    300
gtgaagaatt attggcacac acatttacgc aagaagatgg tttcaagaaa agaagaaaag    360
aaagaaaatg agaaacctaa agaaagcatg caaactcatg aagttattaa acctcaacct    420
cgaactttt catctcattc accatggttg aatgggaaat ataataattt tgtgacacca    480
atagtaactg tttcaacaaa tgatggtaat gttgcaaaag atagtgaagt agatactatt    540
ctaccaatta atggtgatgg tgatagtgct gcacaaccat atcttgaaaa tccaacactg    600
tcttccatgt ggtgggagag tttgttgaac gtgagcaatg acaaaattgg atcatgctct    660
ttactattac cagaggaata ttccaaatta aatgttgaga cttttcttgc tgaaggaccc    720
agtactgtcg gtgatttctc ctgggattct accatttgtg aatttgactc tcttttagat    780
gatatcttaa attag                                                      795
```

<210> SEQ ID NO 5
<211> LENGTH: 243
<212> TYPE: PRT
<213> ORGANISM: Medicago truncatula

<400> SEQUENCE: 5

```
Met Glu Asn Thr Gly Gly Val Arg Lys Gly Ala Trp Thr Tyr Lys Glu
1               5                   10                  15

Asp Glu Leu Leu Lys Ala Cys Ile Asn Thr Tyr Gly Glu Gly Lys Trp
            20                  25                  30

Asn Leu Val Pro Gln Arg Ser Gly Leu Asn Arg Cys Arg Lys Ser Cys
        35                  40                  45

Arg Leu Arg Trp Leu Asn Tyr Leu Ser Pro Asn Ile Asn Arg Gly Arg
    50                  55                  60

Phe Ser Glu Asp Glu Asp Leu Ile Leu Arg Leu His Lys Leu Leu
65                  70                  75                  80

Gly Asn Arg Trp Ser Leu Ile Ala Gly Arg Leu Pro Gly Arg Thr Ala
                85                  90                  95

Asn Asp Val Lys Asn Tyr Trp His Thr Asn Leu Ala Lys Lys Val Val
            100                 105                 110

Ser Glu Lys Glu Glu Lys Glu Asn Asp Lys Pro Lys Glu Thr Met
        115                 120                 125

Lys Ala His Glu Val Ile Lys Pro Arg Pro Ile Thr Leu Ser Ser His
    130                 135                 140

Ser Asn Trp Leu Lys Gly Lys Asn Ser Ile Pro Arg Asp Leu Asp Tyr
145                 150                 155                 160

Ser Glu Asn Met Ala Ser Asn Gln Ile Gly Arg Glu Cys Ala Ser Thr
                165                 170                 175
```

```
Ser Lys Pro Asp Leu Gly Asn Ala Pro Ile Pro Cys Glu Met Trp Cys
            180                 185                 190

Asp Ser Leu Trp Asn Leu Gly Glu His Val Asp Ser Glu Lys Ile Gly
        195                 200                 205

Ser Cys Ser Ser Leu Gln Glu Glu Leu Met Glu Phe Pro Asn Val Asp
    210                 215                 220

Asp Asp Ser Phe Trp Asp Phe Asn Leu Cys Asp Leu Asn Ser Leu Trp
225                 230                 235                 240

Asp Leu Pro

<210> SEQ ID NO 6
<211> LENGTH: 254
<212> TYPE: PRT
<213> ORGANISM: Medicago truncatula

<400> SEQUENCE: 6

Met Glu Met Thr Arg Gly Val Arg Lys Gly Ala Trp Thr Tyr Glu Glu
1               5                   10                  15

Asp Lys Leu Leu Lys Ala Cys Ile Gln Lys Tyr Gly Glu Gly Lys Trp
            20                  25                  30

His Leu Val Pro Gln Arg Ala Gly Leu Asn Arg Cys Arg Lys Ser Cys
        35                  40                  45

Arg Leu Arg Trp Leu Asn Tyr Leu Thr Pro Asn Ile Lys Arg Glu Ser
    50                  55                  60

Phe Ala Glu Asp Glu Val Asp Met Met Leu Arg Leu His Lys Leu Leu
65                  70                  75                  80

Gly Asn Arg Trp Ser Leu Ile Ala Ala Arg Leu Pro Gly Arg Thr Ala
                85                  90                  95

Asn Asp Val Lys Asn Tyr Trp His Thr His Leu Arg Lys Lys Met Val
            100                 105                 110

Ser Arg Thr Leu Glu Glu Lys Lys Glu Lys Pro Lys Glu Thr Met Lys
        115                 120                 125

Val His Glu Ile Ile Lys Pro Lys Pro Arg Thr Phe Ser Thr His Pro
    130                 135                 140

Pro Ser Leu Asn Trp Lys His Asn Ile Asn Val Thr Pro Ile Val Ala
145                 150                 155                 160

Val Ser Thr Gln His Gly Glu Val Ser Pro Asn Arg Asp Asn Lys Glu
                165                 170                 175

Ile Thr Asp Ser Asn Gln Ile Gly Arg Asp Ile Val Gly Val Ser Gln
            180                 185                 190

Pro Ser Leu Gly Ser Ala Pro Ile Pro Cys Ala Met Leu Trp Asp Ser
        195                 200                 205

Leu Leu Asn Leu Glu Glu His Lys Ser Ser Glu Lys Ile Gly Ser Gly
    210                 215                 220

Ser Leu Leu Gln Glu Glu Asn Phe Ile Ser Glu Phe Pro Asn Val Asp
225                 230                 235                 240

Asp Ser Phe Trp Asp Phe Asn Leu Cys Asp Phe Asp Ser Leu
                245                 250

<210> SEQ ID NO 7
<211> LENGTH: 257
<212> TYPE: PRT
<213> ORGANISM: Medicago truncatula

<400> SEQUENCE: 7

Met Asp Asn Thr Ile Gly Val Lys Lys Gly Ala Trp Thr Tyr Glu Glu
```

```
                1               5                   10                  15
Asp Asn Leu Leu Lys Ala Tyr Ile Asn Lys Tyr Gly Glu Gly Lys Trp
                    20                  25                  30

His Leu Ile Pro Gln Arg Ala Gly Ser Gly Leu Asn Arg Cys Arg Lys
                    35                  40                  45

Ser Cys Arg Leu Arg Trp Ile Asn Tyr Leu Lys Pro Asn Ile Asn Arg
    50                  55                  60

Lys Ser Phe Ser Glu Asp Glu Val Asp Met Ile Leu Arg Leu His Lys
65                      70                  75                  80

Leu Leu Gly Asn Arg Trp Ser Leu Ile Ala Gly Arg Leu Pro Gly Arg
                    85                  90                  95

Thr Ala Asn Ser Val Lys Asn Tyr Trp Asn Thr His Leu Leu Lys Lys
                    100                 105                 110

Val Val Ser Lys Gln Glu Glu Lys Glu Lys Pro Met Glu Thr Met
                    115                 120                 125

Lys Ala His Gln Val Ile Lys Pro Arg Pro Ile Thr Phe Ser Thr Gln
                    130                 135                 140

Ser Ser Trp Leu Asn Val Lys His Asn Asn Phe Val Thr Gln Pro Leu
145                     150                 155                 160

Leu Ala Ser Asn Asn Asp Gly Cys Phe Pro Arg Asp Arg Asp Asp Lys
                    165                 170                 175

Met Thr Met Val Val Pro Asn Gln Ile Gly Lys Asp Cys Ala Ser Ser
                    180                 185                 190

Ser Gln Pro Ile Leu Gly Asn Val Pro Ile Pro Cys Thr Met Trp Ser
                    195                 200                 205

Glu Ser Leu Trp Asn Leu Gly Glu Gln Val Asp Ser Glu Ile Ile Gly
                    210                 215                 220

Ser Ser Ser Ser Leu Gln Val Glu Asn Tyr Glu Glu Phe Ser Ile Val
225                     230                 235                 240

Asp Asp Phe Trp Asp Phe Asn Ile Cys Asp Tyr Asp Ser Leu Trp Asp
                    245                 250                 255

Leu

<210> SEQ ID NO 8
<211> LENGTH: 264
<212> TYPE: PRT
<213> ORGANISM: Medicago truncatula

<400> SEQUENCE: 8

Met Glu Lys Cys Lys Thr Arg Gly Val Arg Lys Gly Ala Trp Thr Tyr
1               5                   10                  15

Glu Glu Asp Lys Leu Leu Lys Ala Cys Met Gln Lys Tyr Gly Glu Gly
                    20                  25                  30

Lys Trp His Leu Val Pro Gln Arg Ala Gly Leu Asn Arg Cys Arg Lys
                    35                  40                  45

Ser Cys Arg Leu Arg Trp Leu Asn Tyr Leu Asn Pro Thr Ile Asn Arg
    50                  55                  60

Glu Ser Phe Ser Glu Asp Val Asp Met Ile Leu Arg Leu His Lys
65                      70                  75                  80

Leu Leu Gly Asn Arg Trp Ser Leu Ile Ala Ala Arg Leu Pro Gly Arg
                    85                  90                  95

Thr Ala Asn Asp Val Lys Asn Tyr Trp His Thr His Leu Arg Lys Lys
                    100                 105                 110

Met Val Ser Arg Lys Glu Glu Lys Lys Glu Asn Glu Lys Pro Lys Glu
```

-continued

```
                115                 120                 125
Ser Met Gln Thr His Glu Val Ile Lys Pro Gln Pro Arg Thr Phe Ser
        130                 135                 140

Ser His Ser Pro Trp Leu Asn Gly Lys Tyr Asn Asn Phe Val Thr Pro
145                 150                 155                 160

Ile Val Thr Val Ser Thr Asn Asp Gly Asn Val Ala Lys Asp Ser Glu
                165                 170                 175

Val Asp Thr Ile Leu Pro Ile Asn Gly Asp Gly Asp Ser Ala Ala Gln
            180                 185                 190

Pro Tyr Leu Glu Asn Pro Thr Leu Ser Ser Met Trp Trp Glu Ser Leu
        195                 200                 205

Leu Asn Val Ser Asn Asp Lys Ile Gly Ser Cys Ser Leu Leu Leu Pro
210                 215                 220

Glu Glu Tyr Ser Lys Leu Asn Val Glu Asn Phe Leu Ala Glu Gly Pro
225                 230                 235                 240

Ser Thr Val Gly Asp Phe Ser Trp Asp Ser Thr Ile Cys Glu Phe Asp
                245                 250                 255

Ser Leu Leu Asp Asp Ile Leu Asn
        260
```

<210> SEQ ID NO 9
<211> LENGTH: 1365
<212> TYPE: DNA
<213> ORGANISM: Artificial
<220> FEATURE:
<223> OTHER INFORMATION: Artificial primer

<400> SEQUENCE: 9

```
atgtctacct tcaaaaatga atgaatggt aacaacttat tacatgtggc tgttttggca    60
ttcccatttg gcacacatgc tgctccactc cttagcctag tgaaaaaat tgctacagag    120
gctcctaaag ttcatttttc attcttctgc acaaccacaa caaatgatac tttattttct   180
aggtcaaacg agtttcttcc aaacataaag tattataatg ttcatgatgg gttaccaaaa   240
ggttacgtat cttctgggaa tccacgtgaa ccaattttc tcttcattaa ggccatgcaa    300
gagaacttta gcatgttat tgatgaagct gtggcagaga cagggaagaa cattacttgt    360
ttggttactg atgcattttt ttggtttggt gcggatttag ctgaggaaat gcatgccaaa   420
tgggttcctc tttggactgc aggacctcac tctcttctta cacatgttta cacagatctt   480
atcagagaaa agactggctc caaggaagtc catgatgtca aaagtatcga tgttcttcct   540
ggttttcccg agctaaaggc ttctgatttg cctgagggag taataaaaga tatagatgta   600
ccatttgcaa caatgttaca caaaatggga ctagagttac cacgagcgaa tgcagttgcc   660
ataaactcat tgctacaat acaccctctt attgagaatg agttaaattc aaagttcaaa    720
ttgctactaa atgttggtcc attcaacttg acaacaccac agcgtaaggt tccgatgaa    780
catggatgct agaatggtt ggaccaacat gagaattctt cagtagtgta tataagcttt    840
ggaagtgtgg taacacccc acctcatgag ctcactgcat tggcagagtc cttagaggaa    900
tgtggatttc catttatttg gtcctttagg ggtgatccta aggaaaatt gccaaaggg    960
ttcttggaaa ggacaaaaac aaaaggtaaa atcgttgcat gggctcctca agttgaaatc   1020
cttaaacatt catcggttgg tgtgttttg acgcattctg ggtggaattc tgtgttgaa    1080
tgcattgttg gtggtgtgcc aatgattagt agaccttttt ttggagatca agggttgaat   1140
acaatactta cagaaagtgt tttggagatt ggtgtgggtg ttgacaatgg agttttgact   1200
```

```
aaagaatcga ttaagaaagc tttggaatta accatgtcaa gtgagaaagg aggaataatg    1260
cgccagaaga ttgtgaaact caaggagtca gcattcaaag ctgttgaaca aaatggtacc    1320
tctgcaatgg atttcactac tttgatacaa attgtcacta gttga                    1365
```

<210> SEQ ID NO 10
<211> LENGTH: 454
<212> TYPE: PRT
<213> ORGANISM: Artificial
<220> FEATURE:
<223> OTHER INFORMATION: Artificial peptide

<400> SEQUENCE: 10

```
Met Ser Thr Phe Lys Asn Glu Met Asn Gly Asn Asn Leu Leu His Val
1               5                   10                  15

Ala Val Leu Ala Phe Pro Phe Gly Thr His Ala Ala Pro Leu Leu Ser
            20                  25                  30

Leu Val Lys Lys Ile Ala Thr Glu Ala Pro Lys Val Thr Phe Ser Phe
        35                  40                  45

Phe Cys Thr Thr Thr Thr Asn Asp Thr Leu Phe Ser Arg Ser Asn Glu
    50                  55                  60

Phe Leu Pro Asn Ile Lys Tyr Tyr Asn Val His Asp Gly Leu Pro Lys
65                  70                  75                  80

Gly Tyr Val Ser Ser Gly Asn Pro Arg Glu Pro Ile Phe Leu Phe Ile
                85                  90                  95

Lys Ala Met Gln Glu Asn Phe Lys His Val Ile Asp Glu Ala Val Ala
            100                 105                 110

Glu Thr Gly Lys Asn Ile Thr Cys Leu Val Thr Asp Ala Phe Phe Trp
        115                 120                 125

Phe Gly Ala Asp Leu Ala Glu Glu Met His Ala Lys Trp Val Pro Leu
    130                 135                 140

Trp Thr Ala Gly Pro His Ser Leu Leu Thr His Val Tyr Thr Asp Leu
145                 150                 155                 160

Ile Arg Glu Lys Thr Gly Ser Lys Glu Val His Asp Val Lys Ser Ile
                165                 170                 175

Asp Val Leu Pro Gly Phe Pro Glu Leu Lys Ala Ser Asp Leu Pro Glu
            180                 185                 190

Gly Val Ile Lys Asp Ile Asp Val Pro Phe Ala Thr Met Leu His Lys
        195                 200                 205

Met Gly Leu Glu Leu Pro Arg Ala Asn Ala Val Ala Ile Asn Ser Phe
    210                 215                 220

Ala Thr Ile His Pro Leu Ile Glu Asn Glu Leu Asn Ser Lys Phe Lys
225                 230                 235                 240

Leu Leu Leu Asn Val Gly Pro Phe Asn Leu Thr Thr Pro Gln Arg Lys
                245                 250                 255

Val Ser Asp Glu His Gly Cys Leu Glu Trp Leu Asp Gln His Glu Asn
            260                 265                 270

Ser Ser Val Val Tyr Ile Ser Phe Gly Ser Val Val Thr Pro Pro Pro
        275                 280                 285

His Glu Leu Thr Ala Leu Ala Glu Ser Leu Glu Glu Cys Gly Phe Pro
    290                 295                 300

Phe Ile Trp Ser Phe Arg Gly Asp Pro Lys Glu Lys Leu Pro Lys Gly
305                 310                 315                 320

Phe Leu Glu Arg Thr Lys Thr Lys Gly Lys Ile Val Ala Trp Ala Pro
                325                 330                 335
```

```
Gln Val Glu Ile Leu Lys His Ser Ser Val Gly Val Phe Leu Thr His
                340                 345                 350
Ser Gly Trp Asn Ser Val Leu Glu Cys Ile Val Gly Val Pro Met
            355                 360                 365
Ile Ser Arg Pro Phe Phe Gly Asp Gln Gly Leu Asn Thr Ile Leu Thr
        370                 375                 380
Glu Ser Val Leu Glu Ile Gly Val Gly Val Asp Asn Gly Val Leu Thr
385                 390                 395                 400
Lys Glu Ser Ile Lys Lys Ala Leu Glu Leu Thr Met Ser Ser Glu Lys
                405                 410                 415
Gly Gly Ile Met Arg Gln Lys Ile Val Lys Leu Lys Glu Ser Ala Phe
                420                 425                 430
Lys Ala Val Glu Gln Asn Gly Thr Ser Ala Met Asp Phe Thr Thr Leu
                435                 440                 445
Ile Gln Ile Val Thr Ser
    450

<210> SEQ ID NO 11
<211> LENGTH: 1331
<212> TYPE: DNA
<213> ORGANISM: Medicago truncatula

<400> SEQUENCE: 11
gccaaccaaa atcactagag aaaaaaaaat cagggaaaaa acagagaaaa taaatatgg        60 gttctatggc cgaaactgtt tgtgtcacag gggcttcagg ttttatcggg tcatggcttg     120
tcatgagact tatggagcgc ggttacatgg ttcgagcaac agtccgcgac ccagaaaact     180
tgaagaaggt gagtcatttg ttagaactgc caggtgcaaa gggcaaactg tccctatgga     240
aggctgacct tggtgaagag ggtagttttg atgaagctat taagggtgt acaggagttt      300 ttcatgttgc tactcctatg gattttgagt ccaaggaccc tgagaatgaa atgatcaagc     360
ctaccataaa aggggtgcta gacatcatga aagcatgcct caaggccaaa actgtccgta     420
gatttatttt cacatcatcg gccggaaccc taaacgttac tgaagatcaa aagcccttgt     480
gggatgaaag ctgttggagt gatgttgagt tttgtaggag agtgaagatg actggctgga     540
tgtattttgt ttcaaagaca cttgcggagc aagaagcatg gaaatttgcc aaagagcaca     600
acatggattt catcacaatc atcccacctc ttgttgttgg tccttttctt attcctacca     660
tgccacctag cctaatcact gcccttctc ctatcactgg aaatgaagct cattattcga     720
ttataaagca aggccaattc gtccacttgg atgatctttg tgaagctcac atattcttgt     780
ttgagcatat ggaagtagaa gggaggtatc tatgtagtgc atgtgaagct aatattcatg     840
acattgcaaa attaattaat acaaaatatc cagagtacaa tatccccaca aagttcaata     900
atattccaga tgaattggag cttgtgagat tttcatcaaa gaagatcaaa gacttgggat     960
tcgagtttaa atacagcttg gaggatatgt acactgaagc aattgataca tgcatagaaa    1020
aagggcttct tcctaaattt gttaaaagca ccaataagta atggtgtcac acataaataa    1080
ataagtatag ctatgtgtc tttatgtgtg tttctgtgat ggcttaggga tcttacttaa     1140
ttccttgaga ttttctttag tagctggaat gtttgtgcaa tcctgttgaa gcccaaactt    1200
acttgaatgt tttctatctc tttcattgt tccttattga gagctacacg aaaaaggaaa     1260
agataatgaa ttattgaata ttatttattt gcaaaatgtt gaaagcttaa aaaaaaaaa     1320 aaaaaaaaaa a                                                         1331
```

<210> SEQ ID NO 12
<211> LENGTH: 1248
<212> TYPE: DNA
<213> ORGANISM: Medicago truncatula

<400> SEQUENCE: 12

| | | | | | |
|---|---|---|---|---|---|
| gcgcccatgg | gttcagtctc | agaaacagtt | tgcgtcacag | gggcttcagg | tttcatcggg | 60 |
| tcgtggcttg | ttatgagact | tatggagcgc | ggctacacag | ttcgagccac | cgtgcgcgac | 120 |
| ccagataaca | tgaagaaggt | gaagcatttg | ttggaactgc | aggtgcaaa | tagcaaacta | 180 |
| tctctttgga | aggctgacct | tggggaagag | ggtagttttg | atgaagctat | taaagggtgt | 240 |
| acaggagttt | ttcatgttgc | tactcctatg | gattttgagt | ccaaggaccc | cgagaaggaa | 300 |
| gtgataaacc | ctacaataaa | tggattacta | gacataatga | aagcatgtaa | gaaggcaaaa | 360 |
| acagttagaa | gattggtttt | cacatcatca | gctggaactt | tggatgttac | tgagcaacaa | 420 |
| aattctgtaa | ttgatgaaac | ttgctggagt | gacgtcgaat | tctgccgtag | agtcaagatg | 480 |
| actggttgga | tgtattttgt | ttcaaaaacc | ctggcagaac | aagaagcatg | gaagttttcc | 540 |
| aaagaacaca | acatagactt | tgtttccatt | attccacctc | ttgttgttgg | tccatttatt | 600 |
| atgccttcaa | tgccaccgag | tctaatcact | gctctttccc | ttatcacagg | atatgaggct | 660 |
| cattactcga | tcataaagca | aggccaatac | atccacttag | acgacctttg | tcttgctcat | 720 |
| atatttctgt | ttgagaaccc | taaagcacat | gggagataca | tatgttgttc | acatgaggca | 780 |
| accattcatg | aagttgcaaa | acttattaac | aaaaaatacc | ctgagttcaa | tgtccctaca | 840 |
| aaattcaagg | atatcccaga | tgatctggaa | attatcaaat | tttcttcaaa | gaagatcaca | 900 |
| gacttggggt | ttatatttaa | atacagctta | gaagacatgt | tcacaggagc | tatagaaacc | 960 |
| tgcagagaaa | aagggctact | tcctaaagtt | acagagactc | cggttaatga | taccatgaag | 1020 |
| aaataaatat | gcttttgtgt | ctttgatgga | ttgtgtctct | ttttccttt | tcatttgtgt | 1080 |
| ttttttttt | aaggatcctt | tttcatatgt | tattaactaa | ggtttatgtt | atatgatgtc | 1140 |
| actcataata | atattcatgt | ttatgggtca | cgttgtctgt | taattatata | agaactataa | 1200 |
| tgatatatgc | tatattgctt | ctaaatttac | aaaaaaaaaa | aaaaaaaa | | 1248 |

<210> SEQ ID NO 13
<211> LENGTH: 27
<212> TYPE: DNA
<213> ORGANISM: Artificial
<220> FEATURE:
<223> OTHER INFORMATION: Artificial primer

<400> SEQUENCE: 13
gggcccatgg accagactct tacacac   27

<210> SEQ ID NO 14
<211> LENGTH: 950
<212> TYPE: DNA
<213> ORGANISM: Medicago sativa

<400> SEQUENCE: 14

| | | | | | |
|---|---|---|---|---|---|
| gaattcccat | agctaaacaa | aaaaaattaa | gaacaagaat | atggctgcat | caatcaccgc | 60 |
| aatcactgtg | gagaaccttg | aatacccagc | ggtggttacc | tctccggtca | ccggcaaatc | 120 |
| atatttcctc | ggtggcgctg | gggagagagg | attgaccatt | gaaggaaact | tcatcaagtt | 180 |
| cactgccata | ggtgtttatt | tggaagatat | agcagtggct | tcactagctg | ccaaatggaa | 240 |
| gggtaaatca | tctgaagagt | tacttgagac | ccttgacttt | tacagagaca | tcatctcagg | 300 |

```
tcccctttgaa aagttaatta gagggtcaaa gattagggaa ttgagtggtc ctgagtactc    360
aaggaaggtt atggagaact gtgtggcaca cttgaaatca gttggaactt atggagatgc    420
agaagctgaa gctatgcaaa aatttgctga agctttcaag cctgttaatt ttccacctgg    480
tgcctctgtt ttctacaggc aatcacctga tggaatatta gggcttagtt tctctccgga    540
tacaagtata ccagaaaagg aggctgcact catagagaac aaggcagttt catcagcagt    600
gttggagact atgatcggcg agcacgctgt tcccctgat cttaagcgct gtttagctgc     660
aagattacct gcgttgttga acgagggtgc tttcaagatt ggaaactgat gatgattata    720
ctcctatatc actgcatttc caaaagcgtt gcagcacaag aatgagacca tgaacttttt    780
taagtctaca cgtttaatttt tttgtatatc tatttacctt cttattagta tcaataatat   840
gaaatgaaag atcttgcttt ctactcttgt actatttctg tgatagataa tgttaatgag    900
tatcttcatc aataaaagtg atttgttttg tttgttcaaa aaaaaaaaa                 950

<210> SEQ ID NO 15
<211> LENGTH: 836
<212> TYPE: DNA
<213> ORGANISM: Medicago sativa

<400> SEQUENCE: 15
caaatcatat ttcctcggtg gcgctgggga gagaggattg accattgaag gaaacttcat     60
caagttcact gccataggtg tttatttgga agatatagca gtggcttcac tagctgccaa    120
atggaagggt aaatcatctg aagagttact tgagacccctt gacttttaca gagacatcat   180
ctcaggtccc tttgaaaagt taattagagg gtcaaagatt agggaattga gtggtcctga    240
gtactcaagg aaggttatgg agaactgtgt ggcacacttg aaatcagttg gaacttatgg    300
agatgcagaa gctgaagcta tgcaaaaatt tgctgaagct ttcaagcctg ttaatttccc    360
acctggtgcc tctgttttct acaggcaatc acctgatgga atattagggc ttagtttctc    420
tccggataca agtataccag aaaaggaggc tgcactcata gagaacaagg cagtttcatc    480
agcagtgttg gagactatga tcggcgaaca cgctgtttcc cctgatctta agcgctgttt    540
ggctgcaaga ttacctgcgt tgttgaacga gggtgctttc aagattggaa actgatgatg    600
attatactct tatataaaaa catttccaaa agcgttgcag cacaagaatg agaccatgga    660 ctttttttaag tctacacgtt taatttttg tatatctatt taccttctta ttagtatcaa    720
tagtatgaaa tgaaagatct tgctttctac tcttgtacta tttctgtgat agataatgtt    780
aatgagtatc ttcatcaata aaagtgattt gttttgtttg ttcaaaaaaa aaaaaa        836

<210> SEQ ID NO 16
<211> LENGTH: 1380
<212> TYPE: DNA
<213> ORGANISM: Medicago sativa

<400> SEQUENCE: 16
gaattcccaa caaacaagta ctgcaaacca attgagtatt acatagaaac tactagagat     60
accaagatgg tgagtgtatc tgaaattcgc aaggctcaga gggcagaagg tcctgcaacc    120
attttggcca ttggcactgc aaatccagca aattgtgttg aacaaagtac atatcctgat    180
ttttacttta aaatcacaaa tagcgagcac aagactgaac tcaaagagaa attccaacgc    240
atgtgtgata aatctatgat caagaggaga tacatgtacc taacagagga gattttgaaa    300
gagaatccta gtgtttgtga atatatgcca ccttcattgg atgccaggca agacatggtg    360
gtggtagagg tacctagact agggaaggag gctgcagtga aggctataaa agaatggggt    420
```

```
caaccaaagt caaagattac tcacttaatt gtttgcacta caagtggtgt agacatgcct    480
ggagctgatt accaactcac aaaactcttg gtcttcgcc  catatgtgaa aaggtatatg    540
atgtaccaac aaggttgctt tgcaggaggc acggtgcttc gtttggctaa agatttggct    600
gagaacaaca aaggtgcccg tgtattggtt gtttgttctg aagtcactgc agtcacattc    660
cgcggcccta gtgatactca cttggacagc cttgttggac aagcactatt tggagacgga    720
gctgctgcac taattgttgg ttctgatcca gtaccagaaa ttgagaaacc tatatttgag    780
atggtttgga ctgcacaaac aattgctcca gatagtgaag gagccattga tggtcacctt    840
cgtgaagctg gactaacatt ccaccttctt aaagatgttc ctgggattgt ttcaaagaac    900
attgataaag cattagttga agctttccaa ccattgggaa tttctgatta caactcaatc    960 tttggattg  cacaccctgg tggccctgca attttagatc aagtagagca aaagttagcc    1020
ttgaagcctg aaaagatgag agccactaga gaagtgctta gtgaatatgg aaatatgtca    1080
agtgcatgtg ttttgtttat cttagatgaa atgagaaaga aatcaactca agatggactg    1140
aagacaacag gagaaggact tgaatggggt gtgttatttg ctttggacc  aggacttacc    1200 atagaaactg ttgttttgcg cagtgtcgct atatgaaatg cttaattatt ttattttat    1260 ttatcacttt caaatttgct tgattttat  gtaaggatga aaaactcgtc tacagttcaa    1320
catttactgt catattaaaa ataatacaat tgtgattccc tttaaaaaaa aaaggaattc    1380
```

<210> SEQ ID NO 17
<211> LENGTH: 1423
<212> TYPE: DNA
<213> ORGANISM: Medicago sativa
<400> SEQUENCE: 17

```
cgaattccca actaagtact gtaaaccata gagttcaaat tacagtactt tactttcatt    60
tgataccaac ctaccatatc attgctacac agaaactata tcaagatggt gagtgtatct    120
gaaattcgtc aggctcaaag ggcagaaggc cctgcaacca tcatggccat tggcactgca    180
aatccatcca actgtgttga acaaagcaca tatcctgatt tctacttcaa aatcacaaac    240
agtgagcaca aagttgaact caaagagaaa tttcaacgca tgtgtgataa atccatgatc    300
aagaggagat acatgtatct taccgaagag attttgaaag aaaatccaag tgtatgtgaa    360
tacatggcac cttcattgga tgctaggcag acatggtgg  tggtagaggt acctagactt    420
ggaaaggagg ctgcagtgaa ggctataaaa gaatggggcc aaccaaaatc aaagattaca    480
cacttaatat tttgtaccac aagtggtgta gacatgcctg gtgccgatta ccaactcaca    540
aaactcttag gtcttcgtcc atatgtgaaa aggtatatga tgtaccaaca agggtgcttt    600
gcaggtggga cggtccttcg tttggccaag gacttggctg agaacaataa aggtgctcgt    660
gtgttggttg tttgttctga agttactgcg gtgacattcc gtggtcctag tgatactcat    720
ttagacagtc ttgttggaca agcactcttt ggagatggtg ctgctgcact cattgttggt    780
tctgacccaa taccgaaaat tgagaaacct atatttgaga tggtttggac tgcacaaaca    840
attgctccag acagtgaagg agccattgat ggtcaccttg tcgaagctgg tctaacattt    900
caccttctta aagatgttcc tgggattgtt tcaaagaaca ttgataaagc attgattgag    960
gctttccaac cattaaacat ctctgattac aattcaatct tctggattgc tcacccaggt    1020
ggacccgcaa ttctagacca agttgaagaa aagttaggct aaaacctga  aaagatgaag    1080 gccactaggg aagtacttag tgaatatggt aacatgtcaa gtgcatgtgt attgttcatc    1140
```

| ttagatgaga tgagaaagaa atcggcacaa gcgggactta aaaccacagg agaaggcctt | 1200 |
| gactggggtg tgttgtttgg cttcggacct ggacttacca ttgaaaccgt tgttctccat | 1260 |
| agcgtggcta tatgaaatga ttgattgttt tattttattg tattactttt aaacttgctt | 1320 |
| gaaattccat gtaagaataa atacagagtt catgtaccat ggatgttaaa acgaatatac | 1380 |
| catttgtagc ttcttctttt tctcgcaaaa aaaaaaggaa ttc | 1423 |

<210> SEQ ID NO 18
<211> LENGTH: 7918
<212> TYPE: DNA
<213> ORGANISM: Arabidopsis thaliana

<400> SEQUENCE: 18

| ggtaccttag attatccaaa tttgtagctg caaaagttgt tcctgtgttc aagaaagaaa | 60 |
| gacctgtaaa atgatctgga tgtgtttggt tatatatata agaagactta aaagataatg | 120 |
| acttaatctc gtaacgagtc acacggacgt gacgctgaaa ctcacacacg ttggtgccac | 180 |
| gtctttgtct ttcctctttt gctctacttt tttctcctca taggtgatag gtcccataag | 240 |
| caatgaaata aaaaaaatgg taattgactt ttctccaaac atttttcgaat ctgattttct | 300 |
| ttttcaaggt tttataacct ctacattcca gaatatgact aatgacatca ttatccaatt | 360 |
| atttttttata ctgtaaactc attattatga atattcttta tttcaaaaaa ttaccattga | 420 |
| tttataagtt tattagtata atatataaca tatggaataa aacttttatt taaaaaaaaa | 480 |
| tattttttccc caaaaaaagt aggattaata acctgattaa taaataaaaa gtgttatatt | 540 |
| tttaagcatt gtatgcattt actttatcat agttgtcttg ttttaagag ttaaaaaata | 600 |
| atgatgaaca atttcacgga caacgattcc acgataaagc tttccctgca acactcagat | 660 |
| tttctaaaga cggttttgca ttgcgttttc tgggattcga aacccaaaca tgatgtacaa | 720 |
| gtattaatga actcttagtt aaccattaga ttaaaaatat tttcactatt aattttctct | 780 |
| taaaaatatt aataattttt tgaaatcaaa aattatagtt attttatttt aataaacgag | 840 |
| aaacactaca aaaaagtta actgcattta gataatttaa taaactaaaa tatccacata | 900 |
| aaaatttcaa atttatcaaa ataaaacat caatttgttt tttgtttttaa attaaagatt | 960 |
| tgctattgat tgcataagga agaaaacttt acaaagccga aaggcctaag agcccaacac | 1020 |
| acacaaaaga agaaccattt tggatcaagg gaaccgacca tgggtattag aagtagtggt | 1080 |
| ataaagccca tcatatccca acacataacc cacgaatgtt taatattaaa agtttgttgt | 1140 |
| tcggctcatg attagcgatg atcatacaga aagtttgtat ctaatacgtg ccttgaattt | 1200 |
| tatgtgtaca acaaacaaat taaattattc aaaaccataa attataaaaa ataattacag | 1260 |
| aaataaaact atattaagag cgagcctacc atccggtgtg caactttcta gtttatatac | 1320 |
| agtggcggat caacgttaat gaggcaaatt ggttcaaatt catctaaata agactagagt | 1380 |
| tcacaggttc gattcctcct tataacaatt tgctcccacc aattttttt gctgggtccg | 1440 |
| cccctggtta tatatatact tctacaccag gtttgggttc gagtccacac ataattaacg | 1500 |
| acacaattat agtgcacgat agaatgaact aaaacagcta gagcgtagag ggctcattgt | 1560 |
| ctataaaaat ccttcgttaa cttgcaagaa accaagagta gagggctcac acttaagtct | 1620 |
| cctacatgac gattatattt cgtcaaaaag aagcaattag ttagctttac agcatatcat | 1680 |
| ttcgcctagg ttttccatcg tacacgtaaa ttttcatgca agaaagcaga aatatacaaa | 1740 |
| tactaacttt tagatactga aaatgagatt cagattctag tcaaattttg ttaaaagtat | 1800 |
| ttataaattt aaattgcaag tcctcaaaaa gtacgactaa aaatgctttt cttagaaaat | 1860 |

```
gataataaac cggcgtttta tatataagtg tttcttttc tcttctgtcc agaagtaaat    1920
cattaagaac caatatggct tttcttaaac taatctccgt gataatcaaa tctttgatca    1980
ttctccacac aatcccatca acaacatcga tctcactaga tgcaccaaca atgattctaa    2040
tcggcactac taactataga gatagttgtc ccaaaaaaaa aaaaaaaaac taactagaga    2100
gataaatcat attcaataca tgtactattt ctactatact taagaaaatt tgtataccac    2160
tatcttaact cttaacactg aacatactat acactatctt aactcccaac tcttgtaaaa    2220
gaatatctaa ttttaagaaa agacttcaaa tgcttgttaa atttctagtg aagatgcaca    2280
ttctaaaaac tggtaaaatg gtaagaaaaa aatatataaa aaaatagcct tattaaaatt    2340
tatatctcct atttctctat ccaaactaca cggatgaagc ttattgttat tcatccaccc    2400
tttttctcaa ttctgtccta tttcttgtgc atgaaacttc tccatcttgt aatcggataa    2460
atcataccca aattttttct ttctgaaaac atatataccc gaacattaat tactatcgtc    2520
ctttctccta attttgttaa gaaacatgtt tgtttgtttt tagtactgaa aaaggatgga    2580
gatacttgct agatcctatg aaccttttct ctctaggaca aatcagtaac caaacaataa    2640
cttagcaaat taagcacgac agctaataca taaaatgtgg atatcaaaca tgcacgtcac    2700
ttccttttt ccgtcacgtg tttttataaa ttttctcaca tactcacact ctctataaga    2760
cctccaatca tttgtgaaac catactatat atacctctt ccttgaccaa tttacttata    2820
ccttttacaa tttgtttata tattttacgt atctatcttt gttccatgga gggttcgtcc    2880
aaagggctgc gaaaaggtgc ttggactact gaagaagata gtctcttgag acagtgcatt    2940
aataagtatg gagaaggcaa atggcaccaa gttcctgtaa gagctggtat gttatttacg    3000
aacacacaca cactaaccga cacacacaca cacaaatatg aatatctata atcactacca    3060
atagtcttcg ttctctctat tttctattca gaaaattgat taatacccgg tattaaaaaa    3120
aaaaaaaaaa atttgtttaa atgagtacaa atcattgtta caacttcttt atgctgtttt    3180
tacatgctat taaaggttgt gcatgaaaat ttcttttgct gttcgtattt gttttacacc    3240
taaacgaaga ttttttactta aaattaaaga aaaaaaatta tactaatttt agttacgttg    3300
cgtattgcta gcttctccta taaagtcgtt caaattttta cacgcttgtc ttcttgtaaa    3360
tgaattcgtg ggaaaatttt gtatgaacac gtgtttctgt gttggaacag ttctttattt    3420
ttattggtgt gcatagattc ttcctgataa aatatataga aggagacaaa taaaaaacag    3480
tcttagtatg taggtataat caaagaatca attattggtt ttgtagggct aaaccggtgc    3540
aggaaaagtt gtagattaag atggttgaac tatttgaagc caagtatcaa gagaggaaaa    3600
cttagctctg atgaagtcga tcttcttctt cgccttcata ggcttctagg gaataggtat    3660
taattgttac ctcgatacta cttaactcgg agagtcgtca taagttaata ctaataacat    3720
atgtatattt tcttacaatt gttaggtggt ctttaattgc tggaagatta cctggtcgga    3780
ccgcaaatga cgtcaagaat tactggaaca ctcatctgag taagaaacat gaaccgtgtt    3840
gtaagataaa gatgaaaaag agagacatta cgcccattcc tacaacaccg gcactaaaaa    3900
acaatgttta taagcctcga cctcgatcct tcacagttaa caacgactgc aaccatctca    3960
atgccccacc aaaagttgac gttaatcctc catgccttgg acttaacatc aataatgttt    4020
gtgacaatag tatcatatac aacaaagata agaagaaaga ccaactagtg aataatttga    4080
ttgatggaga taatatgtgg ttagagaaat tcctagagga aagccaagag gtagatattt    4140
tggttcctga agcgacgaca acagaaaagg gggacacctt ggcttttgac gttgatcaac    4200
```

```
tttggagtct tttcgatgga gagactgtga aatttgatta gtgtttcgaa catttgtttg    4260
cgtttgtgta taggtttgct ttcacctttt aatttgtgtg ttttgataaa taagctaata    4320
gtttttagca ttttaatgaa atatttcaag tttccgtgtt tacatttttga agaaaataaa   4380 atattaatat attctgaaga tttttgtttt tttttggtta tctacatgac aacagtaaaa    4440
atagaaaaaa aatcttattt tttgaaaaag gtatgtatcc ggtgtttaga atactttccg    4500
aaatcaaacc gcctatattt ctaatcacta tgtaaaattt taaaccaatt gggttaaaac    4560
tcaactaaca aactttctaa ataaatgtca ttttttgtttt caaatatgat tgaactcgga   4620
tttaggagtt ttaccccttca gtaccaaacc ttctctaccg accatgtatg gttgggcaaa   4680
tgtcatgttt tacaatgttt agattactaa acactttggt tgagaaggca atgctttatt    4740
tatatattct gaagtcatgt tttagtgtta tttttattta tttttaaatg catagattgt    4800
taacgtgcag attctcatat gggcttagtt tctggatttt gattatcaaa accgtattcc    4860
actcttaaat gattacgaca aaaaaatcaa tactactaac aaacctatttt cccagttatt    4920 aattagtcaa taacaattgt caaatttaat aacgtacttg ctagtaataa agttttaacg    4980
acgatcatag ataggttttt gaaacccata ctcgcagaag ttctgataca aaaatttgta    5040
ctccctctat ttcaaaatat taaatgtttt agataaaagc acaatgttta agaaactaat    5100
taatcttgag tttcttacat tataaacata aattaatatc tattaaaaat aatttgacca    5160
atgatataac ttacagcata atataaatag ttaaaaaaaa actgtttact ttaataattt    5220
gcataacaac tagctagtct ggtccaagaa cggtagtagg atgagatttt agaaggtcgt    5280
aatgtgtaag actaataatc atgcgataga cgatcatgca tgaattattt tatgtaatac    5340
ttatatggtt ccaaaatcta taagaaccct caattataaa agtaatatct attaaatatt    5400
taaacgataa tttcatacgg aaaattaata gataaattct tctatttgtt tttaaatata    5460
tgtaaatgcg aaagtgtccc atgcaatttt atatatttaa tcaagtgaaa actcgaaaac    5520
aaaaaacttg atgtacttca aacaagtttt tttggcaagt aatacccatt ctgttccggt    5580
tggactataa atgcatggaa aagcaccaaa aaaggcatgg atactttcgc gattttttgcc   5640 attttttgtat ctttgttcat cgctccgttc aaaagaacct cttgtcgtta ctataatag    5700 ttatggacca acggtattgt catgtatcaa ataactatg tagcatacgt gtattgtgaa     5760
tcaatgaagc aatagagaga taacatactg aaacgtccac atctcgttta taaaaaaatc    5820
gtctacatgc ttctctttgg ctggacatcc caacttttct caccgtaacc agtgaaattg    5880
tattatttgg taagaattac ggatggagtt agattttatt tgttgtgtgt gtataaatca    5940
atacttatac agttttttacg tgtataacgg cacgcctcat gggttttgct aataaggtcc    6000
aagtagtgga cagaaaagaa cttgtgattg aatagtgttt tgtattgaaa ggttaaaacg    6060
tgtttccaaa tggattcaac caaattccaa catgttcagt gtcgtacatg cgaaaacatt    6120
atcgagtaaa ataagttcca ttatactttg attttgtatt gattccatag agtagaaatg    6180
tgtgctttag cttatagtta aacactatct tcaagggggt aatgctggat tcgaagtatt    6240
taattagtcc tgttcgaccg aatcaaagtt caatcgattt tgaaaacaa tcatttcggg     6300 tatagcttga aacatcccaa accacaagtt ccaaaagcac acatattatc accattcaac    6360
taaccattcg ggtttgataa ccggtagttg gatgttcaaa gatctcatca gatttggtgt    6420
caagaggata attgtgattg agttgtgaac ccttgtgatg gagatagttt ccttgtttgg    6480
atgttaagtt gaattttggg atcatccttg tttcaaaaag actggaaaac acacaaaaaa    6540
aaaaaaaaaa aaacttgcaa ataaatttaa ttttttagaaa ttttatattg tagtgaaaaa   6600
```

-continued

```
tgtttgcaaa ttttagctgg agatgttttt ccatttggaa ttttttttct taattttgcc    6660
ttttatttta cattgtatat tgctagcttc ttcttgacaa gaaagaacga tgtcaacctc    6720
tgatttgtct tcttataaat gaatttgttg aaaattgctg tacgagcaag tgttttttgtg   6780 ttggaacatg tctctatttc tattggtgtg catagattct tcatgataaa atatataagg    6840
agacaaataa gaaagcagtc ttattaggta ggattgccta aaatattcgt tagattcgct    6900
tggatctatt attcggttaa attgattcga aaaatctgaa tatccataat tttacgaagc    6960
aaatcaaata ttaaaaattg atattcgtta aaaacagaaa aataacaaa tattaaattt     7020 aaataggcgg atatcctctc taattcggta tacatgaata tatgtatatg tatatagata    7080
agtataaata tatatattaa taatcttact ctttttatat gtaagtttta gaagtttatg    7140
ttcatcaaat tagttattta actattagtt taaaaaattg aaaagagata ttttttccaa    7200
tgaagtttta cttatttttgg attaaatttc taattttttat gttttttaatt tttataattg 7260 tttttgagat atacttaaca aatcgaatat ctagcaaata actcggattt taacggaata   7320
tctggacagc cggatattcg gttactttcg aaacaaatac gaatcagaaa actaattatt    7380
ccgatatagc aaatcggatc acaaatacta ccaaaatcca tgatatatgt gtcgtgtcca    7440 ccccctattag taggtataat taattgtaat tagtggtttt gtaagactaa atcagcccag   7500
gaagagttgt agactaagat gcttatacta tttgaagcca agtatcaaga gaggaagatt    7560
taggctctga tgaagttgat cttcttcttc gccttcccaa ccttctagga aatagtattt    7620
gttatacttt atactaatta attcttcgg gattcataag attattaata acatattatt     7680
cgtataatgt ttaacaactt ttagattggc tttgattgct ggtctattgg ctggtcagac    7740
cacaaacggt gtcaaaaatt acttgaacac tcaactgagt aagaaacatg aaccatgttg    7800
taagatttag ataaaaaaaa aaaaaagca ttacttccaa tgctaccata ctgggctaaa     7860
aatggatgtt tttaatctcg accttaatcc ttctcattta acagcagtgg cctaccaa     7918
```

<210> SEQ ID NO 19
<211> LENGTH: 1851
<212> TYPE: DNA
<213> ORGANISM: Arabidopsis thaliana

<400> SEQUENCE: 19

```
attttagag agagagctac cacgttttcg tatctccggg aacgatggat gaatcaagta      60
ttattccggc agagaaagtg gccggagctg agaaaaaaga gcttcaaggg ctgcttaaga    120
cggcggttca atctgtggac tggacttata gtgtcttctg gcaattttgt cctcaacaac    180
gggtcttggt gtgggggaat ggatactaca acggtgcaat aaagacgagg aagcaactc     240 aaccagcgga ggtgacggcg gaagaggctg cgttagagag gagccaacag ctcagggagc    300
tttatgagac acttttagcc ggagagtcaa cgtcagaagc aagagcatgc accgcattgt    360
caccggagga tttgacggag acagaatggt tttatctaat gtgtgtgtct ttctcttttc    420
ctcctccatc tgggatgcca ggaaaagcgt atgcaaggag gaagcacgta tggctaagtg    480
gtgcaaatga agttgacagt aaaactttt ctagagctat tctcgctaag agtgctaaaa     540
ttcagacagt ggttttgcatt ccaatgcttg atggtgttgt ggaactaggc acaacgaaaa   600
aggtaagaga agatgtagag tttgttgagc tcacaaagag tttcttctat gaccactgca    660
agacgaaccc aaagccggct ctttctgaac actccaccta cgaagtgcat gaagaagccg    720
aagacgaaga agaagtagaa gaagagatga caatgtcaga ggaaatgagg cttggctctc    780
```

```
ctgatgatga agatgtttcc aatcaaaatc tacactctga tcttcatatt gaatcaaccc    840
atacgttaga cacacatatg gacatgatga atctaatgga ggaaggtgga aactattctc    900
agacagtaac aacacttctc atgtcacacc ccacaagtct tctttcagat tcagtttcca    960
catattctta catccaatca tcgtttgcca cgtggagggt tgagaatggc aaagagcatc   1020
agcaagtgaa aacggcgccg tcgtcacaat gggtgctcaa acaaatgatc ttcagagttc   1080
ctttcctcca tgacaacact aaagataaga ggctaccgcg ggaagatctg agccacgtag   1140
tagcagagcg acgcaggagg gagaagctga acgagaaatt cataacgttg agatcaatgg   1200
ttccatttgt gaccaagatg gataaagtct caatccttgg agacaccatt gcgtacgtaa   1260
atcatcttcg aaagagggtc catgagcttg agaatactca tcatgagcaa cagcataagc   1320
ggacgcgtac ttgtaagaga aaacatcgg aggaggtgga ggtttccatc atagagaatg   1380
atgttttgtt agagatgaga tgtgagtacc gagatggttt gttgcttgac attcttcagg   1440
ttcttcatga gcttggtata gagactacgg cagttcatac ctcggtgaac gaccatgatt   1500
tcgaggcgga gataagggcg aaagtaagag ggaagaaagc aagcatcgct gaggtcaaaa   1560
gagccatcca ccaagtcata atacatgata ctaatctata ccctaact ttattgatgc    1620
caactctaga gaaggataat taagcgtatt tttgttttag cctcacatgt attaagacat   1680
cagttacata tatagccgga tgcaacatat aaatgaaaat gtactagatg atattgttca   1740
tttgtccaat gtagtacttg tgtatgatgc aattgcaaca tataaatgca aatgtactag   1800
atgacgatgt tgttcgttgt ccaatttagt actaaaaaaa aaaaaaaaaa a             1851
```

<210> SEQ ID NO 20
<211> LENGTH: 518
<212> TYPE: PRT
<213> ORGANISM: Arabidopsis thaliana

<400> SEQUENCE: 20

```
Met Asp Glu Ser Ser Ile Ile Pro Ala Glu Lys Val Ala Gly Ala Glu
1               5                   10                  15

Lys Lys Glu Leu Gln Gly Leu Leu Lys Thr Ala Val Gln Ser Val Asp
            20                  25                  30

Trp Thr Tyr Ser Val Phe Trp Gln Phe Cys Pro Gln Gln Arg Val Leu
        35                  40                  45

Val Trp Gly Asn Gly Tyr Tyr Asn Gly Ala Ile Lys Thr Arg Lys Thr
    50                  55                  60

Thr Gln Pro Ala Glu Val Thr Ala Glu Glu Ala Leu Glu Arg Ser
65                  70                  75                  80

Gln Gln Leu Arg Glu Leu Tyr Glu Thr Leu Leu Ala Gly Glu Ser Thr
                85                  90                  95

Ser Glu Ala Arg Ala Cys Thr Ala Leu Ser Pro Glu Asp Leu Thr Glu
            100                 105                 110

Thr Glu Trp Phe Tyr Leu Met Cys Val Ser Phe Ser Phe Pro Pro Pro
        115                 120                 125

Ser Gly Met Pro Gly Lys Ala Tyr Ala Arg Arg Lys His Val Trp Leu
    130                 135                 140

Ser Gly Ala Asn Glu Val Asp Ser Lys Thr Phe Ser Arg Ala Ile Leu
145                 150                 155                 160

Ala Lys Ser Ala Lys Ile Gln Thr Val Val Cys Ile Pro Met Leu Asp
                165                 170                 175

Gly Val Val Glu Leu Gly Thr Thr Lys Lys Val Arg Glu Asp Val Glu
            180                 185                 190
```

```
Phe Val Glu Leu Thr Lys Ser Phe Phe Tyr Asp His Cys Lys Thr Asn
            195                 200                 205

Pro Lys Pro Ala Leu Ser Glu His Ser Thr Tyr Glu Val His Glu Glu
210                 215                 220

Ala Glu Asp Glu Glu Val Glu Glu Glu Met Thr Met Ser Glu Glu
225                 230                 235                 240

Met Arg Leu Gly Ser Pro Asp Asp Glu Asp Val Ser Asn Gln Asn Leu
                245                 250                 255

His Ser Asp Leu His Ile Glu Ser Thr His Thr Leu Asp Thr His Met
            260                 265                 270

Asp Met Met Asn Leu Met Glu Glu Gly Gly Asn Tyr Ser Gln Thr Val
            275                 280                 285

Thr Thr Leu Leu Met Ser His Pro Thr Ser Leu Leu Ser Asp Ser Val
        290                 295                 300

Ser Thr Tyr Ser Tyr Ile Gln Ser Ser Phe Ala Thr Trp Arg Val Glu
305                 310                 315                 320

Asn Gly Lys Glu His Gln Gln Val Lys Thr Ala Pro Ser Ser Gln Trp
                325                 330                 335

Val Leu Lys Gln Met Ile Phe Arg Val Pro Phe Leu His Asp Asn Thr
            340                 345                 350

Lys Asp Lys Arg Leu Pro Arg Glu Asp Leu Ser His Val Val Ala Glu
            355                 360                 365

Arg Arg Arg Arg Glu Lys Leu Asn Glu Lys Phe Ile Thr Leu Arg Ser
        370                 375                 380

Met Val Pro Phe Val Thr Lys Met Asp Lys Val Ser Ile Leu Gly Asp
385                 390                 395                 400

Thr Ile Ala Tyr Val Asn His Leu Arg Lys Arg Val His Glu Leu Glu
                405                 410                 415

Asn Thr His His Glu Gln Gln His Lys Arg Thr Arg Thr Cys Lys Arg
            420                 425                 430

Lys Thr Ser Glu Glu Val Glu Val Ser Ile Ile Glu Asn Asp Val Leu
        435                 440                 445

Leu Glu Met Arg Cys Glu Tyr Arg Asp Gly Leu Leu Leu Asp Ile Leu
    450                 455                 460

Gln Val Leu His Glu Leu Gly Ile Glu Thr Thr Ala Val His Thr Ser
465                 470                 475                 480

Val Asn Asp His Asp Phe Glu Ala Glu Ile Arg Ala Lys Val Arg Gly
                485                 490                 495

Lys Lys Ala Ser Ile Ala Glu Val Lys Arg Ala Ile His Gln Val Ile
            500                 505                 510

Ile His Asp Thr Asn Leu
        515

<210> SEQ ID NO 21
<211> LENGTH: 5777
<212> TYPE: DNA
<213> ORGANISM: Arabidopsis thaliana

<400> SEQUENCE: 21 gatcttttc atgttttgtt tttattcata catatccaag agactttaaa tatttgttta      60
tcaatattac aaattatcac ataatatatt cgtgttttgc tttattcat atgattccaa     120 aaatcactta ttaaaagcta ttcattttaa acttgttcca acctaaacat ctttattttt     180
aaagtctttt cagaatatta gaccaaaaat ataaatacat tttaataata tatatgacca     240
```

-continued

```
aattaattat ttaaaactttt tgcagatgca tcatctatat atacatttttt gcagccactt    300
tgtgaaataa atcctggagt tgggatttat ttacagcggc tgccactgga atttaataat    360
tattttttgat aattagaaag aaaatcttct aattaaaatat ttgacatttta acaatcttcc   420
caaaatctct ctaccttaac tacacgatta attactaaaa taaaacttcc aaaatattta    480
atattattta attactacaa aattatcatt tttgatattg cttttctaca tgattataat    540
catcaaaccg tagagatctt tgatagcatt taattactac aaaattacaa aatatttaga    600
caataattca taaacatatc ataaataaga tcaacattaa taaaataaat gagttttttt    660
tagaggacgg gttggcggga cgggtttggc aggacgttac ttaataacaa ttgtaaacta    720
taaaataaaa acatttttata actatataca atttacaaac ttttatatat attaatttaa    780
aaaataaatt gttcccgcgg tgtaccgcgg gttaaaatct agttatattt taaaaatcga    840
gatgttacat atgtgttaaa ctttcttttt tgtcttctta tgtgatatca aattttatga    900
tcttatcgat tttaatcagg tatatcttgg tatagcctta gatttcataa tcgcatataa    960
aaatcataaa ttatgtagaa actagttata atcaaataat atttatttca tatggtatac   1020
caaaattaag tattcaattg ctacgtggat attaataatt tgaattcggt aacatactct   1080
tttttctttt gttaaaccaa agaatctcaa acaaagtttt ttgatcatag ttactaaatc   1140
attttttggtg aataaccgag agaatgtctc ccgacttcta ttaaaaaaca aaaataacaa   1200
ttacacaatc actcgtcttg aacaaacagg tctagaaaca tcatcccgta agatttcatc   1260
cgcacaccgg agaacataaa caagagcata aaagcttaaa gacaagcata gtttgttaac   1320
atgtccgtaa aatgattagc ctctctatat gtgaaacacg gtcaatctag ttttttcgata   1380
aaaaactata gcgcaaacgt actagaaatg atagcagatg agagtcccat aactttgtct   1440
tcaaaatctc aaccaccatt taccacaaat atggggatga aaacaggcaa acggtctcat   1500
acgtcgtaaa taagcattct taatgtcaag ttggtagata ggccataaaa taagcatcct   1560
tatgtttagc gcatagcctc cacaccattc accctcctca ttacgtatca gaccaccacc   1620
agccgcgagt ctcgaattgc cataaaaatac cccatcagta tttaatttaa accagcccat   1680
agacgagata agccatttta tcagcttctc aacccgacca gcccctttgtg ttgccttttcc   1740
gctactagct ctcgcctcca atacctcctt agctaactct cttatgaacc gcacccatt    1800
cttccatact ttattctccc caaaaactag ctaattgaat taccaacatt tgatcaagat    1860
aatatactag gtagctaatt aatgagctca tttttttttt gtcgtcaatg ggctaattta    1920
ttaattacag tatgaactat tgactattat tctaaataag tgaatatcac gagtatgtac    1980
gaattattgg atgtatctat ttgtattgat tgatgtaata tcaaatagta agaatttgga    2040
gtaaacgtgg gtttggggtt gaagcaggta gggcatgtca aagtagggcg tctttcgtta    2100
tgtccctttc ctctaaattt gaacctctgt cattgtttac agaaaaatcg taataaccca    2160
taaatgtgtt ttaaaaaaca ttatttcgag ttttctacac atattctagt catgtttaat    2220
ttgaatcttt tcttatttaa gtaagcttta gacattttta acctaagttt tcttctcct    2280
tcataaattt tgagatctat ataatgttct tacatttttgg atcaagatct tcatattctc    2340
attccaatta gtaaaagatt ttttcacctt ttaatctctt atcttttatt tatattcttt    2400
agttatgttt atgctttttca tcatatttag tggttagttt ttattattta tttattgatt    2460
catgacttat gctagattat gataagaatt tatgttacca cttgataaat cctccatttg    2520
acatgtgttt aatgctagat ttatattgtc tccaaattta caactttgat gtcttatgat    2580
```

```
aaatgccaac aaccaaattt cagataaaga ttagcagact aactaagctt attattcact   2640
tgcaaggtgg agtgatgttg aaagaaccct cacagacacg tcattgggaa gactaaatct   2700 cttttagca cgttacacct tgagatcgc gtttattcca tatggagaga gagcaacaat    2760
acgagacatg gagaggcacc attaccgccg gcgcaactgc ttccaaatat tgacaaacaa   2820
atttgaatct ggatcttctc tattcgtgaa caaggagata gaagctacga tgaatgcatg   2880
gaagcttggt ttgctttaat ataaacacta aaggggagta gaactttctt gaaaaattgt   2940
atgcaaatta tttaccgaat gttaaaagct ttttttcgaat aaattttaca ttttcttaat  3000
aataataata aaaaaggatt gttgattatc ttaatcacaa acaatttatt ttagctgaat   3060
tagacaattg ttagtaaaat gattagagtg tcacatatta atgttgttag tgtttcatgt   3120
catcctagtg atccaataat taggccattc tatagctcgt aacgttaaaa taaaaggccc   3180
attatctgaa tatacagaag cccattatca atagatacat taaaagatac tgattaatcc   3240
agagggttta tatctacgcc gtctccattg attatttctc cgtctcttga aaaatccgac   3300
tgacactgac ctcaaaactc tcctctcact ttcgtcgtga agaagccaaa tctcgaatcg   3360
aatcagcacc acacatttcc atggataatt cagctccaga ttcgttatcc agatcggaaa   3420
ccgccgtcac atacgactca ccatatccac tctacgccat ggctttctct tctctccgct   3480
catcctccgg tcacagaatc gccgtcggaa gcttcctcga agattacaac aaccgcatcg   3540
acattctctc tttcgattcc gattcaatga ccgttaagcc tctcccgaat ctctccttcg   3600
agcatcctta tcctccaaca aagctaatgt tcagtcctcc ttctctccgt cgtccttcct   3660
ccggagatct cctcgcttcc tccggcgatt tcctccgtct ttgggaaatt aacgaagatt   3720
catcaaccgt cgagccaatc tcggttctca acaacagcaa aacgagcgag ttttgtgcgc   3780
cgttgacttc cttcgattgg aacgatgtag agccgaaacg tctcggaact tgtagtattg   3840
atacgacgtg tacgatttgg gatattgaga agtctgttgt tgagactcag cttatagctc   3900
atgataaaga ggttcatgac attgcttggg gagaagctag ggttttcgca tcagtctctg   3960
ctgatggatc cgttaggatc tttgatttac gtgataagga acattctaca atcatttacg   4020
agagtcctca gcctgatacg cctttgttaa gacttgcttg gaacaaacaa gatcttagat   4080
atatggctac gattttgatg gattctaata aggttgtgat tctcgatatt cgttcgccga   4140
ctatgcctgt tgctgagctt gaaagacatc aggctagtgt gaatgctata gcttgggcgc   4200
ctcagagctg taaacatatt tgttctggtg gtgatgatac acaggctctt atttgggagc   4260
ttcctactgt tgctggaccc aatgggattg atccgatgtc ggtttattcg gctggttcgg   4320
agattaatca gttgcagtgg tcttcttcgc agcctgattg gattggtatt gcttttgcta   4380
acaaaatgca gctccttaga gtttgaggtg agagtttctc tttcgctaca taattctcat   4440
ttgctaggcc tagattctaa tgaggaagca ttgattattg gtttagattg tgttgcatta   4500
cagatagttc tctaggtttg gtaactaaac gttttttcga ttcttgataa caaagccact   4560
agagatttga cactaactcg ttttagattt acctgaatca atatctctgt taaaatcaat   4620
tactttgtta tgcatacata aatcacagtt tagtagtcat atatattggc tcttattagc   4680
gacaggtctc acacttgctg taatggctga tagtgtagta gtcatatgtt ggctttcatc   4740
taagttgatg tatcatatga tgaatagttg tacactcgtc aggttctaat ttttaccat    4800 aattcttcag tctattttt tttgagacaa tctattctta atttaacgaa gccactagct   4860
acgtatacaa atattgttaa tttaacgaag tatctgagaa ttgtttactg ctgactctgc   4920
tgtatgccct cagaaacata tagaagtgga attggaaact tcatgctggt ttgaacatct   4980
```

```
ttgtatgtgt gcttcaggtt tttgtaactc atttagacaa cagcattgca tatatacacg    5040
cacatatgca acctagaaaa tcaaataacc tttccttata attactatcc atttcacttg    5100
atgtcaggtg cagatgtgaa gtgatcaata aggattttag catagacccg tataatcgtc    5160
atgtgcgtaa gtaggtttgg tttgcgctcc ctctcgcttt taggtccgca atgactctgt    5220
atctatctga ttgtaactaa aactgaattc atttgatgaa ccaaatgata ctattatctt    5280
atgttgtgta taaaacccaa ccaggatata ttgcggtttc tggtgtttag atttggtaat    5340
tggagcttag tacaatgcaa ccctgtcttg ctttattgga cgtctctaag ataaatcagc    5400
ttgcaatgaa ttccaatgga gtttgtcagt ttgaattaac ttctttgcat aattaacaca    5460
aagatttgca gtataaattc cattggaaga cttatttgtt tatttgacac agatttaaat    5520
tgaatttcaa tggagtttca gtcgactatg tgacacaaag atttgaaatg aactccaatg    5580
ggaatttgat gagtaaatta ttataaacaa tccaatgttt gacacaaata ttttagaatc    5640
ttcacatctg aagtcttata aatcgtagca aaattttcaa tcttgaaaat tataaaaaat    5700
gagaattaat ttaaatcact gatccgataa tctcctctag aaatataaga atctataaac    5760
cattaatagt agaattc                                                   5777

<210> SEQ ID NO 22
<211> LENGTH: 341
<212> TYPE: PRT
<213> ORGANISM: Arabidopsis thaliana

<400> SEQUENCE: 22

Met Asp Asn Ser Ala Pro Asp Ser Leu Ser Arg Ser Glu Thr Ala Val
1               5                   10                  15

Thr Tyr Asp Ser Pro Tyr Pro Leu Tyr Ala Met Ala Phe Ser Ser Leu
            20                  25                  30

Arg Ser Ser Ser Gly His Arg Ile Ala Val Gly Ser Phe Leu Glu Asp
        35                  40                  45

Tyr Asn Asn Arg Ile Asp Ile Leu Ser Phe Asp Ser Asp Ser Met Thr
    50                  55                  60

Val Lys Pro Leu Pro Asn Leu Ser Phe Glu His Pro Tyr Pro Pro Thr
65                  70                  75                  80

Lys Leu Met Phe Ser Pro Pro Ser Leu Arg Arg Pro Ser Ser Gly Asp
                85                  90                  95

Leu Leu Ala Ser Ser Gly Asp Phe Leu Arg Leu Trp Glu Ile Asn Glu
            100                 105                 110

Asp Ser Ser Thr Val Glu Pro Ile Ser Val Leu Asn Asn Ser Lys Thr
        115                 120                 125

Ser Glu Phe Cys Ala Pro Leu Thr Ser Phe Asp Trp Asn Asp Val Glu
    130                 135                 140

Pro Lys Arg Leu Gly Thr Cys Ser Ile Asp Thr Thr Cys Thr Ile Trp
145                 150                 155                 160

Asp Ile Glu Lys Ser Val Val Glu Thr Gln Leu Ile Ala His Asp Lys
                165                 170                 175

Glu Val His Asp Ile Ala Trp Gly Glu Ala Arg Val Phe Ala Ser Val
            180                 185                 190

Ser Ala Asp Gly Ser Val Arg Ile Phe Asp Leu Arg Asp Lys Glu His
        195                 200                 205

Ser Thr Ile Ile Tyr Glu Ser Pro Gln Pro Asp Thr Pro Leu Leu Arg
    210                 215                 220
```

```
Leu Ala Trp Asn Lys Gln Asp Leu Arg Tyr Met Ala Thr Ile Leu Met
225                 230                 235                 240

Asp Ser Asn Lys Val Val Ile Leu Asp Ile Arg Ser Pro Thr Met Pro
            245                 250                 255

Val Ala Glu Leu Glu Arg His Gln Ala Ser Val Asn Ala Ile Ala Trp
        260                 265                 270

Ala Pro Gln Ser Cys Lys His Ile Cys Ser Gly Gly Asp Asp Thr Gln
    275                 280                 285

Ala Leu Ile Trp Glu Leu Pro Thr Val Ala Gly Pro Asn Gly Ile Asp
290                 295                 300

Pro Met Ser Val Tyr Ser Ala Gly Ser Glu Ile Asn Gln Leu Gln Trp
305                 310                 315                 320

Ser Ser Ser Gln Pro Asp Trp Ile Gly Ile Ala Phe Ala Asn Lys Met
            325                 330                 335

Gln Leu Leu Arg Val
            340

<210> SEQ ID NO 23
<211> LENGTH: 1639
<212> TYPE: DNA
<213> ORGANISM: Arabidopsis thaliana

<400> SEQUENCE: 23
agggaaaaaa aaaacagagg aactaataaa cggaccatga gctccacaga gacatacgag      60
ccgttattga cacgactcca ctcggattct cagataactg aacggtcttc gccagagata     120
gaggagtttc tccgccgtcg tggatccaca gtgacaccac ggtggtggct aaagctggca     180
gtgtgggagt caaagcttct atggacactc tctggagcct ctatagtggt ctctgttctg     240
aattacatgc tcagcttcgt caccgtcatg ttcaccggtc atctcggttc tcttcagctc     300
gccggcgctt ccatcgccac cgtcggaatc caaggcctag cttacggtat catgttagga     360
atggcgagcg cggtccaaac agtgtgtggt caagcgtacg agcgagaca  gtactcatca     420 atgggaataa tctgccaacg agccatggtc ttgcaccttg cagctgcagt cttcctcacg     480
ttcctctact ggtactcggg tccaatcctt aaaacaatgg ccaatccgt  agccatagca     540 cacgagggtc agatctttgc acgtggaatg attccacaaa tttacgcatt tgccctcgct     600
tgcccgatgc agaggtttct tcaggctcag aacatagtga accctttggc ttacatgtcc     660
ttaggagttt tcttgctcca cacgttactc acgtggctgg ttaccaacgt gctggatttc     720
ggcttgcttg gggcggctct gattctcagt ttctcatggt ggctgctagt agctgtgaat     780
ggtatgtata tcttgatgag cccgaattgt aaggagacat ggacagggtt ttcaacgagg     840
gcatttagag ggatatggcc ttacttcaag ctcacgtag  cttcagcagt tatgctatgt     900
ttggagatat ggtacaacca agggctagtg attatctctg gtttactctc caatccgaca     960
atttctctag acgctatttc gatttgcatg tattacttga attgggatat gcagttcatg    1020
cttggtctaa gtgcagcaat cagtgtgcga gtgagcaatg agctaggagc gggaaatcca    1080
cgagtggcta tgttatcagt agtggttgtc aacatcacga ctgttctcat cagctcagtt    1140
ctctgtgtca tcgtgcttgt gttccgcgtt ggccttagca aagccttcac cagcgatgca    1200
gaagttatag cagccgtctc tgacctcttt cctcttctcg ccgtttccat tttcttaaac    1260
ggaatccagc caattctctc tggggttgct attgggagtg ggtggcaagc agtggtggct    1320
tatgtgaatc ttgttacgta ctatgtcatt ggtcttccta ttggctgtgt ccttggcttc    1380
aaaaccagtc ttggagttgc tgggatctgg tggggatga  ttgcaggagt catacttcaa    1440
```

```
accctaactt tgattgttct tacacttaaa actaattgga cttccgaggt agaaaatgca    1500
gctcagagag taaagacttc ggcaactgag aatcaagaga tggctaacgc aggtgtttaa    1560
gataacagca acagtgactc tgttttttt ccctctttt ggtgaaaaga gatataagat    1620
gaaaaaaaaa aaaaaaaa                                                  1639
```

<210> SEQ ID NO 24
<211> LENGTH: 507
<212> TYPE: PRT
<213> ORGANISM: Arabidopsis thaliana

<400> SEQUENCE: 24

```
Met Ser Ser Thr Glu Thr Tyr Glu Pro Leu Leu Thr Arg Leu His Ser
1               5                   10                  15

Asp Ser Gln Ile Thr Glu Arg Ser Ser Pro Glu Ile Glu Glu Phe Leu
            20                  25                  30

Arg Arg Arg Gly Ser Thr Val Thr Pro Arg Trp Trp Leu Lys Leu Ala
        35                  40                  45

Val Trp Glu Ser Lys Leu Leu Trp Thr Leu Ser Gly Ala Ser Ile Val
50                  55                  60

Val Ser Val Leu Asn Tyr Met Leu Ser Phe Val Thr Val Met Phe Thr
65                  70                  75                  80

Gly His Leu Gly Ser Leu Gln Leu Ala Gly Ala Ser Ile Ala Thr Val
                85                  90                  95

Gly Ile Gln Gly Leu Ala Tyr Gly Ile Met Leu Gly Met Ala Ser Ala
            100                 105                 110

Val Gln Thr Val Cys Gly Gln Ala Tyr Gly Ala Arg Gln Tyr Ser Ser
        115                 120                 125

Met Gly Ile Ile Cys Gln Arg Ala Met Val Leu His Leu Ala Ala Ala
130                 135                 140

Val Phe Leu Thr Phe Leu Tyr Trp Tyr Ser Gly Pro Ile Leu Lys Thr
145                 150                 155                 160

Met Gly Gln Ser Val Ala Ile Ala His Glu Gly Gln Ile Phe Ala Arg
                165                 170                 175

Gly Met Ile Pro Gln Ile Tyr Ala Phe Ala Leu Ala Cys Pro Met Gln
            180                 185                 190

Arg Phe Leu Gln Ala Gln Asn Ile Val Asn Pro Leu Ala Tyr Met Ser
        195                 200                 205

Leu Gly Val Phe Leu Leu His Thr Leu Leu Thr Trp Leu Val Thr Asn
    210                 215                 220

Val Leu Asp Phe Gly Leu Leu Gly Ala Ala Leu Ile Leu Ser Phe Ser
225                 230                 235                 240

Trp Trp Leu Leu Val Ala Val Asn Gly Met Tyr Ile Leu Met Ser Pro
                245                 250                 255

Asn Cys Lys Glu Thr Trp Thr Gly Phe Ser Thr Arg Ala Phe Arg Gly
            260                 265                 270

Ile Trp Pro Tyr Phe Lys Leu Thr Val Ala Ser Ala Val Met Leu Cys
        275                 280                 285

Leu Glu Ile Trp Tyr Asn Gln Gly Leu Val Ile Ser Gly Leu Leu
    290                 295                 300

Ser Asn Pro Thr Ile Ser Leu Asp Ala Ile Ser Ile Cys Met Tyr Tyr
305                 310                 315                 320

Leu Asn Trp Asp Met Gln Phe Met Leu Gly Leu Ser Ala Ala Ile Ser
                325                 330                 335
```

```
Val Arg Val Ser Asn Glu Leu Gly Ala Gly Asn Pro Arg Val Ala Met
            340                 345                 350

Leu Ser Val Val Val Asn Ile Thr Thr Val Leu Ile Ser Ser Val
        355                 360                 365

Leu Cys Val Ile Val Leu Val Phe Arg Val Gly Leu Ser Lys Ala Phe
        370                 375                 380

Thr Ser Asp Ala Glu Val Ile Ala Ala Val Ser Asp Leu Phe Pro Leu
385                 390                 395                 400

Leu Ala Val Ser Ile Phe Leu Asn Gly Ile Gln Pro Ile Leu Ser Gly
                405                 410                 415

Val Ala Ile Gly Ser Gly Trp Gln Ala Val Ala Tyr Val Asn Leu
        420                 425                 430

Val Thr Tyr Tyr Val Ile Gly Leu Pro Ile Gly Cys Val Leu Gly Phe
        435                 440                 445

Lys Thr Ser Leu Gly Val Ala Gly Ile Trp Trp Gly Met Ile Ala Gly
        450                 455                 460

Val Ile Leu Gln Thr Leu Thr Leu Ile Val Leu Thr Leu Lys Thr Asn
465                 470                 475                 480

Trp Thr Ser Glu Val Glu Asn Ala Ala Gln Arg Val Lys Thr Ser Ala
                485                 490                 495

Thr Glu Asn Gln Glu Met Ala Asn Ala Gly Val
            500                 505

<210> SEQ ID NO 25
<211> LENGTH: 1102
<212> TYPE: DNA
<213> ORGANISM: Arabidopsis thaliana

<400> SEQUENCE: 25
aaaacatttc atctctctcc aacaactatt caccacattc aatggagtca ccaccactat      60
acgagatatc ctcaagctct tcttctgaaa acctagaca ccatttccaa tcccttgatc     120
tcttccctaa cctcaaccaa aactcttgta tcaacaatac cctaattgag cctttaccgc     180
ttattgatcg cataaacttg aactcaaacc tagacctaaa ccctaatccc ttgtatgcgg     240
aagaaggaga gcaagaggag gaagaagaag aagaagaaga ccgtgaagtg gacgtggact     300
tacacatcgg ccttcctggt tttggtaaac caagcaatga tgctaaacag ctgaagaaga     360
gaaatgggaa ggagatcgcc acatatgacg ccggaaaagg catcgagaat gaactttccg     420
gaaaggcata ctggatcccg cgccggagc aaattctcat agggttcact catttttctt     480
gccatgtatg cttcaagaca ttcaatcgct acaacaatct tcagatgcac atgtggggac     540
atggttcaca atacaggaaa ggaccggagt cactgaaagg cacacagcca cgagccatgt     600
tagggatccc ttgttactgc tgcgttgaag ggtgcaggaa ccacattgac catcctcgtt     660
ccaagccact gaaagacttt aggacgctcc aaacgcacta caaacgcaaa cacggacaca     720
aacccttctc gtgtcgcctt tgcggtaagc ttttggctgt caagggcgat tggcgaacac     780
atgagaagaa ttgtggaaaa cgttgggttt gcgtttgcgg ttctgatttt aaacacaaac     840
gttctcttaa ggaccatgtt aaggcgtttg gtctggtca tgggccttat ccaactggtt     900
tgtttgaaga gcaggcttct aattcatctg tctccgagac tttgtttttt taaatttggg     960 catcttttc tttcgcttat gaaatatcta tttactttag aaaataata atgtggtatc    1020 taattgttcc aaattaggaa cacgaagtgt accattatat ttttcatcac tacaaatgtt    1080
attcagagaa aattatcatt aa                                             1102
```

<210> SEQ ID NO 26
<211> LENGTH: 303
<212> TYPE: PRT
<213> ORGANISM: Arabidopsis thaliana

<400> SEQUENCE: 26

```
Met Glu Ser Pro Pro Leu Tyr Glu Ile Ser Ser Ser Ser Ser Glu
1               5                   10                  15

Lys Pro Arg His His Phe Gln Ser Leu Asp Leu Phe Pro Asn Leu Asn
                20                  25                  30

Gln Asn Ser Cys Ile Asn Asn Thr Leu Ile Glu Pro Leu Pro Leu Ile
            35                  40                  45

Asp Arg Ile Asn Leu Asn Ser Asn Leu Asp Leu Asn Pro Asn Pro Leu
        50                  55                  60

Tyr Ala Glu Glu Gly Glu Gln Glu Glu Glu Glu Glu Glu Glu Glu Asp
65                  70                  75                  80

Arg Glu Val Asp Val Asp Leu His Ile Gly Leu Pro Gly Phe Gly Lys
                85                  90                  95

Pro Ser Asn Asp Ala Lys Gln Leu Lys Lys Arg Asn Gly Lys Glu Ile
                100                 105                 110

Ala Thr Tyr Asp Ala Gly Lys Gly Ile Glu Asn Glu Leu Ser Gly Lys
            115                 120                 125

Ala Tyr Trp Ile Pro Ala Pro Glu Gln Ile Leu Ile Gly Phe Thr His
        130                 135                 140

Phe Ser Cys His Val Cys Phe Lys Thr Phe Asn Arg Tyr Asn Asn Leu
145                 150                 155                 160

Gln Met His Met Trp Gly His Gly Ser Gln Tyr Arg Lys Gly Pro Glu
                165                 170                 175

Ser Leu Lys Gly Thr Gln Pro Arg Ala Met Leu Gly Ile Pro Cys Tyr
                180                 185                 190

Cys Cys Val Glu Gly Cys Arg Asn His Ile Asp His Pro Arg Ser Lys
            195                 200                 205

Pro Leu Lys Asp Phe Arg Thr Leu Gln Thr His Tyr Lys Arg Lys His
        210                 215                 220

Gly His Lys Pro Phe Ser Cys Arg Leu Cys Gly Lys Leu Leu Ala Val
225                 230                 235                 240

Lys Gly Asp Trp Arg Thr His Glu Lys Asn Cys Gly Lys Arg Trp Val
                245                 250                 255

Cys Val Cys Gly Ser Asp Phe Lys His Lys Arg Ser Leu Lys Asp His
            260                 265                 270

Val Lys Ala Phe Gly Ser Gly His Gly Pro Tyr Pro Thr Gly Leu Phe
        275                 280                 285

Glu Glu Gln Ala Ser Asn Ser Ser Val Ser Glu Thr Leu Phe Phe
    290                 295                 300
```

<210> SEQ ID NO 27
<211> LENGTH: 1034
<212> TYPE: DNA
<213> ORGANISM: Hordeum vulgare

<400> SEQUENCE: 27

```
atgtcggcgg gcgaggggag gaagacggcg tgcgtcacgg agggagcgg  ctacatcgct      60 tcggcgctca tcaagctgct gctcgagaag ggctacgccg tcaagaccac cgtcagaaac     120
cccgatgaca tggagaagaa ctcccacctc aaagacctgc agcaaacgct tgggcccttg     180
```

```
gagatcatcc gtgccgatct gaatgaagaa ggcagcttcg acgaagctgt ttctggctgc      240
gactacgtct tcctcgtcgc cgctccggtg aacatgttgt ctgaagatcc tgagagagat      300
gtgatcgaac cgcgcgttca aggaacgctc aacgtgatga ggtcgtgcgc gagagcaggc      360
acggtgaagc gcgtgatcct gacgtcgtcg aacgccgggg tgtccaggag gccgctgcag      420
ggcggcggcc acgtgctgga cgagagctcc tggtccgacg tcgagtatct cagagccaac      480
aagccaccaa cttgggcata cggggtgtcg aaggtgcttc tggagaaggc ggcgagcgaa      540
ttcgcggagg agaagggcat cagcctcgtc accgtgttgc ccgtgaccac actgggcgcg      600
gcgccggtcg ccaaagcaag atccagcgtt cccgtcgtcc tctccttgtt gtctggcgac      660
gaagcgcggc tgacaatcct gaaaggcgtg cagtctgtca ccggttccgt gtcgataatt      720
cacgtggagg atctctgccg cgccgaggtg ttcgtcgcgg agaacgagac ctcgtcgggg      780
aggtacatgt gctgcagcca caacaccacc gtcgtgcaga tcacccgtct cctggcagaa      840
aaattcccgc agtacaacgt gaatgcccaa cgattcgctg gatgccccga ggaaccgaga      900
gtgcgcatgt cgtctcagaa gctcgtcgga aagggtttg ccttcaagca tgagtgcctt      960
ggtgagatat tcgatgacgt tgtcgagtat ggaaggagca ccgggatttt gcgccattga     1020
catgttctag atct                                                      1034
```

<210> SEQ ID NO 28
<211> LENGTH: 338
<212> TYPE: PRT
<213> ORGANISM: Hordeum vulgare

<400> SEQUENCE: 28

```
Met Ser Ala Gly Glu Gly Arg Lys Thr Ala Cys Val Thr Gly Gly Ser
1               5                   10                  15

Gly Tyr Ile Ala Ser Ala Leu Ile Lys Leu Leu Leu Glu Lys Gly Tyr
            20                  25                  30

Ala Val Lys Thr Thr Val Arg Asn Pro Asp Met Glu Lys Asn Ser His
        35                  40                  45

Leu Lys Asp Leu Gln Gln Thr Leu Gly Pro Leu Glu Ile Ile Arg Ala
    50                  55                  60

Asp Leu Asn Glu Glu Gly Ser Phe Asp Glu Ala Val Ser Gly Cys Asp
65                  70                  75                  80

Tyr Val Phe Leu Val Ala Ala Pro Val Asn Met Leu Ser Glu Asp Pro
                85                  90                  95

Glu Arg Asp Val Ile Glu Pro Ala Val Gln Gly Thr Leu Asn Val Met
            100                 105                 110

Arg Ser Cys Ala Arg Ala Gly Thr Val Lys Arg Val Ile Leu Thr Ser
        115                 120                 125

Ser Asn Ala Gly Val Ser Arg Arg Pro Leu Gln Gly Gly His Val
    130                 135                 140

Leu Asp Glu Ser Ser Trp Ser Asp Val Glu Tyr Leu Arg Ala Asn Lys
145                 150                 155                 160

Pro Pro Thr Trp Ala Tyr Gly Val Ser Lys Val Leu Leu Glu Lys Ala
                165                 170                 175

Ala Ser Glu Phe Ala Glu Glu Lys Gly Ile Ser Leu Val Thr Val Leu
            180                 185                 190

Pro Val Thr Thr Leu Gly Ala Ala Pro Val Ala Lys Ala Arg Ser Ser
        195                 200                 205

Val Pro Val Val Leu Ser Leu Leu Ser Gly Asp Glu Ala Arg Leu Thr
```

```
              210                 215                 220
Ile Leu Lys Gly Val Gln Ser Val Thr Gly Ser Val Ser Ile Ile His
225                 230                 235                 240

Val Glu Asp Leu Cys Arg Ala Glu Val Phe Val Ala Glu Asn Glu Thr
                245                 250                 255

Ser Ser Gly Arg Tyr Met Cys Cys Ser His Asn Thr Thr Val Val Gln
                260                 265                 270

Ile Thr Arg Leu Leu Ala Glu Lys Phe Pro Gln Tyr Asn Val Asn Ala
                275                 280                 285

Gln Arg Phe Ala Gly Cys Pro Glu Glu Pro Arg Val Arg Met Ser Ser
            290                 295                 300

Gln Lys Leu Val Gly Glu Gly Phe Ala Phe Lys His Glu Cys Leu Gly
305                 310                 315                 320

Glu Ile Phe Asp Asp Val Val Glu Tyr Gly Arg Ser Thr Gly Ile Leu
                325                 330                 335

Arg His

<210> SEQ ID NO 29
<211> LENGTH: 1053
<212> TYPE: DNA
<213> ORGANISM: Hordeum vulgare

<400> SEQUENCE: 29
atggcggcgg cggctggtga tgggacgacg aggaggaaga cggcgtgcgt caccggaggg      60
agcgggtaca tcgcgtcggc tctcgtcaag atgctgctgg agaagggcta cgccgtgaag     120
acgacggtca ggaaccccga tgacggggag aagaacgcgc atctcaagac cctggcggcg     180
ctcggccccc tggaggtctt ccgcgccgac ctgaacgaag agggcagctt cgacgacgcc     240
gtcgccggct cgcgactacgc cttcctcgtc gccgctccgg tggccctcat gccagagaac     300
gccgaggaag aagtgatcca gccggcgatt caaggaaccc tcaacgtgat gaggtcatgc     360
gtgaaggcgg ggacggtgaa gcgcgtggtc ctcacatcgt cgacggccgc gatctccagc     420
cggccgctgg aaggcgacgg ccatgtcctg gacgaggatt cctggtccga cgtcgagtac     480
ctcagggcca ccaagagcgg tacctgggcg taccctgcct cgaaggtgct ggcggagaag     540
gcggcgatgg cgctcgcgga ggagaagggc ctcagcctgg tgaccgtgtg ccccgtggtc     600
gtcgtcggcg gggcaccggt cagcaaggtc aagaccagcg tccccgaggt cctctccttg     660
ctctccggcg acgacgacat ggtggacaac ctggagctca tcgagaaggc atcggggtcg     720
atcccgctgg tgcacatcga cgacgtgagc cgcgccgaga tattcgccgc gaggaggcc      780 acgtcggggc ggtacatcgt gtgcaccctc aacaccaccg ccgtggcgct cgcccacttc     840
ctggcggcca gtacccgca gtacgagatc aacgacgacc gcattggtca tcttccggag     900
aagccgaggg tgagcatctg gtcggacaag ctcatcaagg aggggttcga gtacaagtac     960
aagaacctgg acgagatata cgacgacctc gtcgtctacg caggaccct gggactcctt    1020 aaatactgat ataacaggct cttctctaga tct                                 1053

<210> SEQ ID NO 30
<211> LENGTH: 342
<212> TYPE: PRT
<213> ORGANISM: Hordeum vulgare

<400> SEQUENCE: 30

Met Ala Ala Ala Ala Gly Asp Gly Thr Thr Arg Arg Lys Thr Ala Cys
1               5                   10                  15
```

Val Thr Gly Gly Ser Gly Tyr Ile Ala Ser Ala Leu Val Lys Met Leu
         20                  25                  30

Leu Glu Lys Gly Tyr Ala Val Lys Thr Thr Val Arg Asn Pro Asp Asp
         35                  40                  45

Gly Glu Lys Asn Ala His Leu Lys Thr Leu Ala Ala Leu Gly Pro Leu
 50                  55                  60

Glu Val Phe Arg Ala Asp Leu Asn Glu Glu Gly Ser Phe Asp Asp Ala
 65                  70                  75                  80

Val Ala Gly Cys Asp Tyr Ala Phe Leu Val Ala Ala Pro Val Ala Leu
                 85                  90                  95

Met Pro Glu Asn Ala Glu Glu Val Ile Gln Pro Ala Ile Gln Gly
                 100                 105                 110

Thr Leu Asn Val Met Arg Ser Cys Val Lys Ala Gly Thr Val Lys Arg
         115                 120                 125

Val Val Leu Thr Ser Ser Thr Ala Ala Ile Ser Ser Arg Pro Leu Glu
 130                 135                 140

Gly Asp Gly His Val Leu Asp Glu Asp Ser Trp Ser Asp Val Glu Tyr
145                 150                 155                 160

Leu Arg Ala Thr Lys Ser Gly Thr Trp Ala Tyr Pro Ala Ser Lys Val
                 165                 170                 175

Leu Ala Glu Lys Ala Ala Met Ala Leu Ala Glu Lys Gly Leu Ser
                 180                 185                 190

Leu Val Thr Val Cys Pro Val Val Val Gly Gly Ala Pro Val Ser
         195                 200                 205

Lys Val Lys Thr Ser Val Pro Glu Val Leu Ser Leu Leu Ser Gly Asp
210                 215                 220

Asp Asp Met Val Asp Asn Leu Glu Leu Ile Glu Lys Ala Ser Gly Ser
225                 230                 235                 240

Ile Pro Leu Val His Ile Asp Asp Val Ser Arg Ala Glu Ile Phe Ala
                 245                 250                 255

Ala Glu Glu Ala Thr Ser Gly Arg Tyr Ile Val Cys Thr Leu Asn Thr
                 260                 265                 270

Thr Ala Val Ala Leu Ala His Phe Leu Ala Ala Lys Tyr Pro Gln Tyr
         275                 280                 285

Glu Ile Asn Asp Asp Arg Ile Gly His Leu Pro Glu Lys Pro Arg Val
         290                 295                 300

Ser Ile Trp Ser Asp Lys Leu Ile Lys Glu Gly Phe Glu Tyr Lys Tyr
305                 310                 315                 320

Lys Asn Leu Asp Glu Ile Tyr Asp Asp Leu Val Val Tyr Gly Arg Thr
                 325                 330                 335

Leu Gly Leu Leu Lys Tyr
         340

<210> SEQ ID NO 31
<211> LENGTH: 1053
<212> TYPE: DNA
<213> ORGANISM: Hordeum vulgare
<220> FEATURE:
<221> NAME/KEY: modified_base
<222> LOCATION: (1022)..(1022)
<223> OTHER INFORMATION: n = a, c, g or t/u
<220> FEATURE:
<221> NAME/KEY: misc_feature
<222> LOCATION: (1022)..(1022)
<223> OTHER INFORMATION: n is a, c, g, or t

<400> SEQUENCE: 31

```
atggcggcgg cggctggtga tgggacgacg aggaggaaga cggcgtgcgt caccggaggg     60
agcgggtaca tcgcgtcggc tctcgtcaag atgctgctgg agaagggcta cgccgtgaag    120
acgacggtca ggaaccccga tgacggggag aagaacgcgc atctcaagac cctggcggcg    180
ctcggccccc tggaggtctt ccgcgccgac ctgaacgaag agggcagctt cgacgacgcc    240
gtcgccggct gcgactacgc cttcctcgtc gccgctccgg tggccctcat gccagagaac    300
gccgaggaag aagtgatcca gccggcgatt caaggaaccc tcaacgtgat gaggtcgtgc    360
gtgaaggcgg gacggtgaa gcgcgtggtc ctcacatcgt cgacggccgc gatctccagc    420
cggccgctgg aaggcgacgg ccatgtcctg gacgaggatt cctggtccga cgtcgagtac    480
ctcagggcca ccaagagcgg tacctgggcg taccctgcct cgaaggtgct ggcggagaag    540
gcggcgatgg cgttcgcgga ggagaatggc ctcagcctgg tgaccgtgtg ccccgtggtc    600
gtcgtcggcg gggcaccggc cagcaaggtc aagaccagcg tccccgaggt cctctccttg    660
ctctccggcg acgacgacat ggtggacaac ctggagctca tcgagaaggc gacggggtcg    720
atcccgctgg tgcacatcga cgacgtgagc cgcgccgaga tattcgccga cgaagaggcc    780
aaatcggggc ggtacatcgt gtgcaccctc aacaccaccg ccgtggcgct cgcccacttc    840
ctggcggcca gtacccgca gtacgagatc aacgacgacc gcattggtca tcttccggag    900
aagccgaggg tgagcatctg gtcggacaag ctcatcaagg aggggttcga atacaagtac    960
aagaacctgg acgagatata cgacgacctc gtcgtctacg gcaggaccct gggactcctt   1020
anatactgat ataacaggct cttctctaga tct                                1053
```

<210> SEQ ID NO 32
<211> LENGTH: 342
<212> TYPE: PRT
<213> ORGANISM: Hordeum vulgare
<220> FEATURE:
<221> NAME/KEY: MOD_RES
<222> LOCATION: (341)..(341)
<223> OTHER INFORMATION: x = any natural occurring amino acid

<400> SEQUENCE: 32

Met Ala Ala Ala Gly Asp Gly Thr Thr Arg Arg Lys Thr Ala Cys
1               5                   10                  15

Val Thr Gly Gly Ser Gly Tyr Ile Ala Ser Ala Leu Val Lys Met Leu
            20                  25                  30

Leu Glu Lys Gly Tyr Ala Val Lys Thr Thr Val Arg Asn Pro Asp Asp
        35                  40                  45

Gly Glu Lys Asn Ala His Leu Lys Thr Leu Ala Ala Leu Gly Pro Leu
    50                  55                  60

Glu Val Phe Arg Ala Asp Leu Asn Glu Glu Gly Ser Phe Asp Asp Ala
65                  70                  75                  80

Val Ala Gly Cys Asp Tyr Ala Phe Leu Val Ala Pro Val Ala Leu
                85                  90                  95

Met Pro Glu Asn Ala Glu Glu Val Ile Gln Pro Ala Ile Gln Gly
            100                 105                 110

Thr Leu Asn Val Met Arg Ser Cys Val Lys Ala Gly Thr Val Lys Arg
        115                 120                 125

Val Val Leu Thr Ser Ser Thr Ala Ala Ile Ser Ser Arg Pro Leu Glu
    130                 135                 140

Gly Asp Gly His Val Leu Asp Glu Asp Ser Trp Ser Asp Val Glu Tyr
145                 150                 155                 160

```
Leu Arg Ala Thr Lys Ser Gly Thr Trp Ala Tyr Pro Ala Ser Lys Val
                165                 170                 175

Leu Ala Glu Lys Ala Ala Met Ala Phe Ala Glu Glu Asn Gly Leu Ser
            180                 185                 190

Leu Val Thr Val Cys Pro Val Val Val Gly Gly Ala Pro Ala Ser
        195                 200                 205

Lys Val Lys Thr Ser Val Pro Glu Val Leu Ser Leu Leu Ser Gly Asp
    210                 215                 220

Asp Asp Met Val Asp Asn Leu Glu Leu Ile Glu Lys Ala Thr Gly Ser
225                 230                 235                 240

Ile Pro Leu Val His Ile Asp Asp Val Ser Arg Ala Glu Ile Phe Ala
                245                 250                 255

Asp Glu Glu Ala Lys Ser Gly Arg Tyr Ile Val Cys Thr Leu Asn Thr
            260                 265                 270

Thr Ala Val Ala Leu Ala His Phe Leu Ala Ala Lys Tyr Pro Gln Tyr
        275                 280                 285

Glu Ile Asn Asp Asp Arg Ile Gly His Leu Pro Glu Lys Pro Arg Val
    290                 295                 300

Ser Ile Trp Ser Asp Lys Leu Ile Lys Glu Gly Phe Glu Tyr Lys Tyr
305                 310                 315                 320

Lys Asn Leu Asp Glu Ile Tyr Asp Asp Leu Val Val Tyr Gly Arg Thr
                325                 330                 335

Leu Gly Leu Leu Xaa Tyr
            340
```

<210> SEQ ID NO 33
<211> LENGTH: 1034
<212> TYPE: DNA
<213> ORGANISM: Hordeum vulgare

<400> SEQUENCE: 33

```
atgtcggcgg gcgaggggag gaagacggcg tgcgtcacgg agggagcgg  ctacatcgct      60
tcggcgctca tcaagctgct gctcgagaag ggctacgccg tcaagaccac cgtcagaaac     120
cccgatgaca tggagaagaa ctcccacctc aaagacctgc agcaaacgct tgggcccttg     180
gagatcatcc gtgccgatct gaatgaagaa ggcagcttcg acgaagctgt ttctggctgc     240
gactacgtct tcctcgttgc cgctccggtg aacatgttgt ctgaagatcc tgagagagat     300
gtgatcgaac ccgctgtgca aggaacgctc aacgtgatga ggtcgtgcgc gagagcaggc     360
acggtgaagc gcgtgatcct gacgtcgtcg aacgccgggg tgtccaggag gccgctgcag     420
ggcggcggcc acgtgctgga cgagagctcc tggtccgacg tcgagtatct cagagccaac     480
aagccaccaa cttgggcata cggggtgtcg aaggtgcttc tggagaaggc ggcgagcgaa     540
ttcgcggagg agaagggcat cagcctcgtc accgtgttgc ccgtgaccac actgggcgcg     600
gcgccggtcg ccaaagcaag atccagcgtt cccgtcgtcc tctccttgtt gtctggcgac     660
gaagcgcggc tgacaatcct gaaaggcgtg cagtctgtca ccggttccgt gtcgataatt     720
cacgtggagg atctctgccg cgccgaggtg ttcgtcgcgg agaacgagac ctcgtcgggg     780
aggtacatgt gctgcagcca caactccacc gtcgtgcaga tcaccgtcct tctggcggaa     840
aaattcccgc agtacaacgt gaatgcccaa cgattgctg  gatgccccga ggaaccgaga     900
gtgcgcatgt cgtctcagaa gctcgtcgga gaagggtttg tcttcaagca tgagtgcctt     960
ggtgagatat tcgatgacgt tgtcgagtat ggaaggagca ccgggatttt gcgccattga    1020
catgttctag atct                                                      1034
```

<210> SEQ ID NO 34
<211> LENGTH: 288
<212> TYPE: PRT
<213> ORGANISM: Hordeum vulgare

<400> SEQUENCE: 34

Met Ser Ala Gly Glu Gly Arg Lys Thr Ala Cys Val Thr Gly Gly Ser
1               5                   10                  15

Gly Tyr Ile Ala Ser Ala Leu Ile Lys Leu Leu Leu Glu Lys Gly Tyr
            20                  25                  30

Ala Val Lys Thr Thr Val Arg Asn Pro Asp Asp Met Glu Lys Asn Ser
        35                  40                  45

His Leu Lys Asp Leu Gln Gln Thr Leu Gly Pro Leu Glu Ile Ile Arg
    50                  55                  60

Ala Asp Leu Asn Glu Glu Gly Ser Phe Asp Glu Ala Val Ser Gly Cys
65                  70                  75                  80

Asp Tyr Val Phe Leu Val Ala Ala Pro Val Asn Met Leu Ser Glu Asp
                85                  90                  95

Pro Glu Arg Asp Val Ile Glu Pro Ala Val Gln Gly Thr Leu Asn Val
            100                 105                 110

Met Arg Ser Cys Ala Arg Ala Gly Thr Val Lys Arg Val Ile Leu Thr
        115                 120                 125

Ser Ser Asn Ala Gly Val Ser Arg Arg Pro Leu Gln Gly Gly Gly His
    130                 135                 140

Val Leu Asp Glu Ser Ser Trp Ser Asp Val Glu Tyr Leu Arg Ala Asn
145                 150                 155                 160

Lys Pro Pro Thr Trp Ala Tyr Gly Val Ser Lys Val Leu Leu Glu Lys
                165                 170                 175

Ala Ala Ser Glu Phe Ala Glu Glu Lys Gly Ile Ser Leu Val Thr Val
            180                 185                 190

Leu Pro Val Thr Thr Leu Gly Ala Ala Pro Val Ala Lys Ala Arg Ser
        195                 200                 205

Ser Val Pro Val Val Leu Ser Leu Leu Ser Gly Asp Glu Ala Arg Leu
    210                 215                 220

Thr Ile Leu Lys Gly Val Gln Ser Val Thr Gly Ser Val Ser Ile Ile
225                 230                 235                 240

His Val Glu Asp Leu Cys Arg Ala Glu Val Phe Val Ala Glu Asn Glu
                245                 250                 255

Thr Ser Ser Gly Arg Tyr Met Cys Cys Ser His Asn Ser Thr Val Val
            260                 265                 270

Gln Ile Thr Arg Leu Leu Ala Glu Lys Phe Pro Gln Tyr Asn Val Asn
        275                 280                 285

<210> SEQ ID NO 35
<211> LENGTH: 780
<212> TYPE: DNA
<213> ORGANISM: Brassica napus

<400> SEQUENCE: 35
atcttccatg tcgcaactcc aatcagcttt acatctcaag atcccgaggt caaggtccta      60
aacatatatg tgcatgcttt ttatataaac attttgaatt atcttgtttg tgtttaaata     120
aatgtacaga aagacatgat caaaccagcg gtacaaggag tgatcaacgt gttgaaatct     180
tgcttaaaat cgaactcaat caagcgcgtg atctacactt cttcagctgc tgcggtttct     240

```
atcaacaacc tttcggaacc tggacttgtg atgaccgaag aaaactggtc tgacgttgat      300
tttctcacaa aggagaagcc gtttaactgg gtaataacaa tttcttgctg cacaagatag      360 gttttttcc cgactaagtt cagttacctc tctctgtttt atttctaggg ttacccagtc       420
tcaaagactt tagcagaaaa ggaagcttat aaatttgcgg aagagaataa gattgatctc      480
gttactgtgg ttccagcact catagccgga aactctctcc tctctgatcc tccgagcagt      540
ttatctctct cgatgtcttt aatcactggt aaacatgaat cataatacta tttgaccact      600
tctgttaaag tttcacaatc aagatgattg ttttttgttg ttagggaaag aaatgcatct      660
gagcggtctc aaggaaatgc agaagctatc tggatccatc tcgttcatcc acgtggacga      720
cctagctcgt gcacatatgt ttcttgcgga gaaagaaaca gcttctggtc gctacatttg      780
```

<210> SEQ ID NO 36
<211> LENGTH: 181
<212> TYPE: PRT
<213> ORGANISM: Brassica napus

<400> SEQUENCE: 36

```
Ile Phe His Val Ala Thr Pro Ile Ser Phe Thr Ser Gln Asp Pro Glu
  1               5                  10                  15

Lys Asp Met Ile Lys Pro Ala Val Gln Gly Val Ile Asn Val Leu Lys
                 20                  25                  30

Ser Cys Leu Lys Ser Asn Ser Ile Lys Arg Val Ile Tyr Thr Ser Ser
             35                  40                  45

Ala Ala Ala Val Ser Ile Asn Asn Leu Ser Glu Pro Gly Leu Val Met
         50                  55                  60

Thr Glu Glu Asn Trp Ser Asp Val Asp Phe Leu Thr Lys Glu Lys Pro
 65                  70                  75                  80

Phe Asn Trp Gly Tyr Pro Val Ser Lys Thr Leu Ala Glu Lys Glu Ala
                 85                  90                  95

Tyr Lys Phe Ala Glu Glu Asn Lys Ile Asp Leu Val Thr Val Val Pro
                100                 105                 110

Ala Leu Ile Ala Gly Asn Ser Leu Leu Ser Asp Pro Pro Ser Ser Leu
            115                 120                 125

Ser Leu Ser Met Ser Leu Ile Thr Gly Lys Glu Met His Leu Ser Gly
        130                 135                 140

Leu Lys Glu Met Gln Lys Leu Ser Gly Ser Ile Ser Phe Ile His Val
145                 150                 155                 160

Asp Asp Leu Ala Arg Ala His Met Phe Leu Ala Glu Lys Glu Thr Ala
                165                 170                 175

Ser Gly Arg Tyr Ile
            180
```

<210> SEQ ID NO 37
<211> LENGTH: 964
<212> TYPE: DNA
<213> ORGANISM: Gossypium arboreum

<400> SEQUENCE: 37

```
atggccagcc agctcgtagg aacaaagaga gcttgtgtcg tgggtggcag cggattcgtt      60
gcgtcattgc tggtcaagtt gttgctcgaa gatctctcac cttgtaacac tacaagagtt     120
gggagacttg aagatctttc aggcggattt aactgatgaa gggagctttg atgcccctat     180
tgctggttgt gaccttgtct tccatgttgc gacacccgtt aactttgctt ctgaagatcc     240
agagaatgac atgatcaaac cagcgactca aggagtggtg aacgttttga aagcttgtgc     300
```

-continued

```
caaagcaaaa acagttaaac gagtggtctt gacatctcgt catgacagag aaagactgga      360
ccgatatcga gttcttatca tcagcaaagc caccaacttg ggggtaccct gcatccaaga      420
cgttggctga aaaggcagct tggaaatttg ctgaagaaaa caacattgat ctcattacag      480
ttatcccttc tctcatgact ggtccttccc tcaccccaat tgtccccagc agcataggcc      540
ttgctacatc tttgatttca ggcaatgaat tcctcataaa tgctttgaaa ggaatgcaga      600
tgctgtcagg ttcgatctct atcacacatg tggaagacgt atgccgagcc catgtttttc      660
tggctgaaaa agaatctgca tcgggtcgat atatatgcag tgctgtcaat accagtgtgc      720
cagaactagc aaagttcctc aacaaaagat accctgactt caaagtccct accgattttg      780
gagatttccc ctccaaaccc aagttgatca tttcctcaga gaagcttatt agcgaaggat      840
tcagctttaa gtatgggatc gaggaaatct acgaccaaac cgtggaatat ttgaagtcta      900 agggctgct caagtgaagc gctctgacgc ttccccaatg attatggtgt ttgactctag      960
atct                                                                  964
```

<210> SEQ ID NO 38
<211> LENGTH: 338
<212> TYPE: PRT
<213> ORGANISM: Gossypium arboreum

<400> SEQUENCE: 38

```
Met Ala Ser Gln Leu Val Gly Thr Lys Arg Ala Cys Val Val Gly Gly
1               5                   10                  15

Ser Gly Phe Val Ala Ser Leu Leu Val Lys Leu Leu Leu Glu Lys Gly
                20                  25                  30

Phe Ala Val Asn Thr Thr Val Arg Asp Pro Asp Asn Gln Lys Lys Ile
            35                  40                  45

Ser His Leu Val Thr Leu Gln Glu Leu Gly Asp Leu Lys Ile Phe Gln
        50                  55                  60

Ala Asp Leu Thr Asp Glu Gly Ser Phe Asp Ala Pro Ile Ala Gly Cys
65                  70                  75                  80

Asp Leu Val Phe His Val Ala Thr Pro Val Asn Phe Ala Ser Glu Asp
                85                  90                  95

Pro Glu Asn Asp Met Glu Thr Ile Lys Pro Ala Thr Gln Gly Val Val
            100                 105                 110

Asn Val Leu Lys Ala Cys Ala Lys Ala Lys Thr Val Lys Arg Val Val
        115                 120                 125

Leu Thr Ser Ser Ala Ala Ala Val Ser Ile Asn Thr Leu Asp Gly Thr
    130                 135                 140

Asp Leu Val Met Thr Glu Lys Asp Trp Thr Asp Ile Glu Phe Leu Ser
145                 150                 155                 160

Ser Ala Lys Pro Pro Thr Trp Gly Tyr Pro Ala Ser Lys Thr Leu Ala
                165                 170                 175

Glu Lys Ala Ala Trp Lys Phe Ala Glu Glu Asn Asn Ile Asp Leu Ile
            180                 185                 190

Thr Val Ile Pro Ser Leu Met Thr Gly Pro Ser Leu Thr Pro Ile Val
        195                 200                 205

Pro Ser Ser Ile Gly Leu Ala Thr Ser Leu Ile Ser Gly Asn Glu Phe
    210                 215                 220

Leu Ile Asn Ala Leu Lys Gly Met Gln Met Leu Ser Gly Ser Ile Ser
225                 230                 235                 240

Ile Thr His Val Glu Asp Val Cys Arg Ala His Val Phe Leu Ala Glu
```

```
                    245                 250                 255
Lys Glu Ser Ala Ser Gly Arg Tyr Ile Cys Ser Ala Val Asn Thr Ser
                260                 265                 270

Val Pro Glu Leu Ala Lys Phe Leu Asn Lys Arg Tyr Pro Asp Phe Lys
            275                 280                 285

Val Pro Thr Asp Phe Gly Asp Phe Pro Ser Lys Pro Lys Leu Ile Ile
        290                 295                 300

Ser Ser Glu Lys Leu Ile Ser Glu Gly Phe Ser Phe Lys Tyr Gly Ile
305                 310                 315                 320

Glu Glu Ile Tyr Asp Gln Thr Val Glu Tyr Leu Lys Ser Lys Gly Leu
                325                 330                 335

Leu Lys

<210> SEQ ID NO 39
<211> LENGTH: 1016
<212> TYPE: DNA
<213> ORGANISM: Vitis vinifera

<400> SEQUENCE: 39
atggccaccc agcaccccat cggaaagaag accgcatgtg tcgtcggcgg caccggattt      60
gttgcatctt tgctggttaa gcttttgctg cagaagggct atgctgtcaa caccactgtc     120
agggaccctg acaatcagaa aaaagtctct cacctcctag aactacagga gttgggtgac     180
ctaaaaatct tcgagcagat ctaactgac gaattgagct ttgaggcccc tatagcaggt     240
tgcgactttg tcttccatgt tgctacgccc gtccactttg cttctgaaga tccagagaat     300
gacatgatca agccagcaat tcaaggagta gtgaatgtca tgaaagcttg tacaagggca     360
aaaatcagtt aacgagtcat tttgacatcc tctgcagctg ctgttaccat caatcagctt     420
gatgggacag gtctggttgt ggatgagaag aactggactg atattgagtt cttgacttcc     480
gcgaagccac ctacttgggg ctatcctgcc tccaagacac tagctgagaa gcagcttgg     540 aaatttgccg aagaaaataa cattgatctg atcactgtca tccctactct gatggccggt     600
tcctctctta cttcagatgt ccccagcagc attggacttg caatgtcctt gattacaggg     660
aatgaattcc tcataaacgg tatgaagggt atgcagatgc tgtcaggttc agtctccatt     720
gcacatgtgg aagatgtttg ccaggcacat atatttgtag ctgagaaaga tcagcttct     780 ggccgataca tctgctgtgc tgccaatacc agtgttcctg agctagcaaa gttcctgagc     840
aaaagatacc ctcagtacaa agtcccaact gattttggag acttcccccc taaatcgaag     900
ttgataatct cctcagagaa gcttgtgaaa gaggggttca gttttaagta cgggattgaa     960
gaaatttatg atgaaagtgt ggagtatttc aaggccaagg ggctattgca gaattg       1016

<210> SEQ ID NO 40
<211> LENGTH: 338
<212> TYPE: PRT
<213> ORGANISM: Vitis vinifera

<400> SEQUENCE: 40

Met Ala Thr Gln His Pro Ile Gly Lys Lys Thr Ala Cys Val Val Gly
1               5                   10                  15

Gly Thr Gly Phe Val Ala Ser Leu Leu Val Lys Leu Leu Leu Gln Lys
            20                  25                  30

Gly Tyr Ala Val Asn Thr Thr Val Arg Asp Pro Asp Asn Gln Lys Lys
        35                  40                  45

Val Ser His Leu Leu Glu Leu Gln Glu Leu Gly Asp Leu Lys Ile Phe
```

```
            50                  55                  60
Arg Ala Asp Leu Thr Asp Glu Leu Ser Phe Glu Ala Pro Ile Ala Gly
 65                  70                  75                  80

Cys Asp Phe Val Phe His Val Ala Thr Pro Val His Phe Ala Ser Glu
                 85                  90                  95

Asp Pro Glu Asn Asp Met Ile Lys Pro Ala Ile Gln Gly Val Val Asn
            100                 105                 110

Val Met Lys Ala Cys Thr Arg Ala Lys Ser Val Lys Arg Val Ile Leu
        115                 120                 125

Thr Ser Ser Ala Ala Val Thr Ile Asn Gln Leu Asp Gly Thr Gly
    130                 135                 140

Leu Val Val Asp Glu Lys Asn Trp Thr Asp Ile Glu Phe Leu Thr Ser
145                 150                 155                 160

Ala Lys Pro Pro Thr Trp Gly Tyr Pro Ala Ser Lys Thr Leu Ala Glu
                165                 170                 175

Lys Ala Ala Trp Lys Phe Ala Glu Glu Asn Asn Ile Asp Leu Ile Thr
            180                 185                 190

Val Ile Pro Thr Leu Met Ala Gly Ser Ser Leu Thr Ser Asp Val Pro
        195                 200                 205

Ser Ser Ile Gly Leu Ala Met Ser Leu Ile Thr Gly Asn Glu Phe Leu
    210                 215                 220

Ile Asn Gly Met Lys Gly Met Gln Met Leu Ser Gly Ser Val Ser Ile
225                 230                 235                 240

Ala His Val Glu Asp Val Cys Gln Ala His Ile Phe Val Ala Glu Lys
                245                 250                 255

Glu Ser Ala Ser Gly Arg Tyr Ile Cys Cys Ala Ala Asn Thr Ser Val
            260                 265                 270

Pro Glu Leu Ala Lys Phe Leu Ser Lys Arg Tyr Pro Gln Tyr Lys Val
        275                 280                 285

Pro Thr Asp Phe Gly Asp Phe Pro Pro Lys Ser Lys Leu Ile Ile Ser
    290                 295                 300

Ser Glu Lys Leu Val Lys Glu Gly Phe Ser Phe Lys Tyr Gly Ile Glu
305                 310                 315                 320

Glu Ile Tyr Asp Glu Ser Val Glu Tyr Phe Lys Ala Lys Gly Leu Leu
                325                 330                 335

Gln Asn

<210> SEQ ID NO 41
<211> LENGTH: 777
<212> TYPE: DNA
<213> ORGANISM: Arabidopsis thaliana

<400> SEQUENCE: 41
atgggaaaga gagcaactac tagtgtgagg agagaagagt taaacagagg agcttggact      60
gatcatgaag acaagatcct tagagattac atcaccactc acggcgaagg caaatggagc     120
actctcccta accaagctgg tctcaagagg tgtggcaaaa gctgtagact tcggtggaag     180
aactacctaa gaccggggat aaagcgcggt aacatctcat ctgatgaaga gaactcata      240 atccgtctcc ataatcttct tggaaacaga tggtcgttga tagctgggag gcttccaggc     300
cgaacagaca atgaaataaa gaatcattgg aactcaaacc tccgcaaaag acttcccaaa     360
actcaaacca gcaaccaaa acgtataaaa cattcgacga caacgagaa taatgtatgt       420 gttatacgta caaaggcgat taggtgctca agactcttc tcttctcgga tctctctctt      480
```

```
cagaagaaga gtagtactag tccactacct ctgaaagaac aagagatgga tcaaggtgga      540
tcttcgttga tgggagatct cgaattcgat ttcgatagga tccattcgga gtttcacttc      600
ccggatttga tggattttga tggtttggac tgtggaaacg ttacatctct tgtttcatct      660
aacgagattt tgggagagtt ggttcctgct caaggtaatc tcgatctcaa tagaccttct      720
acttcttgtc atcatcgtgg cgacgatgaa gattggctcc gagacttcac ttgttga        777
```

<210> SEQ ID NO 42
<211> LENGTH: 258
<212> TYPE: PRT
<213> ORGANISM: Arabidopsis thaliana

<400> SEQUENCE: 42

```
Met Gly Lys Arg Ala Thr Thr Ser Val Arg Arg Glu Glu Leu Asn Arg
1               5                   10                  15

Gly Ala Trp Thr Asp His Glu Asp Lys Ile Leu Arg Asp Tyr Ile Thr
            20                  25                  30

Thr His Gly Glu Gly Lys Trp Ser Thr Leu Pro Asn Gln Ala Gly Leu
        35                  40                  45

Lys Arg Cys Gly Lys Ser Cys Arg Leu Arg Trp Lys Asn Tyr Leu Arg
    50                  55                  60

Pro Gly Ile Lys Arg Gly Asn Ile Ser Ser Asp Glu Glu Leu Ile
65                  70                  75                  80

Ile Arg Leu His Asn Leu Leu Gly Asn Arg Trp Ser Leu Ile Ala Gly
                85                  90                  95

Arg Leu Pro Gly Arg Thr Asp Asn Glu Ile Lys Asn His Trp Asn Ser
            100                 105                 110

Asn Leu Arg Lys Arg Leu Pro Lys Thr Gln Thr Lys Gln Pro Lys Arg
        115                 120                 125

Ile Lys His Ser Thr Asn Asn Glu Asn Asn Val Cys Val Ile Arg Thr
    130                 135                 140

Lys Ala Ile Arg Cys Ser Lys Thr Leu Leu Phe Ser Asp Leu Ser Leu
145                 150                 155                 160

Gln Lys Lys Ser Ser Thr Ser Pro Leu Pro Leu Lys Glu Gln Glu Met
                165                 170                 175

Asp Gln Gly Gly Ser Ser Leu Met Gly Asp Leu Glu Phe Asp Phe Asp
            180                 185                 190

Arg Ile His Ser Glu Phe His Phe Pro Asp Leu Met Asp Phe Asp Gly
        195                 200                 205

Leu Asp Cys Gly Asn Val Thr Ser Leu Val Ser Ser Asn Glu Ile Leu
    210                 215                 220

Gly Glu Leu Val Pro Ala Gln Gly Asn Leu Asp Leu Asn Arg Pro Phe
225                 230                 235                 240

Thr Ser Cys His His Arg Gly Asp Asp Glu Asp Trp Leu Arg Asp Phe
                245                 250                 255

Thr Cys
```

<210> SEQ ID NO 43
<211> LENGTH: 1017
<212> TYPE: DNA
<213> ORGANISM: Medicago truncatula

<400> SEQUENCE: 43

```
atggctagta tcaaacaaat agaaatagaa aagaagaagg catgtgtgat aggtggcact       60
ggttttgtgg catcattgct gatcaagcag ttgcttgaaa agggttatgc tgttaatact      120
```

```
actgttagag acctagatag tgcaaacaaa acatctcacc tcatagcact gcaaagtttg      180
ggggaactga atctatttaa agcagaatta acaattgaag aagattttga tgctcctata      240
tcaggatgtg aacttgtctt ccaacttgct acacctgtga actttgcttc tcaagatcct      300
gagaatgaca tgataaaacc agcaatcaaa ggtgtattga atgtgttgaa agcatgtgta      360
agagcaaaag aagtcaaaag agttatctta acatcttcag cagctgctgt gactataaac      420
gaactcgaag ggactggtca tgttatggat gaaaccaatt ggtctgatgt tgagttttg       480 aacactgcaa agccacccac ttgggggttat cctgtttcaa agtactagc tgaaaaggct      540 gcgtggaaat tgctgaaga aaataacatt gatctaatca ctgtgatacc tactctaaca      600
attggtcctt ctctaactca agatatccca tctagtgttg ccatgggaat gtcacttcta      660
acaggcaatg atttcctcat aaatgctttg aaaggaatgc agtttctatc gggttcaata      720
tcaattactc atgtcgagga tatttgtcgg gctcatattt ttgtggcaga gaaagaatca      780
acttctggtc gatacatttg ctgtgctcac aataccagtg ttcccgagct tgcaaagttt      840
ctcagcaaac gataccctca gtataaagtt ccaactgaat tgatgatttt ccccagcaag      900
gcaaagttga taatctcttc tggaaagctt atcaaagaag gtttcagttt caagcatagt      960
attgctgaaa cttttgacca aactgtggag tatttgaaga ctcaggggat caagtga       1017
```

<210> SEQ ID NO 44
<211> LENGTH: 338
<212> TYPE: PRT
<213> ORGANISM: Medicago truncatula

<400> SEQUENCE: 44

```
Met Ala Ser Ile Lys Gln Ile Glu Ile Glu Lys Lys Ala Cys Val
1               5                   10                  15

Ile Gly Gly Thr Gly Phe Val Ala Ser Leu Leu Ile Lys Gln Leu Leu
                20                  25                  30

Glu Lys Gly Tyr Ala Val Asn Thr Thr Val Arg Asp Leu Asp Ser Ala
            35                  40                  45

Asn Lys Thr Ser His Leu Ile Ala Leu Gln Ser Leu Gly Glu Leu Asn
        50                  55                  60

Leu Phe Lys Ala Glu Leu Thr Ile Glu Glu Asp Phe Asp Ala Pro Ile
65                  70                  75                  80

Ser Gly Cys Glu Leu Val Phe Gln Leu Ala Thr Pro Val Asn Phe Ala
                85                  90                  95

Ser Gln Asp Pro Glu Asn Asp Met Ile Lys Pro Ala Ile Lys Gly Val
            100                 105                 110

Leu Asn Val Leu Lys Ala Cys Val Arg Ala Lys Glu Val Lys Arg Val
        115                 120                 125

Ile Leu Thr Ser Ser Ala Ala Ala Val Thr Ile Asn Glu Leu Glu Gly
    130                 135                 140

Thr Gly His Val Met Asp Glu Thr Asn Trp Ser Asp Val Glu Phe Leu
145                 150                 155                 160

Asn Thr Ala Lys Pro Pro Thr Trp Gly Tyr Pro Val Ser Lys Val Leu
                165                 170                 175

Ala Glu Lys Ala Ala Trp Lys Phe Ala Glu Glu Asn Asn Ile Asp Leu
            180                 185                 190

Ile Thr Val Ile Pro Thr Leu Thr Ile Gly Pro Ser Leu Thr Gln Asp
        195                 200                 205

Ile Pro Ser Ser Val Ala Met Gly Met Ser Leu Leu Thr Gly Asn Asp
```

```
                    210                 215                 220
Phe Leu Ile Asn Ala Leu Lys Gly Met Gln Phe Leu Ser Gly Ser Ile
225                 230                 235                 240

Ser Ile Thr His Val Glu Asp Ile Cys Arg Ala His Ile Phe Val Ala
                245                 250                 255

Glu Lys Glu Ser Thr Ser Gly Arg Tyr Ile Cys Cys Ala His Asn Thr
                260                 265                 270

Ser Val Pro Glu Leu Ala Lys Phe Leu Ser Lys Arg Tyr Pro Gln Tyr
                275                 280                 285

Lys Val Pro Thr Glu Phe Asp Asp Phe Pro Ser Lys Ala Lys Leu Ile
290                 295                 300

Ile Ser Ser Gly Lys Leu Ile Lys Glu Gly Phe Ser Phe Lys His Ser
305                 310                 315                 320

Ile Ala Glu Thr Phe Asp Gln Thr Val Glu Tyr Leu Lys Thr Gln Gly
                325                 330                 335

Ile Lys

<210> SEQ ID NO 45
<211> LENGTH: 1213
<212> TYPE: DNA
<213> ORGANISM: Arabidopsis thaliana

<400> SEQUENCE: 45
caataacaac taaatctcta tctctgtaat ttcaaaagta caatcatgga ccagactctt      60
acacacaccg gatcgaagaa ggcttgtgtc attggtggca cgggaaactt agcctctatt     120
ctcatcaagc atttgcttca aagtggctac aaagttaaca ctacagttag agatccagaa     180
aacgagaaga aaatagctca ccttaggcaa cttcaagaac ttggcgacct gaagatcttc     240
aaggcagatt tgactgatga agacagtttc gaatcctcat tctccggctg tgaatacatc     300
ttccatgtcg caactccgat caactttaaa tccgaagatc ccgagaaaga catgatcaag     360
ccggcgatac aaggagtgat caatgtgttg aaatcttgct taaaatcgaa atcagtcaag     420
cgtgtgatct acacatcttc agctgctgct gtttccatca acaatctttc tggaaccgga     480
ctcgtgatga acgaagaaaa ctggactgac attgattttc tcacagagga aagccttttt     540
aactggggtt acccaatctc gaaggtgcta gcagaaaaga aagcttggga atttgcagaa     600
gagaataaga tcaatctcgt aaccgtgatt ccggcactta tagccggaaa ctctctcctc     660
tccgatcctc cgagcagttt atctctctcg atgtctttca tcaccgggaa agaaaatgcat     720 gtgacgggtc tcaaggaaat gcagaagcta tctggctcga tctcgttcgt gcacgtagac     780
gatttagctc gtgcccatt  gtttcttgcg gagaaagaaa ctgcttctgg tcgctacatt     840
tgctgtgctt acaacacaag tgttccagag attgcggatt ttctcataca gagatatcct     900
aagtacaatg tgttgtccga attcgaagag ggcttgtcga ttccgaaatt aacactatct     960
tcgcaaaaac ttatcaatga aggctttcga ttcgaatatg ggatcaatga gatgtatgat    1020
cagatgatag agtacttcga gtcaaaagga ttgatcaaag ctaaagaatc ttgattttt     1080 ataatgtcaa aatggattct aatagtatat gagtctttgg tctcattctc gttctataaa    1140
atggtattgt ataatattta ttatatattg gttgagttaa tgtcttttga tacataaata    1200
ttacatactc tcc                                                       1213

<210> SEQ ID NO 46
<211> LENGTH: 342
<212> TYPE: PRT
```

<213> ORGANISM: Arabidopsis thaliana

<400> SEQUENCE: 46

| | | | | | | | | | | | | | | | |
|---|---|---|---|---|---|---|---|---|---|---|---|---|---|---|---|
| Met | Asp | Gln | Thr | Leu | Thr | His | Thr | Gly | Ser | Lys | Lys | Ala | Cys | Val | Ile |
| 1 | | | | 5 | | | | | 10 | | | | | 15 | |
| Gly | Gly | Thr | Gly | Asn | Leu | Ala | Ser | Ile | Leu | Ile | Lys | His | Leu | Leu | Gln |
| | | | 20 | | | | | 25 | | | | | 30 | | |
| Ser | Gly | Tyr | Lys | Val | Asn | Thr | Thr | Val | Arg | Asp | Pro | Glu | Asn | Glu | Lys |
| | | | 35 | | | | 40 | | | | | 45 | | | |
| Lys | Ile | Ala | His | Leu | Arg | Gln | Leu | Gln | Glu | Leu | Gly | Asp | Leu | Lys | Ile |
| | 50 | | | | | 55 | | | | | 60 | | | | |
| Phe | Lys | Ala | Asp | Leu | Thr | Asp | Glu | Asp | Ser | Phe | Glu | Ser | Ser | Phe | Ser |
| 65 | | | | | 70 | | | | 75 | | | | | 80 | |
| Gly | Cys | Glu | Tyr | Ile | Phe | His | Val | Ala | Thr | Pro | Ile | Asn | Phe | Lys | Ser |
| | | | | 85 | | | | | 90 | | | | | 95 | |
| Glu | Asp | Pro | Glu | Lys | Asp | Met | Ile | Lys | Pro | Ala | Ile | Gln | Gly | Val | Ile |
| | | | 100 | | | | | 105 | | | | | 110 | | |
| Asn | Val | Leu | Lys | Ser | Cys | Leu | Lys | Ser | Lys | Ser | Val | Lys | Arg | Val | Ile |
| | | | 115 | | | | | 120 | | | | | 125 | | |
| Tyr | Thr | Ser | Ser | Ala | Ala | Ala | Val | Ser | Ile | Asn | Asn | Leu | Ser | Gly | Thr |
| | 130 | | | | | 135 | | | | | 140 | | | | |
| Gly | Leu | Val | Met | Asn | Glu | Glu | Asn | Trp | Thr | Asp | Ile | Asp | Phe | Leu | Thr |
| 145 | | | | | 150 | | | | | 155 | | | | | 160 |
| Glu | Glu | Lys | Pro | Phe | Asn | Trp | Gly | Tyr | Pro | Ile | Ser | Lys | Val | Leu | Ala |
| | | | | 165 | | | | | 170 | | | | | 175 | |
| Glu | Lys | Lys | Ala | Trp | Glu | Phe | Ala | Glu | Glu | Asn | Lys | Ile | Asn | Leu | Val |
| | | | 180 | | | | | 185 | | | | | 190 | | |
| Thr | Val | Ile | Pro | Ala | Leu | Ile | Ala | Gly | Asn | Ser | Leu | Leu | Ser | Asp | Pro |
| | | | 195 | | | | | 200 | | | | | 205 | | |
| Pro | Ser | Ser | Leu | Ser | Leu | Ser | Met | Ser | Phe | Ile | Thr | Gly | Lys | Glu | Met |
| | 210 | | | | | 215 | | | | | 220 | | | | |
| His | Val | Thr | Gly | Leu | Lys | Glu | Met | Gln | Lys | Leu | Ser | Gly | Ser | Ile | Ser |
| 225 | | | | | 230 | | | | | 235 | | | | | 240 |
| Phe | Val | His | Val | Asp | Asp | Leu | Ala | Arg | Ala | His | Leu | Phe | Leu | Ala | Glu |
| | | | | 245 | | | | | 250 | | | | | 255 | |
| Lys | Glu | Thr | Ala | Ser | Gly | Arg | Tyr | Ile | Cys | Cys | Ala | Tyr | Asn | Thr | Ser |
| | | | 260 | | | | | 265 | | | | | 270 | | |
| Val | Pro | Glu | Ile | Ala | Asp | Phe | Leu | Ile | Gln | Arg | Tyr | Pro | Lys | Tyr | Asn |
| | | | 275 | | | | | 280 | | | | | 285 | | |
| Val | Leu | Ser | Glu | Phe | Glu | Glu | Gly | Leu | Ser | Ile | Pro | Lys | Leu | Thr | Leu |
| | | 290 | | | | | 295 | | | | | 300 | | | |
| Ser | Ser | Gln | Lys | Leu | Ile | Asn | Glu | Gly | Phe | Arg | Phe | Glu | Tyr | Gly | Ile |
| 305 | | | | | 310 | | | | | 315 | | | | | 320 |
| Asn | Glu | Met | Tyr | Asp | Gln | Met | Ile | Glu | Tyr | Phe | Glu | Ser | Lys | Gly | Leu |
| | | | | 325 | | | | | 330 | | | | | 335 | |
| Ile | Lys | Ala | Lys | Glu | Ser | | | | | | | | | | |
| | | | | 340 | | | | | | | | | | | |

<210> SEQ ID NO 47
<211> LENGTH: 31
<212> TYPE: DNA
<213> ORGANISM: Artificial
<220> FEATURE:
<223> OTHER INFORMATION: Artificial primer

<400> SEQUENCE: 47
caccatggag aataccggag gtgtgagaaa a					31

<210> SEQ ID NO 48
<211> LENGTH: 31
<212> TYPE: DNA
<213> ORGANISM: Artificial
<220> FEATURE:
<223> OTHER INFORMATION: Artificial primer

<400> SEQUENCE: 48
tattcaatcc agatctctga ggaactaaat t					31

<210> SEQ ID NO 49
<211> LENGTH: 31
<212> TYPE: DNA
<213> ORGANISM: Artificial
<220> FEATURE:
<223> OTHER INFORMATION: Artificial primer

<400> SEQUENCE: 49
agagatctgg attgaataga tgcagaaaaa g					31

<210> SEQ ID NO 50
<211> LENGTH: 31
<212> TYPE: DNA
<213> ORGANISM: Artificial
<220> FEATURE:
<223> OTHER INFORMATION: Artificial primer

<400> SEQUENCE: 50
aatgaccatc tatttcctag tagtttgtgt a					31

<210> SEQ ID NO 51
<211> LENGTH: 31
<212> TYPE: DNA
<213> ORGANISM: Artificial
<220> FEATURE:
<223> OTHER INFORMATION: Artificial primer

<400> SEQUENCE: 51
aggaaataga tggtcattga ttgctggaag g					31

<210> SEQ ID NO 52
<211> LENGTH: 34
<212> TYPE: DNA
<213> ORGANISM: Artificial
<220> FEATURE:
<223> OTHER INFORMATION: Artificial primer

<400> SEQUENCE: 52
tcaaggtaga tcccaaagag aattcaaatc acaa					34

<210> SEQ ID NO 53
<211> LENGTH: 20
<212> TYPE: DNA
<213> ORGANISM: Artificial
<220> FEATURE:
<223> OTHER INFORMATION: Artificial primer

<400> SEQUENCE: 53
gtgtgccaca cagttctcca					20

<210> SEQ ID NO 54
<211> LENGTH: 20
<212> TYPE: DNA

<213> ORGANISM: Artificial
<220> FEATURE:
<223> OTHER INFORMATION: Artificial primer

<400> SEQUENCE: 54
atggctgcat caatcaccgc                                                    20

<210> SEQ ID NO 55
<211> LENGTH: 22
<212> TYPE: DNA
<213> ORGANISM: Artificial
<220> FEATURE:
<223> OTHER INFORMATION: Artificial primer

<400> SEQUENCE: 55
atcttcctcc tatacatttc ag                                                 22

<210> SEQ ID NO 56
<211> LENGTH: 20
<212> TYPE: DNA
<213> ORGANISM: Artificial
<220> FEATURE:
<223> OTHER INFORMATION: Artificial primer

<400> SEQUENCE: 56
ggcactatta ctctattgct                                                    20

<210> SEQ ID NO 57
<211> LENGTH: 20
<212> TYPE: DNA
<213> ORGANISM: Artificial
<220> FEATURE:
<223> OTHER INFORMATION: Artificial primer

<400> SEQUENCE: 57
catcccacaa gggcttttga                                                    20

<210> SEQ ID NO 58
<211> LENGTH: 22
<212> TYPE: DNA
<213> ORGANISM: Artificial
<220> FEATURE:
<223> OTHER INFORMATION: Artificial primer

<400> SEQUENCE: 58
atgggttcta tggccgaaac tg                                                 22

<210> SEQ ID NO 59
<211> LENGTH: 27
<212> TYPE: DNA
<213> ORGANISM: Artificial
<220> FEATURE:
<223> OTHER INFORMATION: Artificial primer

<400> SEQUENCE: 59
catcaattac agaattttgt tgctcag                                            27

<210> SEQ ID NO 60
<211> LENGTH: 22
<212> TYPE: DNA
<213> ORGANISM: Artificial
<220> FEATURE:
<223> OTHER INFORMATION: Artificial primer

<400> SEQUENCE: 60
atgggttcag tctcagaaac ag                                                 22

<210> SEQ ID NO 61
<211> LENGTH: 20
<212> TYPE: DNA
<213> ORGANISM: Artificial
<220> FEATURE:
<223> OTHER INFORMATION: Artificial primer

<400> SEQUENCE: 61
tccataacct tgaatcttcc                                          20

<210> SEQ ID NO 62
<211> LENGTH: 20
<212> TYPE: DNA
<213> ORGANISM: Artificial
<220> FEATURE:
<223> OTHER INFORMATION: Artificial primer

<400> SEQUENCE: 62
caagttccaa caatagacct                                          20

<210> SEQ ID NO 63
<211> LENGTH: 20
<212> TYPE: DNA
<213> ORGANISM: Artificial
<220> FEATURE:
<223> OTHER INFORMATION: Artificial primer

<400> SEQUENCE: 63
tgatagattt catggcttcc                                          20

<210> SEQ ID NO 64
<211> LENGTH: 20
<212> TYPE: DNA
<213> ORGANISM: Artificial
<220> FEATURE:
<223> OTHER INFORMATION: Artificial primer

<400> SEQUENCE: 64
taactgaggc aagtatttcc                                          20

<210> SEQ ID NO 65
<211> LENGTH: 20
<212> TYPE: DNA
<213> ORGANISM: Artificial
<220> FEATURE:
<223> OTHER INFORMATION: Artificial primer

<400> SEQUENCE: 65
taaccctcat agattggcac                                          20

<210> SEQ ID NO 66
<211> LENGTH: 20
<212> TYPE: DNA
<213> ORGANISM: Artificial
<220> FEATURE:
<223> OTHER INFORMATION: Artificial primer

<400> SEQUENCE: 66
agtaactggg atgacatgga                                          20

<210> SEQ ID NO 67
<211> LENGTH: 20
<212> TYPE: DNA
<213> ORGANISM: Artificial
<220> FEATURE:

```
<223> OTHER INFORMATION: Artificial primer

<400> SEQUENCE: 67
tgacaaagtt ataggacgag                                              20

<210> SEQ ID NO 68
<211> LENGTH: 19
<212> TYPE: DNA
<213> ORGANISM: Artificial
<220> FEATURE:
<223> OTHER INFORMATION: Artificial primer

<400> SEQUENCE: 68
aagttgtaga ttgaggtgg                                               19

<210> SEQ ID NO 69
<211> LENGTH: 26
<212> TYPE: DNA
<213> ORGANISM: Artificial
<220> FEATURE:
<223> OTHER INFORMATION: Artificial primer

<400> SEQUENCE: 69
tgcaaacaaa acatctcacc tcatag                                       26

<210> SEQ ID NO 70
<211> LENGTH: 22
<212> TYPE: DNA
<213> ORGANISM: Artificial
<220> FEATURE:
<223> OTHER INFORMATION: Artificial primer

<400> SEQUENCE: 70
aatttccacg cagccttttc ag                                           22

<210> SEQ ID NO 71
<211> LENGTH: 24
<212> TYPE: DNA
<213> ORGANISM: Artificial
<220> FEATURE:
<223> OTHER INFORMATION: Artificial primer

<400> SEQUENCE: 71
acagggagtc atttggatga ggtg                                         24

<210> SEQ ID NO 72
<211> LENGTH: 24
<212> TYPE: DNA
<213> ORGANISM: Artificial
<220> FEATURE:
<223> OTHER INFORMATION: Artificial primer

<400> SEQUENCE: 72
acagggagtc atttggatga ggtg                                         24

<210> SEQ ID NO 73
<211> LENGTH: 24
<212> TYPE: DNA
<213> ORGANISM: Artificial
<220> FEATURE:
<223> OTHER INFORMATION: Artificial primer

<400> SEQUENCE: 73
agctagtgaa ccaccaaggc atcc                                         24
```

```
<210> SEQ ID NO 74
<211> LENGTH: 25
<212> TYPE: DNA
<213> ORGANISM: Artificial
<220> FEATURE:
<223> OTHER INFORMATION: Artificial primer

<400> SEQUENCE: 74
actgtcctcc tttctcagaa gtgtc                                           25

<210> SEQ ID NO 75
<211> LENGTH: 24
<212> TYPE: DNA
<213> ORGANISM: Artificial
<220> FEATURE:
<223> OTHER INFORMATION: Artificial primer

<400> SEQUENCE: 75
agtctcaatg gtaagtcctg gtcc                                            24

<210> SEQ ID NO 76
<211> LENGTH: 25
<212> TYPE: DNA
<213> ORGANISM: Artificial
<220> FEATURE:
<223> OTHER INFORMATION: Artificial primer

<400> SEQUENCE: 76
ggacaagcac tatttggaga tggag                                           25

<210> SEQ ID NO 77
<211> LENGTH: 24
<212> TYPE: DNA
<213> ORGANISM: Artificial
<220> FEATURE:
<223> OTHER INFORMATION: Artificial primer

<400> SEQUENCE: 77
agaccaagtg ggtggtcttc aagc                                            24

<210> SEQ ID NO 78
<211> LENGTH: 25
<212> TYPE: DNA
<213> ORGANISM: Artificial
<220> FEATURE:
<223> OTHER INFORMATION: Artificial primer

<400> SEQUENCE: 78
atctctgaga tacacgatca aggac                                           25

<210> SEQ ID NO 79
<211> LENGTH: 22
<212> TYPE: DNA
<213> ORGANISM: Artificial
<220> FEATURE:
<223> OTHER INFORMATION: Artificial primer

<400> SEQUENCE: 79
tcaatgtgcc tgccatgtat gt                                              22

<210> SEQ ID NO 80
<211> LENGTH: 22
<212> TYPE: DNA
<213> ORGANISM: Artificial
<220> FEATURE:
<223> OTHER INFORMATION: Artificial primer
```

```
<400> SEQUENCE: 80
actcacaccg tcaccagaat cc                                          22

<210> SEQ ID NO 81
<211> LENGTH: 20
<212> TYPE: DNA
<213> ORGANISM: Artificial
<220> FEATURE:
<223> OTHER INFORMATION: Artificial primer

<400> SEQUENCE: 81
ggcagagaca gggaagaaca                                             20

<210> SEQ ID NO 82
<211> LENGTH: 19
<212> TYPE: DNA
<213> ORGANISM: Artificial
<220> FEATURE:
<223> OTHER INFORMATION: Artificial primer

<400> SEQUENCE: 82
taaatccgca ccaaaccaa                                              19

<210> SEQ ID NO 83
<211> LENGTH: 26
<212> TYPE: DNA
<213> ORGANISM: Artificial
<220> FEATURE:
<223> OTHER INFORMATION: Artificial primer

<400> SEQUENCE: 83
cggatccatg tctaccttca aaaatg                                      26

<210> SEQ ID NO 84
<211> LENGTH: 24
<212> TYPE: DNA
<213> ORGANISM: Artificial
<220> FEATURE:
<223> OTHER INFORMATION: Artificial primer

<400> SEQUENCE: 84
tgcggccgca ctagtgacaa tttg                                        24

<210> SEQ ID NO 85
<211> LENGTH: 24
<212> TYPE: DNA
<213> ORGANISM: Artificial
<220> FEATURE:
<223> OTHER INFORMATION: Artificial primer

<400> SEQUENCE: 85
gtcctctaag gtttaatgaa ccgg                                        24

<210> SEQ ID NO 86
<211> LENGTH: 22
<212> TYPE: DNA
<213> ORGANISM: Artificial
<220> FEATURE:
<223> OTHER INFORMATION: Artificial primer

<400> SEQUENCE: 86
gaaagacaca gccaagttgc ac                                          22

<210> SEQ ID NO 87
<211> LENGTH: 22
```

```
<212> TYPE: DNA
<213> ORGANISM: Artificial
<220> FEATURE:
<223> OTHER INFORMATION: Artificial primer

<400> SEQUENCE: 87
attgcctgcc caagagtgta ag                                              22

<210> SEQ ID NO 88
<211> LENGTH: 22
<212> TYPE: DNA
<213> ORGANISM: Artificial
<220> FEATURE:
<223> OTHER INFORMATION: Artificial primer

<400> SEQUENCE: 88
cagccaagtt gcacaaaaca ac                                              22

<210> SEQ ID NO 89
<211> LENGTH: 975
<212> TYPE: DNA
<213> ORGANISM: Medicago truncatula

<400> SEQUENCE: 89
atggagaata ccggaggtgt gagaaaaggc gcatggactt acaaggaaga tgagctactc      60
aaggcttgca ttaacacgta cggtgaagga aaatggaatt tagttcctca gagatctggt     120
atggtatatg ttcttattct actatttatt tggcttatag ttctagttta gttgaaaccc     180
tatattggag caaccctat aacgatgcat taattcttta acataaatat cttggcaaaa      240
tttgttacac ttgacacaca ggattgaata gatgcagaaa agttgtaga ttgaggtggt      300 taaattactt aagccccaac atcaacagag gaagattttc tgaggatgaa gaagatttga     360
tcctaaggtt acacaaacta ctaggaaata ggtaatctta catagttaaa ttgaaattaa     420
agttgtttct gtgtgctagc tgctgatcta tttcagctat ttacttactg atatacatat     480
gtatatagat ggtcattgat tgctggaagg cttccgggta gaacagctaa tgatgtgaag     540
aactattggc acacaaattt ggcaaagaaa gtggtttcag aaaaggaaga agagaaagaa     600
aacgataaac ctaaggaaac catgaaagct catgaagtta ttaaacctcg tcctataact     660
ttgtcaagtc attcaaattg gttgaagggg aaaaatagta ttcctagaga tcttgattac     720
tcagagaata tggcttcaaa tcaaattggt agagagtgtg cttctacttc aaaaccagat     780
ctaggtaatg ccccaatacc atgtgaaatg tggtgtgaca gtttgtggaa cttgggagaa     840
catgtagaca gtgagaaaat tgggtcatgc tcttcattac aagaggagaa cttaatggag     900
tttccaaatg ttgatgatga ctccttttgg gatttcaacc tttgtgattt gaattctctt     960
tgggatctac cttga                                                     975

<210> SEQ ID NO 90
<211> LENGTH: 1015
<212> TYPE: DNA
<213> ORGANISM: Medicago truncatula

<400> SEQUENCE: 90
atggagatga ccagaggcgt gagaaaaggt gcatggacat atgaggaaga caagctactc      60
aaggcttgta tacagaagta tggtgaagga aaatggcatt tagttccaca agagcaggt     120 ataatgaatg ccgtttattt taggcttaca attagttaaa ttgaacaact atatatcaaa     180
gcaaatgcaa aaaaattacc atgcataact gcttaaatta tatgttacac atgacaggat     240
```

-continued

| | |
|---|---|
| tgaataggtg ccgaaaaagc tgtagattga ggtggttaaa ttatttaacc cccaacatca | 300 |
| aaagggaaag ctttgctgag gatgaagttg atatgatgct aaggttacac aaacttctag | 360 |
| ggaataggta atcttccaag gacaagttaa tattcattat atgatgtttg tggtgccata | 420 |
| attagcatat atatattctt ttaatttatg tcatatttca gctatatatg tgtttactta | 480 |
| tatgtaatat gtatttagat ggtcattgat tgctgcaagg cttccgggta gaacagctaa | 540 |
| tgatgtgaag aattattggc acacacattt gagaagaag atggtttcaa gaacactaga | 600 |
| agaaagaaa gaaaaaccta aggaaaccat gaaagttcat gaaattatta aacctaaacc | 660 |
| tcgaactttc tcaactcatc caccttcgtt gaactgaaa cataatatta atgtgacacc | 720 |
| aattgtggcg gtttcaactc aacacggtga agtctcgcca aatcgtgata ataaagagat | 780 |
| tacggattca aaccaaattg gtagagatat tgttggtgtt tcccaaccaa gtcttggtag | 840 |
| tgctccaata ccgtgtgcaa tgttgtggga cagtttattg aacttggagg agcataaaag | 900 |
| tagtgagaaa attgggtcag gctctttatt acaagaggag aacttcattt ctgagtttcc | 960 |
| aaatgtggat gactcctttt gggatttcaa cctttgtgat ttcgattctc tttga | 1015 |

<210> SEQ ID NO 91
<211> LENGTH: 3207
<212> TYPE: DNA
<213> ORGANISM: Medicago truncatula

<400> SEQUENCE: 91

| | |
|---|---|
| atggataata ccataggcgt gaaaaaaggt gcatggacat acgaggaaga caacttactc | 60 |
| aaggcttaca ttaacaagta tggtgaagga aaatggcatt taattcctca aagagcaggt | 120 |
| tcaggtataa tgaattgaat gccacttctt ctaccaaatg atataaatta aacacatata | 180 |
| gaaccaaatg taaattaacc atgttaatt ttctttctg catgtcttgt taaaatgtta | 240 |
| tttcttttga taaaactttg ctagcattat gctatatcc aaaacagccc aaataatcaa | 300 |
| tgtcaaaccg gtagggatgg atccaccgta tgacttagta tgactatagc acactagagt | 360 |
| attactcaaa aagtgtgtgt acgcgcgcgc gttctggcat gtgagaatcg actacaaaga | 420 |
| caaataagtg aaaaatataa gcatttatct ctaagatata atgtttgatg tataaatgtc | 480 |
| gcatcattag tatgtatccc aattctgaat atccaactct gatgattttc tttgttgaat | 540 |
| ctccaattct gattttgaat tttgattttt ctcagaatgc tttagttatt gtgcttacaa | 600 |
| agtcattgtt ttgctttata gtataaagaa atattttcct atgctttctt gagagaaaca | 660 |
| atgttatttc ttattttttt agtataattt acttaaagtt tctttcataa tttaacagct | 720 |
| gcaaaatatt atgtctgaat ccaccccttc actcgggatt agtggtgttt atattctatc | 780 |
| gaattagatt gaattatgga tttaagaacc gaaccaagta tataaatcaa tgcttcttta | 840 |
| ttattttgat taataaatat gagatattgc attaatctat tatttactga ttttaatta | 900 |
| atactatgag ataccaatta atgtattatg gtttaaatta ttagtatgat atattacatt | 960 |
| aatctactat ttttgaaaaa aattatatat ttaagttata aaattaccct gcgatttata | 1020 |
| tatataatgc agggcttaac tcaacttaat tgttatgctg aacttaactg aattgttagg | 1080 |
| gacaatgtat aatataatgc agggtttgaa gttcaaatct caaacaacta tttactcacc | 1140 |
| ttaaaaaaat tgaatttttt tctactagac tactcaacaa attaaaaaca cggaaataga | 1200 |
| aaacgaatct accaaaaaaa acatataaat cataattcga tatcatggat gagagccacg | 1260 |
| atttaccgtg gaacttcaaa taaaatgaaa agtgcactat attggatata tacaatcata | 1320 |
| attcgtttta aaaaagtct aattaattaa attgaacaac tatatagaag aaaatgtttg | 1380 |

-continued

```
tatagcaata  tacaaccaaa  tgttaatcgt  ttttgtgatg  ttatctcatt  ggtatgaata   1440
ttatatatta  tatatatagg  gggctgagtt  tgaaccccga  acattccact  aaacaaatgc   1500
taatcaactg  tatcacacat  tatttattta  tttttattgt  gagaatcttt  catccaacta   1560
tgttgttact  aattatagaa  tccaactatc  cttatcaaaa  tatgtgtttg  ttacacttac   1620
aggattgaat  agatgtcgaa  aaagttgtag  attgaggtgg  ataaattatt  taaagcccaa   1680
catcaataga  aaaagctttt  ctgaggatga  agttgatatg  atcctaaggt  tacacaaact   1740
cttaggaaat  aggtaagctt  ccgaggccaa  attaaaattc  aatttgtgtt  tgtgtatatt   1800
tgttgatcat  cttgttatgc  attctagcta  taattaatta  tgatattttt  catctgttga   1860
tgtgatagga  tccaattcga  ttagggatta  cattccatat  cttattttaa  atagggttaa   1920
atatgttttt  gatccttata  aatatgtcat  attttcgttt  tagtctctct  aaaaaatttc   1980 ttcaacttttt  agttcccaaa  agtttttcat  cttcattttt  tgtctccttt  aaataaaact   2040
tgtatgtgga  aatattttg   aatttcctca  aaaaaaaaaa  agaataaaaa  ttttgtataa   2100
aaaatttaaa  atattataag  aatcccacca  aaaaaaata   tgaattttat  attttttggcg   2160 gttaaaaatt  catatttaat  ttatgttttg  ttaaaaaatt  ataactttt   tgggagagat   2220 ttttacaata  ttctacctat  ttctgcacga  tttcattaaa  aaaaaaatat  atactaaaat   2280
cttcataaaa  ttagggatca  aaagtagtga  ttgaaaattt  tatagggact  aaaagttgaa   2340
gaaaattttt  agagggatta  aaatcaaaaa  tagatatatt  tataggaatc  aaaaatatat   2400
ttaactattt  taagtatttt  accaggatga  ctccttttac  ggattccaaa  ctttgtgttt   2460
tcaaatttta  tatgcttttt  aatttactcc  atgggtctca  atttataaat  cattatttt    2520 tcaatatcat  atgaattaat  ataccatttta  tttttgtatg  agaaaactaa  attatgagtt   2580
attttacaaa  attatccttt  acttttttaag  taaaatcatt  ttttttagtga  tggaacatag   2640 gaatatacaa  tttttttagc  cacatttaat  catatatgta  tatttagatg  gtcattgatt   2700
gctggaaggc  ttccgggtag  aacagctaat  agtgtgaaaa  actattggaa  cacacacttg   2760
ttgaagaagg  tggtttcaaa  acaagaagaa  gaaaagaga   aaccaatgga  gacaatgaaa   2820
gctcaccaag  ttattaaacc  tagacctata  actttttcaa  ctcaatcatc  ttggttgaat   2880
gtgaaacaca  ataattttgt  gacacaacca  ttattggctt  caaacaatga  tggttgtttt   2940
cctagagatc  gtgatgacaa  aatgactatg  gttgttccta  accaaattgg  taaagattgt   3000
gcttcttctt  cacaaccaat  tctaggtaat  gtcccaatac  cttgtacaat  gtggtcagaa   3060
agtttatgga  acttggggga  gcaagtagat  agtgagataa  ttggatcgtc  ctcttcatta   3120
caagtggaga  actatgagga  gttttcaatt  gttgatgact  tttgggattt  caacatttgt   3180
gattatgatt  ctctttggga  tctttag                                         3207
```

<210> SEQ ID NO 92
<211> LENGTH: 2046
<212> TYPE: DNA
<213> ORGANISM: Medicago truncatula

<400> SEQUENCE: 92

```
atgcctttgt  ttgtctgtgg  acaaaagcaa  gtgtatatgg  agaagtgtaa  gactagaggt    60
gtgagaaaag  gtgcatggac  atatgaggaa  gacaagctac  tcaaggcttg  tatgcagaag   120
tatggtgaag  gaaaatggca  tttagttcca  caaagagcag  gtatataatg  aaagttgctt   180
attgtactgt  atatttggct  tatgattaat  taaactgaat  aataacatag  aagcaatgta   240
```

```
acttataatt cattttcttt atgtatgtga aaatacttgt tacatgtact tggcaggatt      300
gaataggtgc cggaaaagtt gtagattgag gtggttaaat tatttaaacc ccaccatcaa      360
tagagagagt ttttctgagg atgaagttga tatgatttta aggttacaca agcttttagg      420
gaacaggtat gtatgatgcc aaggccaagt tatcatttaa ttaaatattt tcttataatt      480
caattcagct gttaacatta tattcttaat attatgtttc cttaaatgta agtttatttg      540
ttcataaagt gtaagcttag cagcatggag tttgttttgt aatctgaagg gtcaaaaatt      600
caaattttct cgaagattgg tgtgaaaaag accaatatat aattaagggt taattaagtt      660
tttagtccct ataaatattc acagttttgt ttttttagtc tctacaaaat aaaatcacat      720
cttttagtcc ctataaaaat ttcatcagca ttttagtcc ctataaaatt tttccattag       780 cattttagt ccctgtaaaa aatttccatc aacattttg gtccctaaag tgcttaagaa        840
aaatgtcaca gggactaaaa agtgtgattt tattttgtaa ggtctaaaaa caaatctgtg      900
aatatttata ggactaaaat cttaattaac cctataatta atgccacttt attaataata      960
tttcacttgc tattttttt ataaaaaaa agtatgtgtc ttttatctc ttaaaaggac         1020 taattctaaa ttactagata gtacatagaa ctaatatttt ttttttttcaa ataaaccttt    1080 gattaatact actagttaag tgtcttagat caagagatat tgataaaaaa ggacaagtgt     1140
cttataatat gaggaagtca atattaaata gataaagttt agtttacacc gtagatgata    1200
acttagtata catcttgaaa taaagataga aaacaaaagt gcgatgtcgt tgatgatgtg    1260
ataagaagag caagctagag atataataaa gtattaaatg aatgtataaa aagttggggt    1320
gtttaatatc attgttgata ttaagtacat caagttataa aatagtattt cacgattttt    1380
ataaaagaga atgttaccac ttaaactata ttttaagaat tttgtcaata aaaaaaaaa     1440 actatatttt aaaaataatt taattgtatg aagtaagtaa gcatgatatt tttatatttt    1500
tatagatggt cattgattgc tgcaagactc ccgggtagaa cagctaatga tgtgaagaat    1560
tattggcaca cacatttacg caagaagatg gtttcaagaa aagaagaaaa gaaagaaaat    1620
gagaaaccta agaaagcat gcaaactcat gaagttatta aacctcaacc tcgaactttt     1680
tcatctcatt caccatggtt gaatgggaaa tataataatt ttgtgacacc aatagtaact    1740
gtttcaacaa atgatggtaa tgttgcaaaa gatagtgaag tagatactat tctaccaatt    1800
aatggtgatg gtgatagtgc tgcacaacca tatcttgaaa atccaacact gtcttccatg    1860
tggtgggaga gtttgttgaa cgtgagcaat gacaaaattg gatcatgctc tttactatta    1920
ccagaggaat attccaaatt aaatgttgag aactttcttg ctgaaggacc cagtactgtc    1980
ggtgatttct cctgggattc taccatttgt gaatttgact ctcttttaga tgatatctta    2040
aattag                                                               2046

<210> SEQ ID NO 93
<211> LENGTH: 825
<212> TYPE: DNA
<213> ORGANISM: Lycopersicon esculentum

<400> SEQUENCE: 93
atgaacagta catctatgtc ttcattggga gtgagaaaag gttcatggac tgatgaagaa       60
gattttctct aagaaaatgt attgataagt atggtgaagg aaaatggcat cttgttccca      120
taagagctgg tctgaataga tgtcggaaaa gttgtagatt gaggtggctg aattatctaa      180
ggccacatat tcaagagagg tgactttgaa caagatgaag tggatctcat tttgaggctt      240
cataagctct taggcaacag atggtcactt attgctggta gacttcccgg aaggacagct      300
```

```
aacgatgtga aaaactattg gaacactaat cttctaagga agttaaatac tactaaaatt    360
gttcctcgcg aaaagattaa caataagtgt ggagaaatta gtactaagat tgaaattata    420
aaacctcaac gacgcaagta tttctcaagc acaatgaaga atgttacaaa caataatgta    480
attttggacg aggaggaaca ttgcaaggaa ataataagtg agaaacaaac tccagatgca    540
tcgatggaca acgtagatcc atggtggata aatttactgg aaaattgcaa tgacgatatt    600
gaagaagatg aagaggttgt aattaattat gaaaaaacac taacaagttt gttacatgaa    660
gaaatatcac caccattaaa tattggtgaa ggtaactcca tgcaacaagg acaaataagt    720
catgaaaatt ggggtgaatt ttctcttaat ttaccaccca tgcaacaagg agtacaaaat    780
gatgattttt ctgctgaaat tgacttatgg aatctacttg attaa                   825

<210> SEQ ID NO 94
<211> LENGTH: 768
<212> TYPE: DNA
<213> ORGANISM: Petunia hybrida

<400> SEQUENCE: 94
atgagtactt ctaatgcatc aacatcagga gtaaggaaag gtgcatggac cgaggaagaa    60 gatctttat tgagagaatg cattgacaag tatggagaag gaaagtggca tctagttcca    120
gttagagctg gtctgaatag atgcaggaaa agttgcagac ttaggtggtt gaattatcta    180
aggccacata taaaaagagg ggacttctct ttggatgaag tagatctcat tttgaggctt    240
cataagcttc taggcaacag atggtcactt atagctggta gacttcctgg aagaacagca    300
aacgatgtca aaaactattg gaacacccac cttcgaaaga agttaattgc tcctcatgat    360
cagaaacaag agagcaagaa caaagccgtg aaaattaccg agaacaacat aataaaacct    420
cgtcctcgga ccttctcaag gccggcaatg aataattttc cttgttggaa cggcaaaagt    480
tgtaataaaa acactataga caagaatgaa ggtgacacag aaataataaa gtttagtgat    540
gagaagcaaa aaccggaaga atcgatagat gatggacttc aatggtgggc caatttatta    600
gccaacaaca ttgagattga ggaattagtt agttgtaatt caccaacatt gttgcatgag    660
gaaacagcac catcggtaaa tgctgaaagc agccttactc aaggaggagg aagtggctta    720
agtgactttt cagttgatat tgatgacata tgggatttag ttagttaa                768

<210> SEQ ID NO 95
<211> LENGTH: 274
<212> TYPE: PRT
<213> ORGANISM: Lycopersicon esculentum

<400> SEQUENCE: 95

Met Asn Ser Thr Ser Met Ser Ser Leu Gly Val Arg Lys Gly Ser Trp
1               5                   10                  15

Thr Asp Glu Glu Asp Phe Leu Leu Arg Lys Cys Ile Asp Lys Tyr Gly
                20                  25                  30

Glu Gly Lys Trp His Leu Val Pro Ile Arg Ala Gly Leu Asn Arg Cys
            35                  40                  45

Arg Lys Ser Cys Arg Leu Arg Trp Leu Asn Tyr Leu Arg Pro His Ile
        50                  55                  60

Lys Arg Gly Asp Phe Glu Gln Asp Glu Val Asp Leu Ile Leu Arg Leu
65                  70                  75                  80

His Lys Leu Leu Gly Asn Arg Trp Ser Leu Ile Ala Gly Arg Leu Pro
                85                  90                  95
```

```
Gly Arg Thr Ala Asn Asp Val Lys Asn Tyr Trp Asn Thr Asn Leu Leu
            100                 105                 110

Arg Lys Leu Asn Thr Thr Lys Ile Val Pro Arg Glu Lys Ile Asn Asn
        115                 120                 125

Lys Cys Gly Glu Ile Ser Thr Lys Ile Glu Ile Lys Pro Gln Arg
    130                 135                 140

Arg Lys Tyr Phe Ser Ser Thr Met Lys Asn Val Thr Asn Asn Val
145                 150                 155                 160

Ile Leu Asp Glu Glu Glu His Cys Lys Glu Ile Ile Ser Glu Lys Gln
                165                 170                 175

Thr Pro Asp Ala Ser Met Asp Asn Val Asp Pro Trp Trp Ile Asn Leu
            180                 185                 190

Leu Glu Asn Cys Asn Asp Asp Ile Glu Glu Asp Glu Glu Val Val Ile
        195                 200                 205

Asn Tyr Glu Lys Thr Leu Thr Ser Leu Leu His Glu Glu Ile Ser Pro
    210                 215                 220

Pro Leu Asn Ile Gly Glu Gly Asn Ser Met Gln Gln Gly Gln Ile Ser
225                 230                 235                 240

His Glu Asn Trp Gly Glu Phe Ser Leu Asn Leu Pro Pro Met Gln Gln
                245                 250                 255

Gly Val Gln Asn Asp Asp Phe Ser Ala Glu Ile Asp Leu Trp Asn Leu
            260                 265                 270

Leu Asp

<210> SEQ ID NO 96
<211> LENGTH: 255
<212> TYPE: PRT
<213> ORGANISM: Petunia hybrida

<400> SEQUENCE: 96

Met Ser Thr Ser Asn Ala Ser Thr Ser Gly Val Arg Lys Gly Ala Trp
1               5                   10                  15

Thr Glu Glu Asp Leu Leu Leu Arg Glu Cys Ile Asp Lys Tyr Gly
            20                  25                  30

Glu Gly Lys Trp His Leu Val Pro Val Arg Ala Gly Leu Asn Arg Cys
        35                  40                  45

Arg Lys Ser Cys Arg Leu Arg Trp Leu Asn Tyr Leu Arg Pro His Ile
    50                  55                  60

Lys Arg Gly Asp Phe Ser Leu Asp Glu Val Asp Leu Ile Leu Arg Leu
65                  70                  75                  80

His Lys Leu Leu Gly Asn Arg Trp Ser Leu Ile Ala Gly Arg Leu Pro
                85                  90                  95

Gly Arg Thr Ala Asn Asp Val Lys Asn Tyr Trp Asn Thr His Leu Arg
            100                 105                 110

Lys Lys Leu Ile Ala Pro His Asp Gln Lys Gln Glu Ser Lys Asn Lys
        115                 120                 125

Ala Val Lys Ile Thr Glu Asn Asn Ile Ile Lys Pro Arg Pro Arg Thr
    130                 135                 140

Phe Ser Arg Pro Ala Met Asn Asn Phe Pro Cys Trp Asn Gly Lys Ser
145                 150                 155                 160

Cys Asn Lys Asn Thr Ile Asp Lys Asn Glu Gly Asp Thr Glu Ile Ile
                165                 170                 175

Lys Phe Ser Asp Glu Lys Gln Lys Pro Glu Glu Ser Ile Asp Asp Gly
            180                 185                 190
```

-continued

```
Leu Gln Trp Trp Ala Asn Leu Ala Asn Asn Ile Glu Ile Glu Glu
        195                 200                 205

Leu Val Ser Cys Asn Ser Pro Thr Leu Leu His Glu Glu Thr Ala Pro
        210                 215                 220

Ser Val Asn Ala Glu Ser Ser Leu Thr Gln Gly Gly Gly Ser Gly Leu
225                 230                 235                 240

Ser Asp Phe Ser Val Asp Ile Asp Asp Ile Trp Asp Leu Val Ser
                245                 250                 255

<210> SEQ ID NO 97
<211> LENGTH: 248
<212> TYPE: PRT
<213> ORGANISM: Arabidopsis thaliana

<400> SEQUENCE: 97

Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Lys Leu Ser Ser Asp Glu Val Asp Leu Leu Leu Arg Leu His Arg Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
        115                 120                 125

Pro Thr Thr Pro Ala Leu Lys Asn Asn Val Tyr Lys Pro Arg Pro Arg
    130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Asp Gln Leu Val
            180                 185                 190

Asn Asn Leu Ile Asp Gly Asp Asn Met Trp Leu Glu Lys Phe Leu Glu
        195                 200                 205

Glu Ser Gln Glu Val Asp Ile Leu Val Pro Glu Ala Thr Thr Thr Glu
    210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245

<210> SEQ ID NO 98
<211> LENGTH: 185
<212> TYPE: PRT
<213> ORGANISM: Artificial sequence
<220> FEATURE:
<223> OTHER INFORMATION: Consensus amino acid sequence
<220> FEATURE:
<221> NAME/KEY: misc_feature
<222> LOCATION: (1)..(3)
<223> OTHER INFORMATION: Xaa can be any naturally occurring amino acid
```

```
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (51)..(51)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (55)..(55)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (59)..(60)
<223> OTHER INFORMATION: Xaa can be any naturally occurring amino acid
<220> FEATURE:
<221> NAME/KEY: misc_feature
<222> LOCATION: (65)..(66)
<223> OTHER INFORMATION: Xaa can be any naturally occurring amino acid
<220> FEATURE:
<221> NAME/KEY: misc_feature
<222> LOCATION: (82)..(82)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid
<220> FEATURE:
<221> NAME/KEY: misc_feature
<222> LOCATION: (99)..(99)
<223> OTHER INFORMATION: Xaa can be any naturally occurring amino acid
<220> FEATURE:
<221> NAME/KEY: misc_feature
<222> LOCATION: (103)..(111)
<223> OTHER INFORMATION: Xaa can be any naturally occurring amino acid
<220> FEATURE:
<221> NAME/KEY: misc_feature
<222> LOCATION: (113)..(118)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (124)..(151)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid
<220> FEATURE:
<221> NAME/KEY: misc_feature
<222> LOCATION: (155)..(163)
<223> OTHER INFORMATION: Xaa can be any naturally occurring amino acid
<220> FEATURE:
<221> NAME/KEY: misc_feature
<222> LOCATION: (165)..(165)
<223> OTHER INFORMATION: Xaa can be any naturally occurring amino acid
<220> FEATURE:
<221> NAME/KEY: misc_feature
<222> LOCATION: (167)..(168)
<223> OTHER INFORMATION: Xaa can be any naturally occurring amino acid
<220> FEATURE:
<221> NAME/KEY: misc_feature
<222> LOCATION: (170)..(176)
```

```
-continued

<223> OTHER INFORMATION: Xaa can be any naturally occurring amino acid
<220> FEATURE:
<221> NAME/KEY: misc_feature
<222> LOCATION: (178)..(180)
<223> OTHER INFORMATION: Xaa can be any naturally occurring amino acid
<220> FEATURE:
<221> NAME/KEY: misc_feature
<222> LOCATION: (182)..(182)
<223> OTHER INFORMATION: Xaa can be any naturally occurring amino acid
<220> FEATURE:
<221> NAME/KEY: misc_feature
<222> LOCATION: (184)..(185)
<223> OTHER INFORMATION: Xaa can be any naturally occurring amino acid

<400> SEQUENCE: 98

Xaa Xaa Xaa Gly Val Arg Lys Gly Ala Trp Thr Glu Glu Asp Leu Leu
1               5                   10                  15

Xaa Cys Ile Xaa Lys Tyr Gly Glu Gly Lys Trp His Leu Val Pro Arg
            20                  25                  30

Ala Gly Leu Asn Arg Cys Arg Lys Ser Cys Arg Leu Arg Trp Leu Asn
        35                  40                  45

Tyr Leu Xaa Pro Xaa Ile Xaa Arg Xaa Phe Xaa Xaa Asp Glu Val Asp
50                  55                  60

Xaa Xaa Leu Arg Leu His Lys Leu Leu Gly Asn Arg Trp Ser Leu Ile
65                  70                  75                  80

Ala Xaa Arg Leu Pro Gly Arg Thr Ala Asn Asp Val Lys Asn Tyr Trp
                85                  90                  95

Xaa Thr Xaa Leu Lys Lys Xaa Xaa Xaa Xaa Xaa Xaa Xaa Xaa Xaa Lys
            100                 105                 110

Xaa Xaa Xaa Xaa Xaa Xaa Ile Lys Pro Xaa Pro Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
        130                 135                 140

Xaa Xaa Xaa Xaa Xaa Xaa Xaa Leu Xaa Asn Xaa Xaa Xaa Xaa Xaa Xaa
145                 150                 155                 160

Xaa Xaa Xaa Leu Xaa Glu Xaa Xaa Glu Xaa Xaa Xaa Xaa Xaa Xaa Xaa
            165                 170                 175

Asp Xaa Xaa Xaa Asp Xaa Leu Xaa Xaa
            180                 185
```

PRODUCTION OF PROANTHOCYANIDINS TO IMPROVE FORAGE QUALITY

This application claims the priority of U.S. Provisional application Ser. No. 60/914,279, filed Apr. 26, 2007, the entire disclosure of which is incorporated herein by reference.

GOVERNMENT INTEREST

The government may own rights in this invention pursuant to Grant No. 0416833 of the National Science Foundation-Molecular Biochemistry Program.

BACKGROUND OF THE INVENTION

1. Field of the Invention

The present invention generally relates to plant genetics. More specifically, the invention relates to genes involved in the biosynthesis of anthocyanins, proanthocyanidins, and tannins in alfalfa (*Medicago* sp.), and methods for use thereof.

2. Description of the Related Art

Proanthocyanidins (PAs), also known as condensed tannins (CTs), are polymers of flavonoid (flavan-3-ol) units. Their name reflects the fact that, on acid hydrolysis, the extension units are converted to colored anthocyanidins, and this forms the basis of the classical assay for these compounds (Porter 1989). Anthocyanins and proanthocyanidins are found in many plant species. Anthocyanins contribute to the coloration of plant tissues, may act as attractants to pollinators (Schemske and Bradshaw, 1999), and provide UV protection (Reddy et al., 1994). PAs provide plants with protection against insects, herbivores and fungal infection (Schultz and Baldwin, 1982; Bending and Read, 1996). Recently, realization of the beneficial qualities of dietary PAs for human health has increased the interest in these compounds (Bagchi et al., 2000; Dufresne and Farnworth, 2001). Simple monomeric and/or oligomeric PAs have been shown to possess anticancer, antioxidant and antimicrobial activities (Dixon et al., 2005).

Modest amounts of PAs in forages promote increased dietary protein nitrogen utilization and reduced occurrence of pasture bloat in ruminant animals such as cattle and sheep (Li et al., 1996; Aerts et al., 1999; Barry and McNabb, 1999). Pasture bloat occurs in ruminants when they are fed with a high protein diet such as alfalfa (lucerne; *Medicago sativa*) or clover (*Trifolium* spp), species that lack PAs in their aerial portions. The combination of excessive protein and methane released in the rumen from fermentation of the forage results in formation of a thick foam leading to bloating which, in severe cases, can be fatal. To combat pasture bloat, a common practice is to supplement the ruminant diet with surfactants, which break down the protein foams (Hall et al., 1994). Another remedy involves mixing high protein forage with forage known to contain moderate levels of PAs (Li et al., 1996). Both of these are costly options for the farmer or rancher, resulting in a reluctance to take advantage of the otherwise excellent nutritional qualities of alfalfa and clovers.

The building blocks of most PAs are (+)-catechin and (−)-epicatechin. (−)-Epicatechin has 2,3-cis stereochemistry and (+)-catechin has 2,3-trans-stereochemistry. These stereochemical differences are of major importance in PA biosynthesis, since all chiral intermediates in the flavonoid pathway up to and including leucoanthocyanidin are of the 2,3-trans stereochemistry, raising important questions about the origin of the 2,3-cis stereochemistry of (−)-epicatechin, the commonest extension unit in proanthocyanidins (Foo and Porter 1980). The most common anthocyanidins produced are cyanidin (leading to procyanidins) and delphinidin (leading to prodelphinidins). PAs may contain from 2 to 50 or more flavonoid units. PA polymers have complex structures because of variations in the flavonoid units and the sites for interflavan bonds. Depending on their chemical structure and degree of polymerization, PAs may or may not be soluble in aqueous organic solvents.

PAs are attracting increasing attention due to their ability to affect the nutritional quality of human and animal food (Bagchi et al., 2000; Barry and McNabb, 1999; Morris and Robbins, 1997). In addition, PAs and anthocyanins from various plants have beneficial effects on cardiac health and immune responses (Pataki et al., 2002; Foo et al., 2000; Lin et al., 2002), and to prevent macular degeneration (e.g. Brevetti et al., 1989; Lee et al., 2005). PAs can reversibly bind to proteins and reduce their degradation rate. The presence of moderate amounts of PAs in forage crops reduces the initial rate of microbial digestion of the protein component of forage material in the rumen. The protein-PA complexes then pass to the abomasum where they dissociate at the lower pH, providing "by-pass protein" for utilization by the animal and consequent enhancement of milk and wool production and live weight gain (Barry and McNabb, 1999; Tanner et al., 1995).

In addition, low concentrations of PA can help counter intestinal parasites in lambs, and confer bloat safety, presumably by interacting with both leaf protein and microbial enzymes such that the rate of protein degradation in the rumen is reduced (Aerts et al 1999). These properties of PAs underscore the potential importance of methods of engineering PA synthesis in crops, including forage crops in particular.

In addition, it has been shown that the presence of PAs in forage crops significantly reduces emission of the greenhouse gas methane by farm animals. Farm animals have been shown to produce large amounts of methane (~80 kg/yr/cow). Furthermore, PAs also preserve proteins during the ensiling process, increasing the feed value of silage and reducing the amount of nitrogen that is lost to the environment as feedlot waste (Albrecht and Muck, 1991; Reed, 1995). In laboratory studies, treatment of feed proteins with modest amounts of PAs (around 2-4% of dry matter) reduced proteolysis during both ensiling and rumen fermentation. In studies performed with sheep in New Zealand, increasing dietary PAs from trace amounts to 4% of dry matter increased by-pass protein, and a diet containing only 2% PAs strongly increased absorption of essential amino acids by the small intestine by up to 60% (Douglas et al. 1999).

An attractive alternative for forage improvement lies in genetically transferring the capability to synthesize PAs to non PA-accumulators (e.g. see WO 06/010096 or US Publication 2006/0123508). Since the precursors for PAs are the same as those for the production of anthocyanins, one approach is to transform plants with a transcription factor which, when ectopically expressed, induces anthocyanin production. Co-expression of one or more PA-specific biosynthetic enzymes such as anthocyanidin reductase (ANR), which converts cyanidin to the flavan-3-ol (−)-epicatechin, a building block of PAs (FIGS. 1-2) (Dixon et al., 2005), may then lead to PA accumulation (Xie et al., 2006).

However, there are several technical problems with this approach. First, apart from enzymes converting anthocyanin pathway precursors to catechin and epicatechin (US Publication 20040191787; Tanner et al., 2003; Xie et al., 2003; US Publication 20060123508), two potential transporters (Debeaujon et al., 2001; Kitamura et al., 2004), and an oxidase that likely acts on polymerized products (Pourcel et al., 2005), little is known of the proteins necessary for polymerization of tannins and their ultimate accumulation in vacuoles or cell walls (Dixon et al., 2005; Xie and Dixon, 2005). Second, transcription factors controlling anthocyanin production appear to be species-specific. Whereas the *Arabidopsis thaliana* producer of anthocyanin pigmentation (AtPAP1) MYB transcription factor (GenBank Accession AF325123) effectively induces anthocyanin production in *Arabidopsis* and tobacco (Borevitz et al., 2000), it does not function in alfalfa or white clover (see below). Similarly, expression of the maize Lc gene in alfalfa only resulted in anthocyanin production if the plants were exposed to strong abiotic stress (Ray et al., 2003). Expression of maize Lc Myc in conjunction with other transcription factors in *Arabidopsis* could lead to premature necrosis and death of the plants (Sharma and Dixon, 2005). Finally, even if anthocyanin production and downstream enzymes (for PA synthesis) are expressed, tannins have not necessarily accumulated, as seen in *Arabidopsis* expressing multiple flavonoid-pathway transcription factors (Sharma and Dixon, 2005).

The foregoing studies have provided a further understanding of the mechanisms and manipulation of plant secondary metabolism. However, the prior art has failed to provide techniques for the application of this understanding to the creation of plants having valuable new characteristics. What are thus needed are practical techniques for the production of novel plants with improved phenotypes and methods for the use thereof. Such techniques may allow the creation and use of plants with improved nutritional quality, thereby benefiting both human and animal health and representing a substantial benefit in the art.

SUMMARY OF THE INVENTION

In one aspect, the invention provides an isolated nucleic acid sequence that encodes a polypeptide that activates anthocyanin or proanthocyanidin biosynthesis, or its complement. In certain embodiments, the nucleic acid sequence is operably linked to a heterologous promoter. In one embodiment, the nucleic acid sequence is further defined as selected from the group consisting of: (a) a nucleic acid sequence encoding the polypeptide sequence of SEQ ID NO:5, SEQ ID NO:6, SEQ ID NO:7, SEQ ID NO:8, or SEQ ID NO:10; (b) a nucleic acid sequence comprising a sequence selected from the group consisting of SEQ ID NO:1, SEQ ID NO:2, SEQ ID NO:3, SEQ ID NO:4, or SEQ ID NO:9; (c) a nucleic acid sequence that hybridizes to any of SEQ ID NO:1, SEQ ID NO:2, SEQ ID NO:3, SEQ ID NO:4, or SEQ ID NO:9 under conditions of 1×SSC and 65° C., or higher stringency, and encodes a polypeptide that activates anthocyanin or proanthocyanidin biosynthesis; (d) a nucleic acid sequence encoding a polypeptide with at least 85% amino acid identity to any of SEQ ID NO:5, SEQ ID NO:6, SEQ ID NO:7, SEQ ID NO:8, or SEQ ID NO:10 that activates anthocyanin or proanthocyanidin biosynthesis; (e) a nucleic acid sequence with at least 85% identity to any of SEQ ID NO:1, SEQ ID NO:2, SEQ ID NO:3, SEQ ID NO:4, or SEQ ID NO:9; and (f) a complement of a sequence of (a)-(e). In certain embodiments, the isolated nucleic acid sequence may be operably linked to a heterologous promoter.

A recombinant vector comprising such an isolated nucleic acid sequence is also an embodiment of the invention, and may further comprise at least one additional sequence chosen from the group consisting of: a regulatory sequence, a selectable marker, a leader sequence and a terminator. In certain embodiments, the additional sequence is a heterologous sequence encoding an anthocyanin or proanthocyanidin biosynthesis activity, for instance selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), an anthocyanidin glycosyltransferase (GT), or AtPAP1 (production of anthocyanin pigment).

The recombinant vector may comprise a promoter, wherein the promoter is a plant developmentally-regulated, organelle-specific, inducible, tissue-specific, constitutive, or cell-specific promoter. In certain embodiments, the recombinant vector may be defined as an isolated expression cassette.

In another aspect, the invention provides an isolated polypeptide having at least 85% amino acid identity to the amino acid sequence of SEQ ID NO:5, SEQ ID NO:6, SEQ ID NO:7, SEQ ID NO:8, or SEQ ID NO:10, or a fragment thereof, having anthocyanin or proanthocyanidin biosynthesis activity. In particular embodiments, the isolated polypeptide comprising the amino acid sequence of SEQ ID NO:5, SEQ ID NO:6, SEQ ID NO:7, SEQ ID NO:8, or SEQ ID NO:10, or a fragment thereof, having anthocyanin or proanthocyanidin biosynthesis activity.

In yet another aspect, the invention provides a transgenic cell, including a bacterial cell, fungal cell, or plant cell transformed with a nucleic acid selected from the group consisting of: (a) a nucleic acid sequence encoding the polypeptide sequence of SEQ ID NO:5, SEQ ID NO:6, SEQ ID NO:7, SEQ ID NO:8, or SEQ ID NO:10; (b) a nucleic acid sequence comprising a sequence selected from the group consisting of SEQ ID NO:1, SEQ ID NO:2, SEQ ID NO:3, SEQ ID NO:4, or SEQ ID NO:9; (c) a nucleic acid sequence that hybridizes to any of SEQ ID NO:1, SEQ ID NO:2, SEQ ID NO:3, SEQ ID NO:4, or SEQ ID NO:9 under conditions of 1×SSC and 65° C., or higher stringency, and encodes a polypeptide that activates anthocyanin or proanthocyanidin biosynthesis; (d) a nucleic acid sequence encoding a polypeptide with at least 85% amino acid identity to any of SEQ ID NO:5, SEQ ID NO:6, SEQ ID NO:7, SEQ ID NO:8, or SEQ ID NO:10 that activates anthocyanin or proanthocyanidin biosynthesis; (e) a nucleic acid sequence with at least 85% identity to any of SEQ ID NO:1, SEQ ID NO:2, SEQ ID NO:3, SEQ ID NO:4, or SEQ ID NO:9; and (f) a complement of a sequence of (a)-(e). In certain embodiments, the invention provides a plant, or a plant part such as a foliar portion of a plant, a root, or a plant seed, comprising such a nucleic acid sequence. The isolated nucleic acid sequence may be operably linked to a heterologous promoter functional in a plant cell. In certain embodiments, the plant is a legume plant. In particular embodiments, the plant is a *Medicago* sp. plant, such as an alfalfa plant.

The transgenic plant, such as a *Medicago* plant, may express the selected nucleic acid and exhibit increased proanthocyanidin and/or anthocyaninbiosynthesis in selected tissues relative to those tissues in a second plant that differs from the transgenic plant only in that the selected nucleic acid is absent. In certain embodiments, the transgenic plant may be defined as transformed with a selected DNA encoding a LAP1, LAP2, LAP3, or LAP4 polypeptide selected from the group consisting of SEQ ID NO:5, SEQ ID NO:6, SEQ ID NO:7, SEQ ID NO:8, or a fragment thereof, having anthocyanin or proanthocyanidin biosynthesis activity.

In other embodiments, the transgenic plant may further be defined as transformed with a selected DNA sequence complementary to a sequence encoding a glycosyltransferase active in anthocyanin biosynthesis. The transgenic plant may comprise a selected DNA sequence comprising the complement of SEQ ID NO:10, or a fragment thereof. In another embodiment, the transgenic plant may be further defined as transformed with a DNA sequence encoding the polypeptide of SEQ ID NO:1.

In certain embodiments, the transgenic plant of is further defined as a crop plant, including a forage crop plant. In particular embodiments, the transgenic plant may be a forage legume, such as alfalfa (*Medicago sativa*), barrel medic (*Medicago truncatula*), sweetclover (*Melilotus* sp.), white clover, red clover, alsike clover, milkvetch, crownvetch, birdsfoot trefoil, pea (*Pisum sativum*), lentil (*Lens culinaris*), or soybean, among others.

In other embodiments, the plant may further be defined as comprising a transgenic coding sequence that encodes an anthocyanin or proanthocyanidin biosynthesis activity selected from the group consisting of: phenylalanine ammonia-lyase (PAL), cinnamate 4-hydroxylase (C4H), 4-coumarate:CoA ligase (4CL), chalcone synthase (CHS), chalcone isomerase (CHI), flavanone 3-hydroxylase (F3H), dihydroflavonol reductase (DFR), anthocyanidin synthase (ANS), leucoanthocyanidin reductase (LAR), anthocyanidin reductase (ANR), an anthocyanidin glucosyltransferase (GT), or AtPAP1 (production of anthocyanin pigment). In particular embodiments, the transgenic coding sequence may encode an anthocyanidin reductase (ANR) polypeptide, for instance selected from the group consisting of SEQ ID NO:43, SEQ ID NO:44, SEQ ID NO:45, and SEQ ID NO:46.

The transgenic plant may further comprise a transgenic sequence that down-regulates expression of a glycosyltransferase active in the synthesis of an anthocyanin. In a particular embodiment, the transgenic sequence may down-regulate expression of UGT78G1, for instance comprising the complement of SEQ ID NO:9 or a fragment thereof.

The transgenic plant may be a fertile $R_0$ transgenic plant, or a progeny plant of any generation of a fertile $R_0$ transgenic plant, wherein the transgenic plant comprises the selected DNA. A seed of such a transgenic plant comprising a nucleic acid selected from the group consisting of: (a) a nucleic acid sequence encoding the polypeptide sequence of SEQ ID NO:5, SEQ ID NO:6, SEQ ID NO:7, SEQ ID NO:8, or SEQ ID NO:10; (b) a nucleic acid sequence comprising a sequence selected from the group consisting of SEQ ID NO:1, SEQ ID NO:2, SEQ ID NO:3, SEQ ID NO:4, or SEQ ID NO:9; (c) a nucleic acid sequence that hybridizes to any of SEQ ID NO:1, SEQ ID NO:2, SEQ ID NO:3, SEQ ID NO:4, or SEQ ID NO:9 under conditions of 1×SSC, and 65° C., and encodes a polypeptide that activates anthocyanin or proanthocyanidin biosynthesis; (d) a nucleic acid sequence encoding a polypeptide with at least 85% amino acid identity to any of SEQ ID NO:5, SEQ ID NO:6, SEQ ID NO:7, SEQ ID NO:8, or SEQ ID NO:10 that activates anthocyanin or proanthocyanidin biosynthesis; (e) a nucleic acid sequence with at least 85% identity to any of SEQ ID NO:1, SEQ ID NO:2, SEQ ID NO:3, SEQ ID NO:4, or SEQ ID NO:9; and (f) a complement of a sequence of (a)-(e), is also provided, as are cells of such a plant.

Another aspect of the invention provides a method of producing a plant with increased proanthocyanidin biosynthesis, comprising introducing into the plant a selected DNA encoding a sequence that promotes anthocyanin biosynthesis, such as a LAP polypeptide, wherein the coding sequence is operably linked to a promoter functional in the plant and wherein the plant comprises increased anthocyanin biosynthesis in aerial portions of the plant relative to a second plant that differs from the plant only in that the selected DNA is absent in the second plant. The DNA may be selected from the group consisting of: (a) a nucleic acid sequence encoding the polypeptide sequence of SEQ ID NO:5, SEQ ID NO:6, SEQ ID NO:7, or SEQ ID NO:8; (b) a nucleic acid sequence comprising a sequence selected from the group consisting of SEQ ID NO:1, SEQ ID NO:2, SEQ ID NO:3, or SEQ ID NO:4; (c) a nucleic acid sequence that hybridizes to any of SEQ ID NO:1, SEQ ID NO:2, SEQ ID NO:3, or SEQ ID NO:4 under conditions of 1×SSC, and 65° C., and encodes a polypeptide that activates anthocyanin or proanthocyanidin biosynthesis; (d) a nucleic acid sequence encoding a polypeptide with at least 85% amino acid identity to any of SEQ ID NO:5, SEQ ID NO:6, SEQ ID NO:7, or SEQ ID NO:8 that activates anthocyanin or proanthocyanidin biosynthesis; (e) a nucleic acid sequence with at least 85% identity to any of SEQ ID NO:1, SEQ ID NO:2, SEQ ID NO:3, or SEQ ID NO:4; and (f) a complement of a sequence of (a)-(e).

The selected DNA may be introduced into the plant by plant breeding. Alternatively, the selected DNA may be introduced into the plant by genetic transformation of the plant. The plant may be a legume, such as a forage legume, including alfalfa, and the method may further comprise preparing a transgenic progeny plant of any generation of the plant, wherein the progeny plant comprises the selected DNA.

In another aspect, the present invention provides a method of making food or feed for human or animal consumption, and comprises (a) obtaining a transgenic plant comprising a selected transgene DNA, wherein the selected DNA enhances proanthocyanidin or anthocyanin synthesis; (b) growing the plant under plant growth conditions to produce plant tissue from the plant; and (c) preparing food or feed for human or animal consumption from the plant tissue. Preparing food may comprise harvesting the plant tissue, and the food may be, for instance, hay, silage, starch, protein, meal, seed, flour or grain.

A nutraceutical prepared by the method of: (a) obtaining a transgenic plant comprising a selected transgene DNA, wherein the selected DNA enhances proanthocyanidin or anthocyanin synthesis; (b) growing the plant under plant growth conditions to produce plant tissue from the plant; and (c) preparing a nutraceutical for human or animal consumption from the plant tissue; is also an aspect of the invention.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

6.2.1.12); CHS, chalcone synthase (E.C. 2.3.1.74); F3H, flavanone 3-hydroxylase (E.C. 1.14.11.9); DFR, dihydroflavonol reductase (E.C. 1.1.1.219); LAR, leucoanthocyanidin reductase (E.C. 1.17.1.3); ANS, anthocyanidin synthase (E.C. 1.14.11.19); ANR, anthocyanidin reductase (E.C. 1.3.1.77); AtPAP1 (production of anthocyanin pigment; MYB-type transcription factor from *Arabidopsis*); GT, anthocyanidin specific glycosyltransferase.

Figure 2:
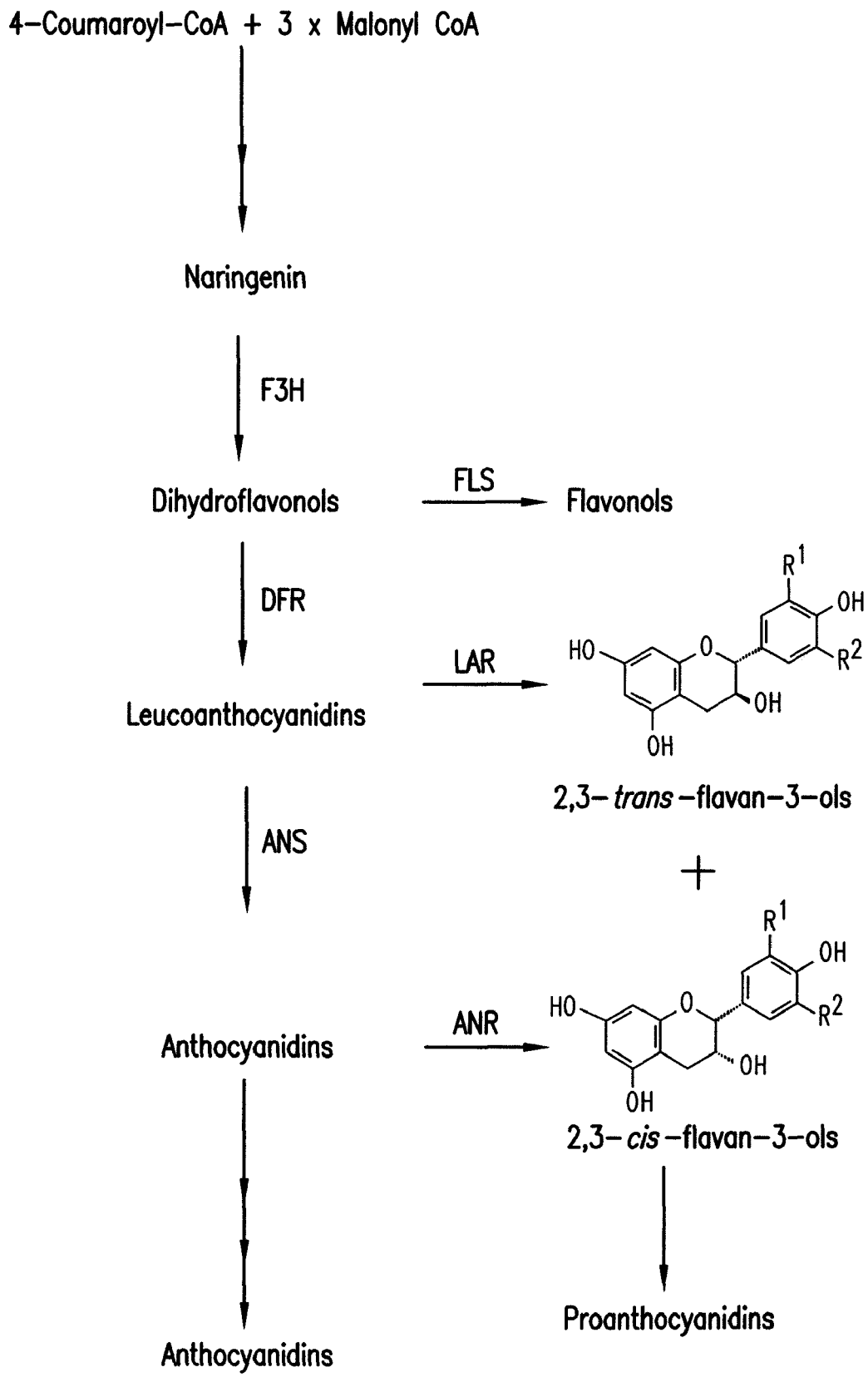

FIG. 2: Pathway to PAs, showing (+)-catechin and (−)-epicatechin monomers

FIG. 3: Visible phenotypes of transgenic plants ectopically expressing anthocyanin pathway regulatory genes. (A) *Medicago sativa* expressing AtPAP1 (right) or vector control (left); (B) a tobacco seedling expressing MtLAP1; (C) flowers from two independent MtLAP1-expressing tobacco lines (left, right) and a non-transformed control (center); (D) *M. truncatula* plants expressing GUS (left) or MtLAP1 (right); (E) higher magnification of leaves of *M. truncatula* plants expressing GUS (left) or MtLAP1 (right), showing seed pods; (F) *M. sativa* expressing MtLAP1 and MtANR; (G) *M. sativa* expressing MtANR and GUS; (H) *Trifolium repens* expressing MtLAP1; (I) untransformed *T. repens* control FIG. 4: Sequence comparisons of anthocyanin-regulatory transcription factors. (A) Multiple sequence alignment of published transcription factors involved in anthocyanin production and deduced amino acid sequences for *Medicago truncatula* LAP1 homologs or other sequences (SEQ ID NOs:5-8; SEQ ID NOs:95-96; SEQ ID NO:97 (i.e. the peptide encoded by SEQ ID NO:18)). R3/R2 conserved Myb domains are underlined. An2, Petunia An2 MYB regulator of anthocyanin production (SEQ ID NO:96 encoded within SEQ ID NO:94; Quattrochio et al., 1999;); Antho1, tomato Anthocyanin 1 MYB regulator of anthocyanin production (SEQ ID NO:95; encoded within SEQ ID NO:93; Mathews et al., 2003); consensus sequence (SEQ ID NO:98); (B) phylogenetic tree of selected anthocyanin regulatory transcription factors. Distances are nucleotide substitutions.

Figure 5:

FIG. 5: Pigmentation of *M. sativa* leaf transformed with MtLAP2 (on right) compared to control non-transgenic leaf on left.

FIG. 6: Anthocyanin production in *M. truncatula* ectopically expressing MtLAP1. (A) Levels of total anthocyanins in leaves of independent transgenic *M. truncatula* plants expressing MtLAP1 or GUS (control), or co-expressing MtLAP1 with MtANR or GUS (control); (B) HPLC analysis of methanolic extracts from *M. truncatula* leaves expressing MtLAP1 (upper trace) and GUS control (lower trace); (C) HPLC trace of acid hydrolyzed anthocyanin extract from *M. truncatula* leaves expressing MtLAP1 or GUS; (D) HPLC trace of acid-hydrolyzed anthocyanin extract from *M. sativa* leaves co-expressing MtLAP1 and MtANR, or GUS and MtANR. The major peak at 33 min is cyanidin.

FIG. 7: (A) LC-MS analysis of anthocyanins from leaf tissue of alfalfa co-expressing MtLAP1 and MtANR. Insets show UV-Visible spectrum for the major peak eluting at 15.8 min (B), and the MS/MS fragmentation pattern (C), showing ions at M/z 449 and 287 derived from the parent ion of M/z 625 (D). The compound consists of a cyanidin backbone conjugated with a hexose and a glucuronic acid residue (tentative structure shown).

Figure 8:
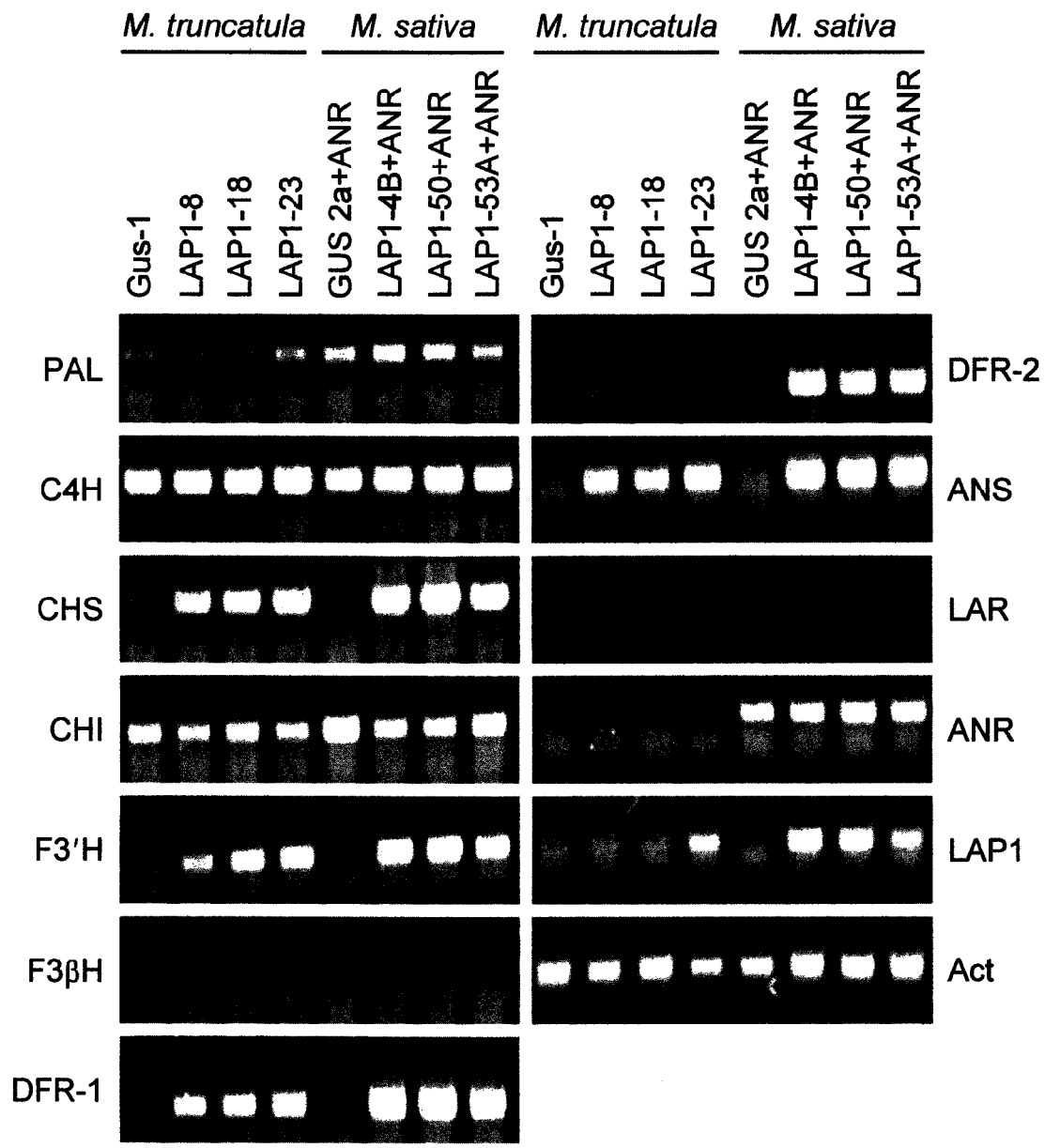
Figure 9A:
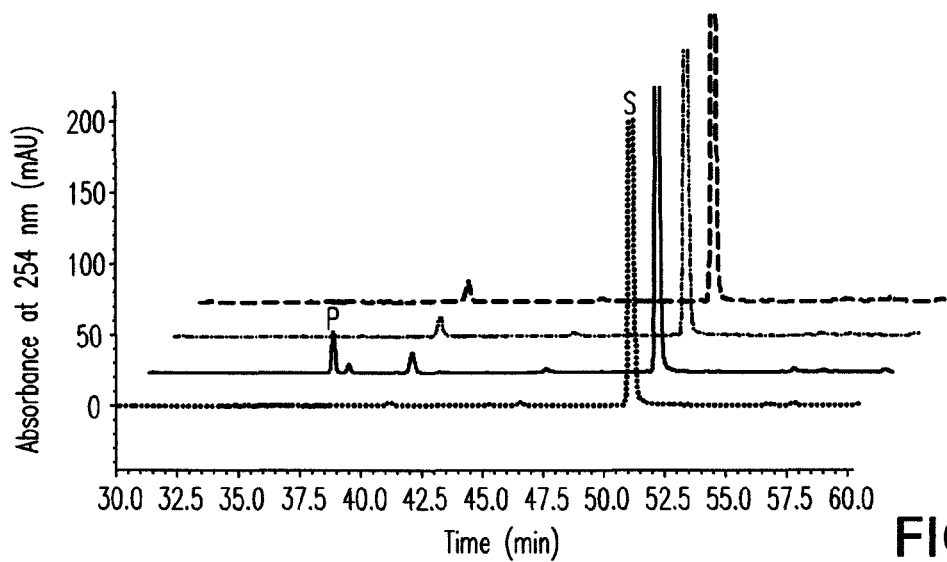
Figure 9B:
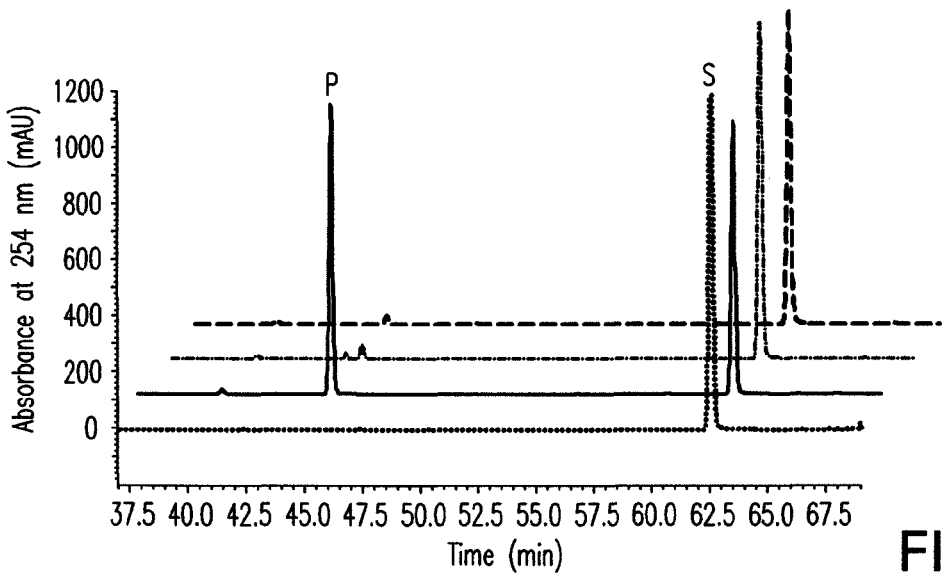
Figure 9C:
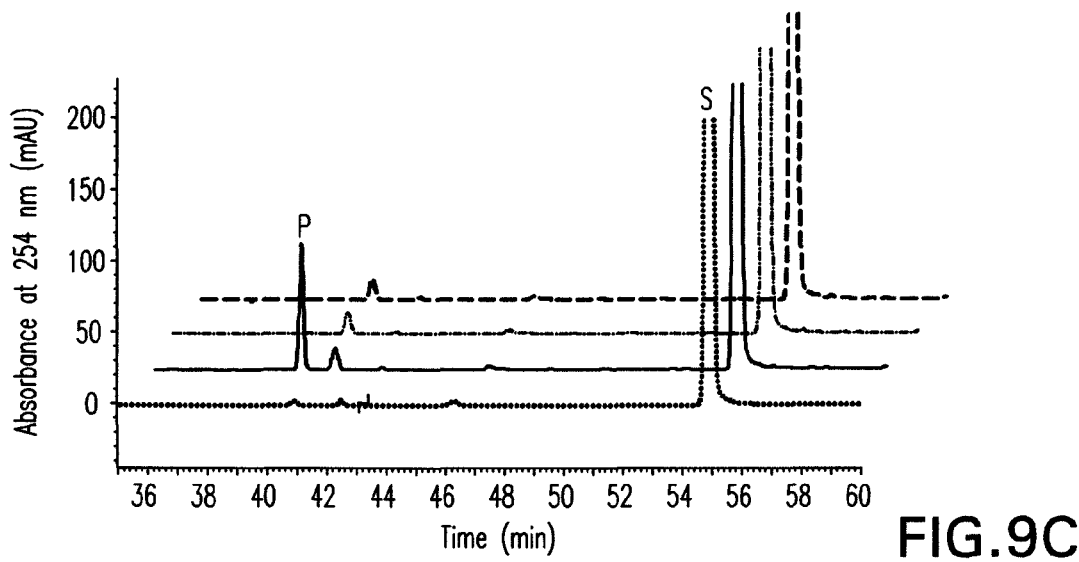
Figure 9D:
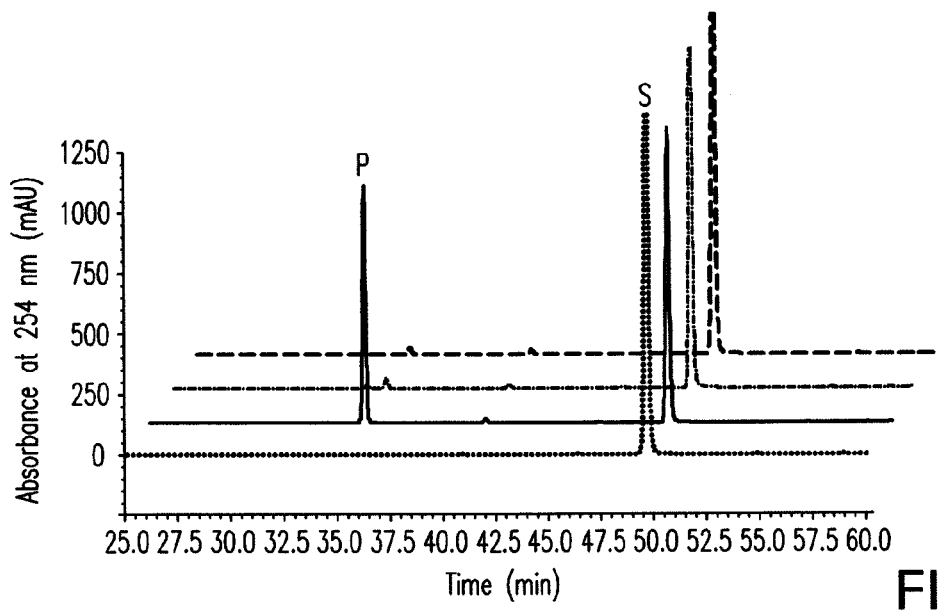
Figure 9E:
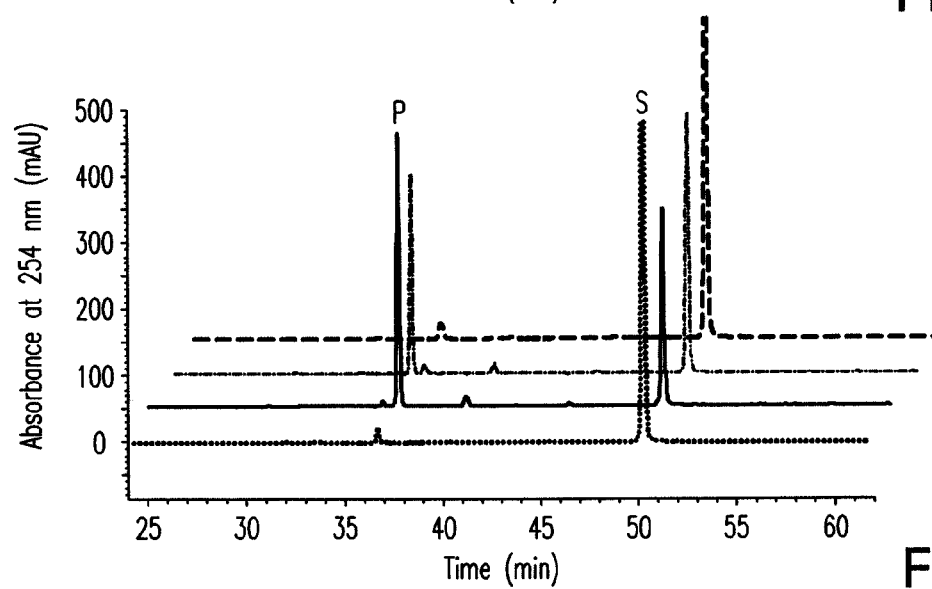
Figure 9F:
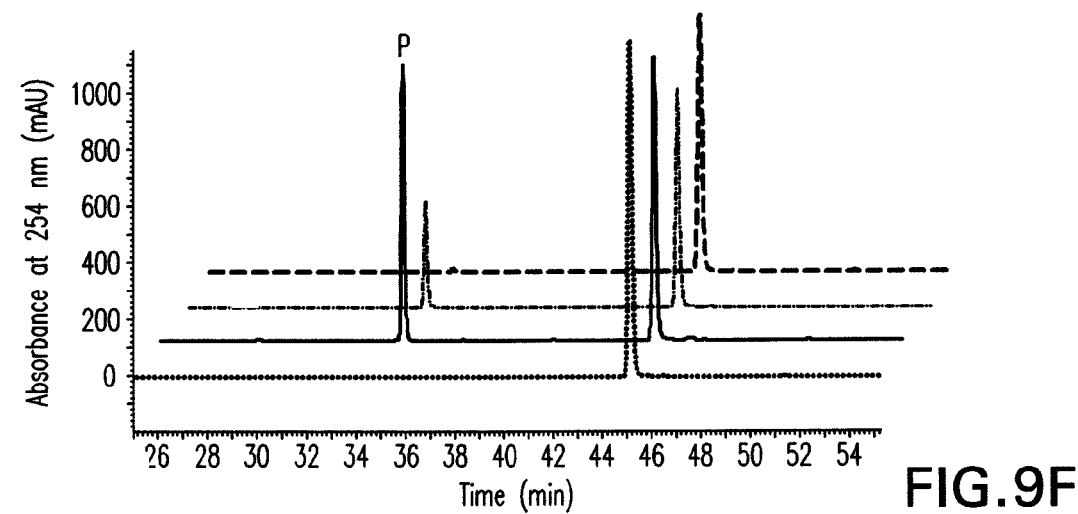
Figure 9G:
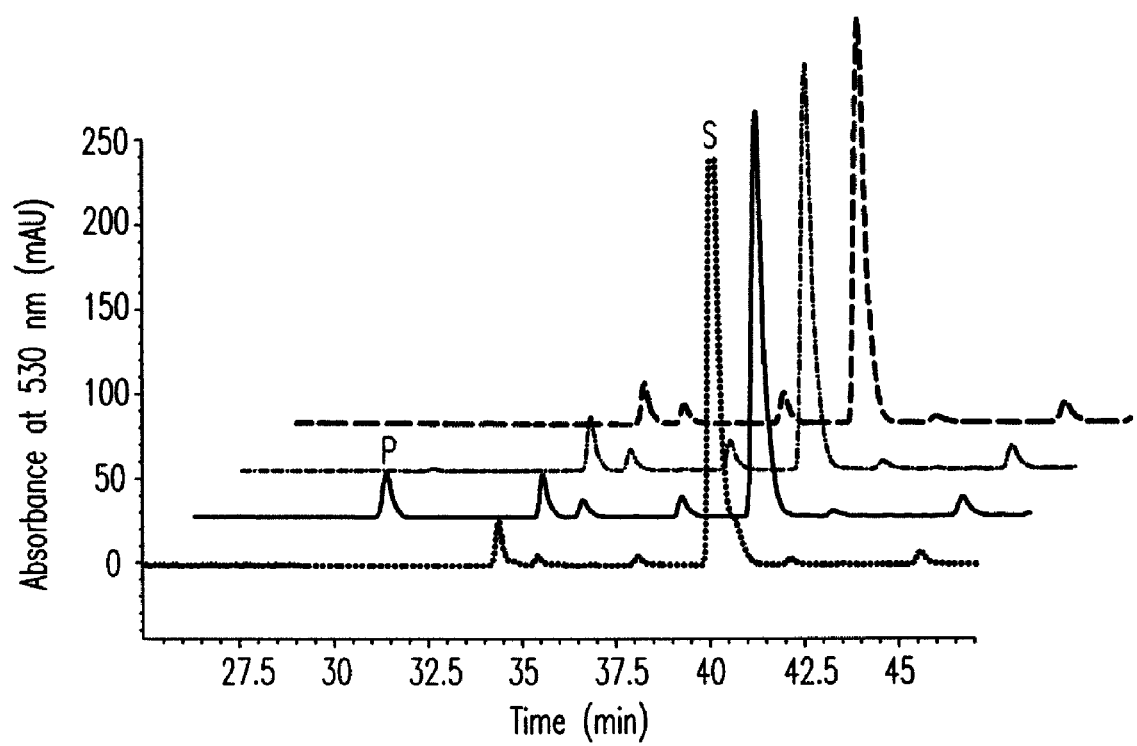

FIG. 8: RT-PCR analysis of expression levels of anthocyanin/PA biosynthetic genes in *M. truncatula* and alfalfa (*M. sativa*) leaf tissues. Plants were transformed with GUS (control), MtLAP (*M. truncatula*) or MtLAP and MtANR (*M. sativa*). PAL, L-phenylalanine ammonia-lyase; C4H, cinnamate 4-hydroxylase; 4CL, 4-coumarate CoA ligase; CHS, chalcone synthase; CHI chalcone isomerase; F3'H, flavanone 3'-hydroxylase; F3H, flavanone 3-hydroxylase; DFR-1, dihydroflavonol reductase-1; DFR-2 dihydroflavanol reductase-2; ANS, anthocyanidin synthase; LAR, leucoanthocyanidin reductase, ANR, anthocyanidin reductase; LAP1, Legume anthocyanin production, Act, actin (loading control).

FIG. 9: HPLC analysis of substrates and products from incubations of (iso)flavonoids with UGT78G1 in the presence of different sugar donors. Reactions containing substrate (250 µM), UDP-sugar (2.5 µM), and UGT78G1 (1.25 µg) were incubated for 3 h at 30° C. (A) apigenin as acceptor substrate; (B) biochanin A; (C) formononetin; (D) genistein; (E) kaempferol; (F) quercetin; (G) pelargonidin. S, substrate; P, product. Dotted lines, reactions incubated without enzyme; solid black lines, reactions incubated in the presence of UGT78G1 and UDPG; dashed-dotted lines, reactions incubated in the presence of UGT78G1 and UDP-galactose; dashed lines, reactions incubated in the presence of UGT78G1 and UDP-glucuronic acid.

Figure 10:
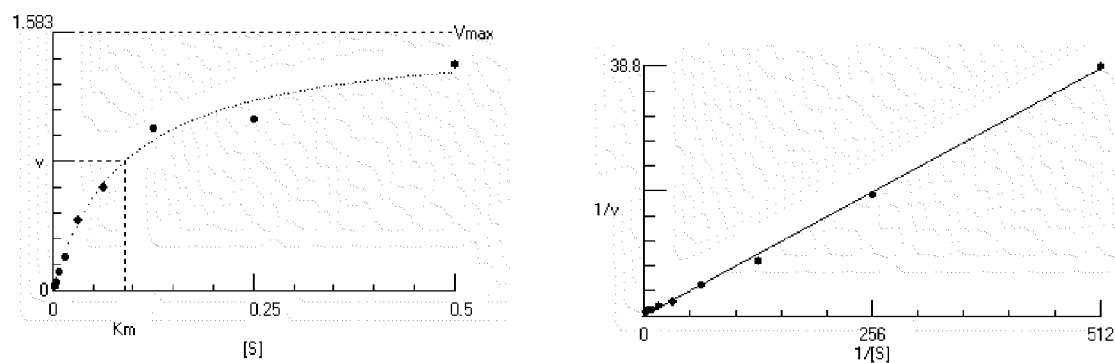

FIG. 10: Michaelis-Menten hyperbola and Lineweaver-Burk plot for UGT78G1 with kaempferol as substrate. Substrate concentration (S) and velocity (v) are given in mM and µM/min, respectively. Donor was UDPG.

Figure 11:
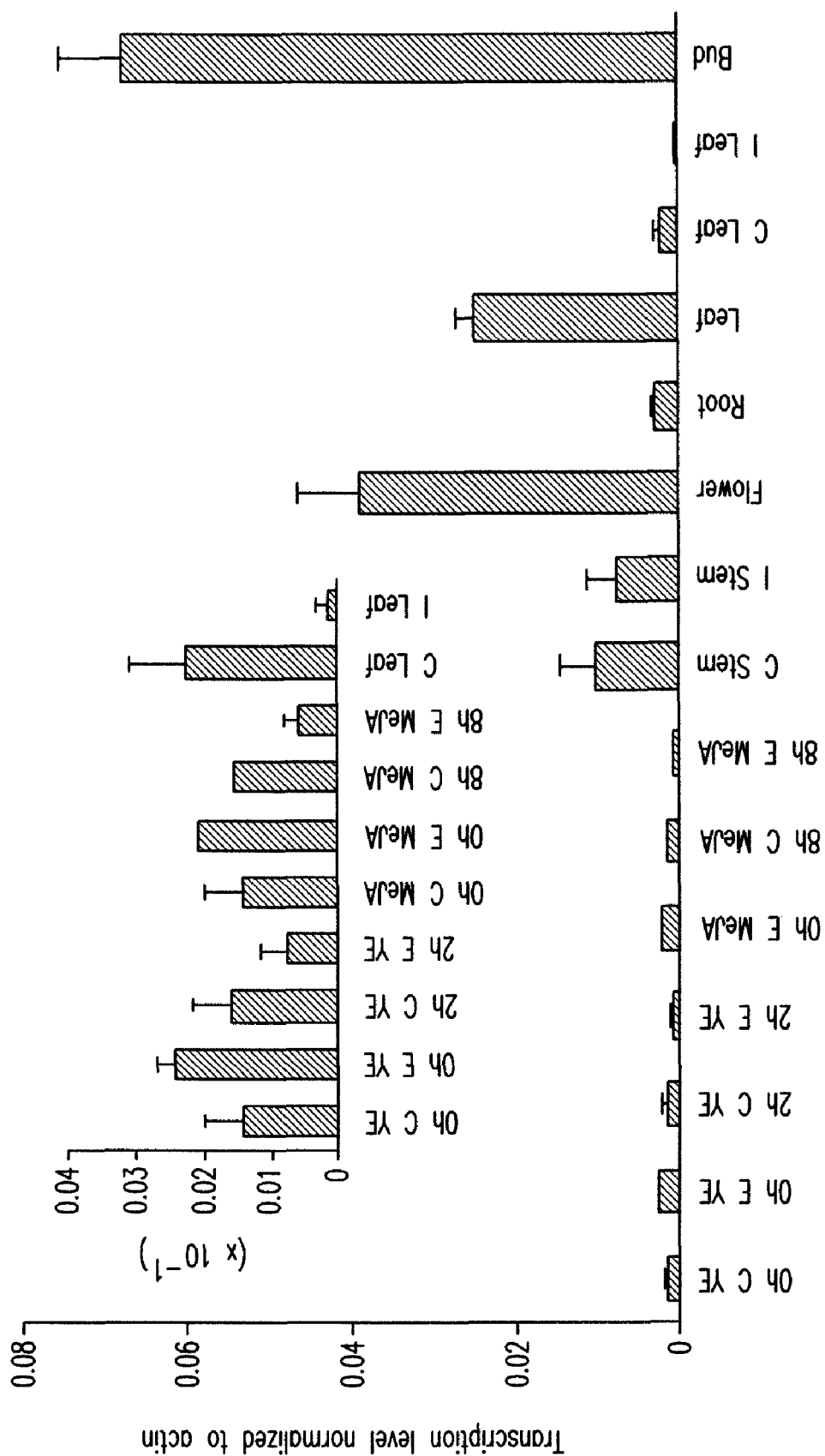

FIG. 11: Transcript levels of UGT78G1 in *M. truncatula* tissues and cell cultures quantified by qRT-PCR. Cell cultures were elicited with yeast elicitor (E) or methyl jasmonate (MeJA) for 2 h and 8 h, respectively. Roots, leaves and buds were harvested from unchallenged plants. Leaves were also wounded (C), and then inoculated (I) with a suspension of *Phoma medicaginis* for 72 h (E). Stems were sprayed with a solution of 0.1% Tween 20 (C) or with a spore suspension of *P. medicaginis* in Tween 20 (I). cDNAs obtained from RT-PCR were quantified relative to the abundance of actin. Inset shows transcript levels in cell suspension cultures or inoculated leaves in cases where they were significantly lower than in the other organs.

FIG. 12: Production of oligomeric PAs in leaf tissues of plants expressing MtLAP1. (A) Normal phase HPLC chromatogram showing DMACA-reactive PA monomer and oligomer peaks (post-column derivatization) from leaves of *Desmodium uncinatum* (upper trace) and from alfalfa expressing AtTT2 (lower trace). (B) Normal phase HPLC chromatogram showing DMACA-reactive PA monomer and oligomer peaks (post-column derivatization) from *M. truncatula* leaves expressing MtLAP 1 (upper trace) or GUS (control, lower trace). (C) Normal phase HPLC chromatogram showing DMACA-reactive PA monomer and oligomer peaks (post-column derivatization) from alfalfa leaves co-expressing MtLAP1 and MtANR (upper trace), or GUS and MtANR (control, lower trace). (D) PA levels in leaves of independent transformants of *M. truncatula* expressing MtLAP1 or GUS (control) and alfalfa (*M. sativa*) co-expressing MtLAP1 and MtANR, or GUS and MtANR (control). Values, determined by microplate assay with DMACA reagent, are the means and SDs of triplicate independent samples from each line.

Figure 13:
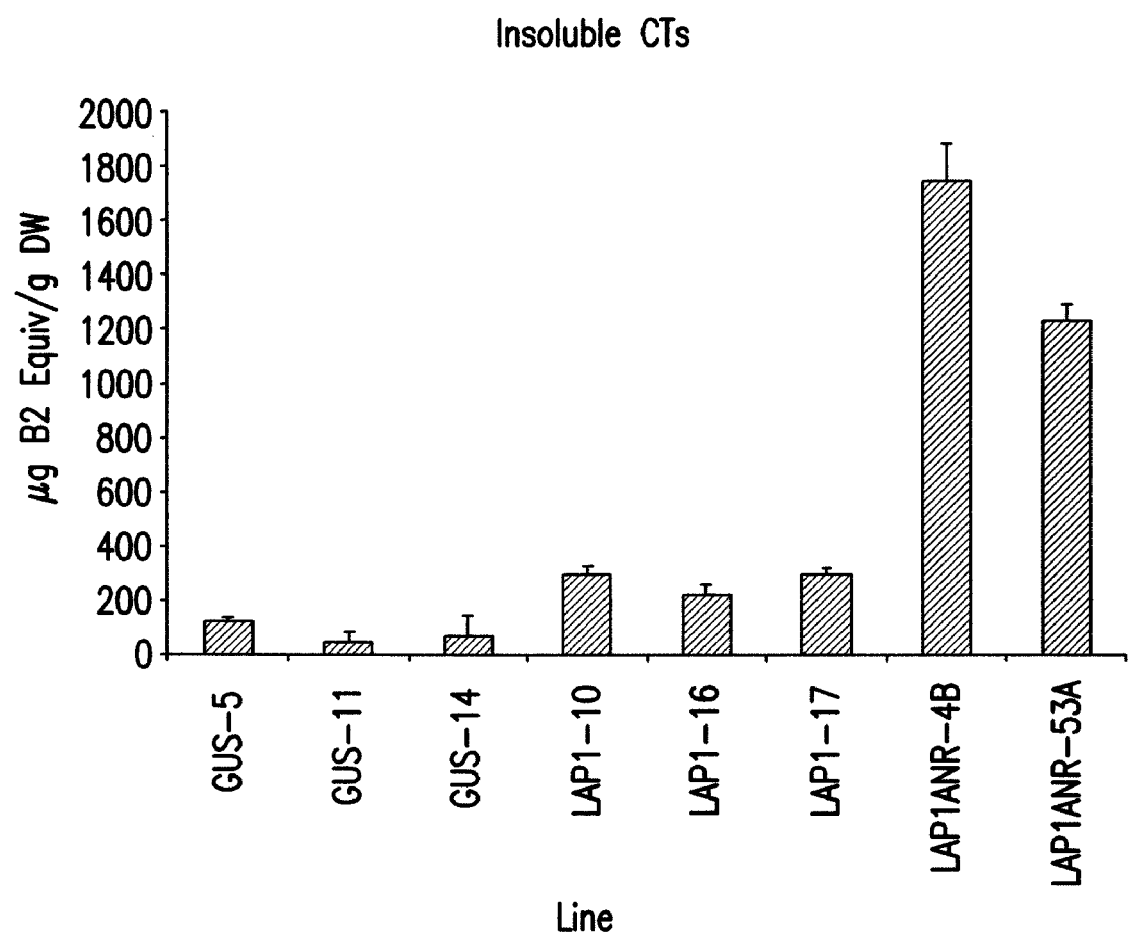

FIG. 13: Insoluble proanthocyanidin levels in transgenic alfalfa plants expressing β-glucuronidase (GUS, control), *Medicago* LAP1 alone, or *Medicago* LAP1 and *Medicago* ANR. Each bar represents an independent transformants, indicating mean and standard deviation from 3 analytical replicates.

DETAILED DESCRIPTION OF THE INVENTION

The invention overcomes the limitations of the prior art by providing methods and compositions for the modification of anthocyanin and proanthocyanidin (PA) metabolism in plants, specifically in legumes. The invention has numerous important applications to agriculture. The invention allows, for the first time, the production of anthocyanin or PA in legume plants or plant tissues that otherwise lack significant anthocyanin or PA content, including, for example, aerial portions of alfalfa plants. By introduction of a transgene encoding an anthocyanin transcription factor functional in legumes such as a LAP (legume anthocyanin production) gene, e.g. encoding LAP1, LAP2, LAP3, or LAP4 (nucleotide and amino acid sequences shown in SEQ ID NOs:1-8), into a plant otherwise lacking the gene, the production and accumulation of PA can be induced.

It is shown herein that constitutive expression of the *Medicago truncatula* LAP1 transcription factor in alfalfa surprisingly results in accumulation of significant levels of polymeric proanthocyanidins in aerial portions of alfalfa including foliage that do not normally express PAs (e.g. FIGS. 3, 5). This is unexpected given that constitutive expression of the TT2 transcription factor in alfalfa only leads to very low levels of PA accumulation. Therefore, the effects of LAP1 over-expression on PA accumulation in *Medicago sativa* could not have been predicted based on studies in *Arabidopsis*.

Alfalfa lacks significant levels of PAs in the aerial portions, although high levels are found in the seed coat (Koupai-Abyazani et al., 1993), and DMACA-reactive material that may represent PAs is also present in trichomes of glandular haired varieties (Aziz et al., 2005). To date, classical breeding approaches have failed to introduce PAs into alfalfa foliage, and it has been accepted that this problem will likely require a biotechnological solution (Lees, 1992). As the anthocyanin precursors of PAs are also essentially absent from unstressed alfalfa foliage, introducing the PA trait requires increasing, or introducing de novo, the activities of at least ten known biosynthetic enzymes, plus a requirement for several additional functions associated with transport and sequestration of intermediates and products.

Although ectopic expression of certain transcription factors can lead to anthocyanin production, this strategy has been problematical in alfalfa. As described in Example 1, the *Arabidopsis* PAP 1 transcription factor, which induces anthocyanin levels of up to 1.34 mg per g fresh weight in transgenic tobacco leaves, completely fails to induce anthocyanins in alfalfa. A previous attempt to engineer PAs in alfalfa utilized expression of the maize Lc MYC transcription factor to induce anthocyanin production, in the absence of additional transgenes specific to the PA pathway (Ray et al., 2003). Levels of anthocyanins in Lc-expressing alfalfa lines were reported to reach up to 158 µg/g fresh weight (Ray et al., 2003), but these values were not stable or reproducible, and anthocyanin production appeared to require exposure of the plants to abiotic stress, including continuous light for 36 to 48 h (Ray et al., 2003). Expression of the maize B-Peru MYC gene in white clover led to anthocyanin production restricted to the white crescent area of the leaf (deMajnik et al., 2000); however, expression of B-Peru in alfalfa failed to induce anthocyanin formation (Ray et al., 2003).

Transformation of alfalfa, *M. truncatula* or clover with a *Medicago* LAP gene as described herein results in stable, high-level anthocyanin production. For instance, the MtLAP1 gene was expressed under control of the 35S promoter, which is an inefficient constitutive promoter in legumes (Xiao et al., 2005). Thus, relatively low level expression of LAP1 (as seen from RT-PCR analysis) produces a strong anthocyanin phenotype in legumes associated with greatly increased transcription of anthocyanin biosynthetic genes. Anthocyanin levels in *M. truncatula* and alfalfa were approximately 10-fold higher than those reported in Lc-expressing alfalfa, and similar to those reported in tobacco expressing AtPAP1 (Xie et al., 2006). PA biosynthesis utilizes two intermediates of the anthocyanin pathway, leucoanthocyanidin for formation of (+)-catechin via leucoanthocyanidin reductase (LAR; Tanner et al., 2003), and anthocyanidin for formation of (−)-epicatechin via ANR (anthocyanidin reductase) (Xie et al., 2003). Both of these intermediates are unstable and do not accumulate to measurable levels in plants. Presumably, the over-expression of the anthocyanin pathway provides sufficient levels of these compounds to feed the LAR and/or ANR pathways for subsequent formation of PAs. Although LAR is not induced by LAP1 expression in alfalfa, it is interesting that small amounts of free catechin, as well as epicatechin, were observed in alfalfa leaves co-expressing LAP1 and ANR. PAs accumulated in leaves of alfalfa co-expressing LAP1 and ANR to levels of between 150-250 µg catechin equivalents per g fresh weight, well within the range for bloat protection. Similar PA levels were observed in tobacco plants co-expressing PAP1 and MtANR (Xie et al., 2006).

The studies described herein further show that PA levels of between 1-5 mg per g dry weight (approximately 100-500 µg/g fresh weight) can reduce rumenal methane production and thereby confer bloat reduction for ruminant animals fed alfalfa forage (Li et al., 1996). As cattle are a major source of methane release to the environment, successful engineering of a bloat-safe alfalfa is advantageous for both animal health and the environment. Higher levels of PAs (from 20-40 mg/g dry weight) are required to significantly increase by-pass protein levels (the protein that exits the rumen), with associated improvements in animal performance and reduction in nitrogen excretion (Aerts et al., 1999).

The present studies thus demonstrate the biotechnological development of a stable, bloat-resistant phenotype in alfalfa. They also suggest additional strategies for fine-tuning and improving the trait. To achieve higher levels of tannins beneficial for ruminant nitrogen nutrition, an increase in the anthocyanidin pool for synthesis of (−)-epicatechin may be achieved. Anthocyanidin may then accumulate as determined by the relative rates of reduction to epicatechin or glycosylation to anthocyanin. The microarray analysis results also identify UGT78G1 as being strongly up-regulated by LAP1 expression and therefore potentially involved in anthocyanin glycosylation. Down-regulation of UGT78G1 expression in LAP1:MtANR transgenics may therefore increase the pool of anthocyanidin available for PA formation.

Many forage crops are low in PAs, including *Medicago* spp such as alfalfa (*Medicago sativa*) and annual medics, white clover, ball clover, Persian clover, red clover, crimson clover, berseem clover, arrowleaf clover, alsike clover, subterranean clovers, fenugreek, and sweetclover (*Melilotus* spp.). Similarly, bloat can be caused by grazing of wheat pastures and other lush foliage such as fast-growing monocots. "Feedlot bloat" also occurs in cattle fed high-grain rations that may or may not contain legume forage, green-chopped legumes, or other finely ground feed. In these cases, direct engineering of PA accumulation in the forage plant may be used in accordance with the invention to prevent bloat. Further, PA modification could be engineered into feed components that are blended or added to bloat-causing components to reduce the bloat incidence in animals consuming the mixed feed.

One application of the invention is thus the modification of PA biosynthesis in plants with low PA content, resulting in plants, plant parts, or products such as silage or hay, with enhanced value. Alfalfa is one such plant. PAs are made in alfalfa (*Medicago sativa*), as in *Arabidopsis*, in the seed coat, but do not accumulate in the leaves (Koupai-Abyazani et al., 1993; Skadhauge et al., 1997). Nonetheless, alfalfa is the world's major forage legume. Therefore, introducing PA biosynthesis to the leaves or other tissues of alfalfa or other low PA plants would substantially improve the utility of this crop for feed by reduction of its potential for causing pasture bloat. Forage crops that accumulate PAs in leaves have low bloating potential; these include *Lotus corniculatus, Leucaena leucocephala, Hedysarum sulfurescens* and *Robinia* spp, among others.

Technology that could result in constitutive expression of PAs in high protein forage crops would also greatly improve the agronomic value of crops in addition to alfalfa. In addition, the potential importance of anthocyanins and PAs in human health makes methods for their facile production in plants necessary for the full development of their therapeutic potential, for instance allowing their production and use as nutraceuticals or as food colorants.

Over 100 genes are up-regulated in *M. truncatula* leaves in response to constitutive expression of LAP1, most of which are apparently involved in anthocyanin biosynthesis. Thus co-expressing LAP1 with anthocyanidin reductase (ANR), renders it possible to produce alfalfa foliage containing levels of oligomeric proanthocyanidins previously shown to be sufficient for pasture bloat prevention. The present invention provides methods and compositions for increasing PA production comprising introducing transgenic LAP coding sequences, e.g. LAP1. In certain aspects, this may be provided in combination with anthocyanidin reductase (ANR) coding sequences provided herein, which functions to direct precursors from the anthocyanin pathway into the formation of proanthocyanidins.

Further, as noted, microarray analysis of genes up-regulated by LAP1 also allowed for identification of a *Medicago* anthocyanidin glycosyltransferase. One glycosyltransferase gene, UGT78G1 (SEQ ID NO:9), that was strongly up-regulated by LAP1 in *M. truncatula* was shown to be active with anthocyanidins in vitro and is most probably the major *Medicago* anthocyanidin glycosyltransferase. Such glucosyltransferase genes, like the one encoding UGT78G1, thus are a target, in one aspect of the invention, for down-regulation to increase tannin levels in alfalfa co-expressing LAP1 and ANR.

When ANR from the model legume *Medicago truncatula*, a species closely related to alfalfa, is ectopically expressed in *M. truncatula* A17, the red pigmentation found naturally in the center of the leaves is reduced, accompanied by the production of modest amounts of oligomeric PAs (Xie et al., 2006). Thus, *Medicago* leaf tissue has the potential to accumulate PAs if provided with a supply of anthocyanidin precursor and at least one enzyme for production of flavan-3-ol monomers. The identification of a family of MYB transcription factor genes from *Medicago truncatula* which induce constitutive anthocyanin production when expressed in alfalfa, *M. truncatula* or white clover allows for production of anthocyanin and PAs in parts of alfalfa plants and at levels not previously reported. These LAP genes, in combination with ANR, may be used to engineer PAs in alfalfa to levels previously demonstrated to reduce pasture bloat.

I. Application of the Invention

As indicated above, one application of the invention is the introduction or increase of PA biosynthesis in plants. Such applications may result in forage improvement and nutritional improvement of foods. In accordance with the invention this may be carried out by introduction of LAP1 alone or in combination with other PA biosynthesis genes. The invention may be used to improve the nutritional quality of plants. Catechins and similar flavonoids have been reported to behave as strong antioxidants and have other properties which may make their consumption beneficial to human and animal health. Also, such compounds are generally antimicrobial, and their presence may improve food quality by preventing pre- and post-harvest damage. Accordingly, increases in PA biosynthesis may be used to achieve the associated health benefits.

Another use of the invention comprises the alteration of pigmentation in plant parts, including, but not limited to, flower color, seed coat color and leaf color. This can be achieved, for example, by increasing anthocyanin content via over-expression of legume anthocyanin production (LAP) genes, thereby allowing anthocyanin accumulation and the associated pigmentation of plant tissue. Accumulation of anthocyanins may simultaneously improve the nutritional, disease resistance, or herbivore resistance of the plant products. When expressed from a plant gene promoter that responds to a particular nutrient starvation (e.g. phosphate, nitrogen or sulfur depletion), LAP genes may serve as sensors for nutrient status, leading to increased coloration under nurtrient stress which can be documented by remote sensing in the field.

Figure 1:
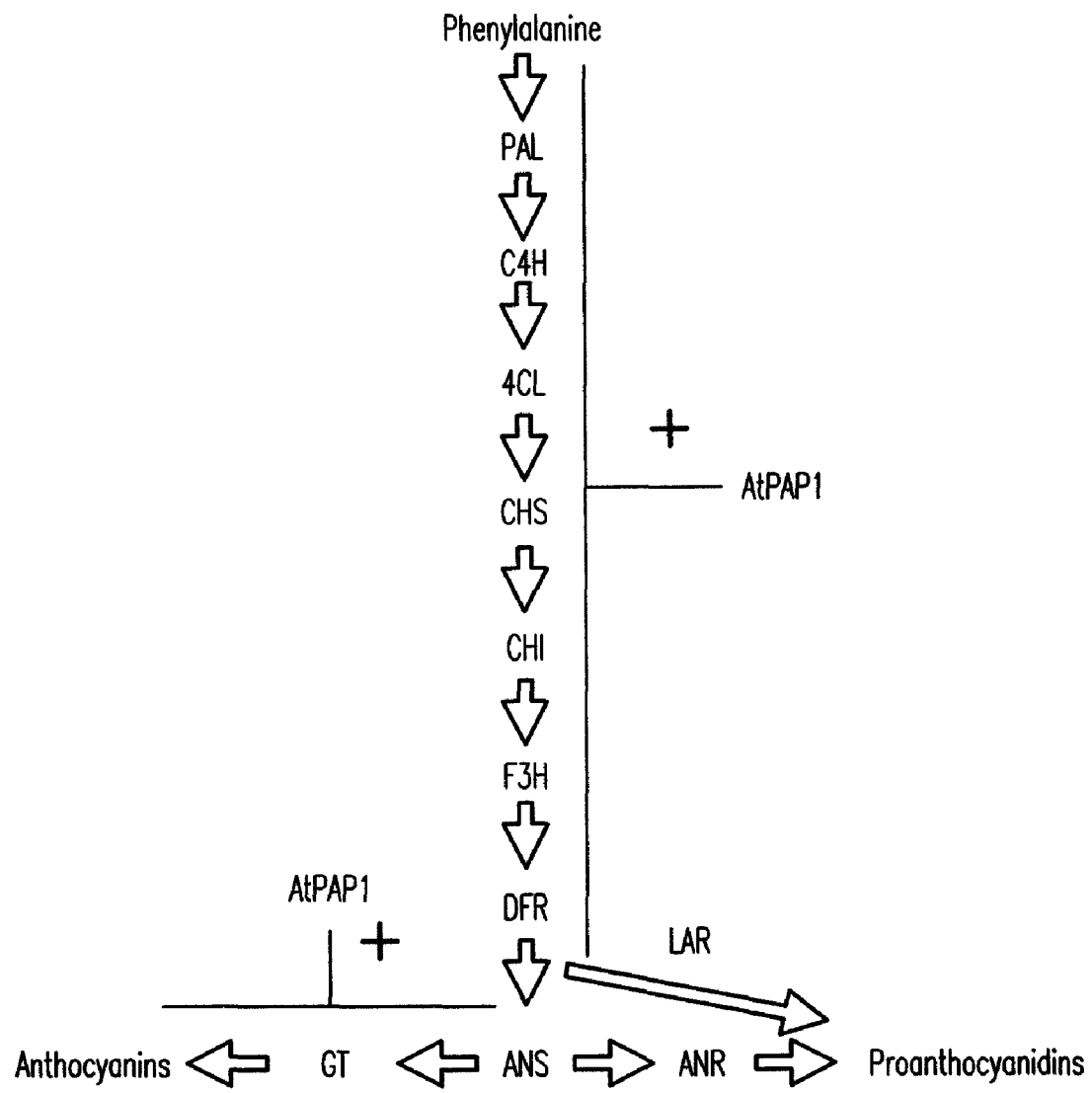
FIG. 1: Biosynthetic pathways leading to the synthesis of anthocyanins and proanthocyanidins. PAL, L-phenylalanine ammonia-lyase (E.C 4.3.1.5); C4H, cinnamate-4-hydroxylase (E.C 1.14.13.11); 4CL, 4-coumarate: CoA ligase (E.C.

In addition to providing the LAP1-LAP4 genes, other genes may be used in conjunction with any of LAP1-LAP4 to enhance the accumulation of proanthocyanidins, for instance by providing a gene encoding ANR, or other enzyme in the anthocyanidin or PA synthesis pathways. An ANR gene may be isolated by PCR, for instance by utilizing a nucleotide primer such as a BAN primer (e.g. SEQ ID NO:13) or other BAN primer for instance as found in U.S. Patent Publn. 2004/0093632. Thus, an ANR (BAN) homolog, for instance from *Medicago truncatula* (e.g. SEQ ID NO:43) may be utilized. Other anthocyanin synthetic enzyme activities as shown in FIGS. 1-2 may also be utilized in conjunction with the LAP genes, such as dihydroflavonol reductase (DFR) coding sequences (SEQ ID NOs:11-12). The genes may thus find use as part of a combination of genes to introduce or increase condensed tannin biosynthesis in numerous species, for forage improvement and nutritional improvement of foods. PA expression could also be modulated using a transgenic chalcone isomerase coding sequence (e.g. McKhann and Hirsch, 1994; Liu et al., 2002; (e.g. SEQ ID NOs:14-17)).

The invention also relates to feed products containing one or more of the sequences of the present invention. Such products produced from a recombinant plant or seed containing one or more of the nucleotide sequences of the present invention are specifically contemplated as embodiments of the present invention. A feed product containing one or more of the sequences of the present invention is intended to include, but not be limited to, feed, harvested hay, silage, crushed or whole grains or seeds of a recombinant plant or seed containing one or more of the sequences of the present invention.

Over-expression of *Medicago* chalcone isomerase may increase flavonoid biosynthesis in *Arabidopsis* (e.g. Liu et al., 2002). This could thus be used in combination with any of LAP1-LAP4 and/or ANR (BAN) to produce more PA. An *Arabidopsis* or other PAP-1 gene could also be used to increase flux into the pathway (Borevitz, 2000; e.g. SEQ ID NO:18). LAP1-LAP4 could also be used in conjunction with any one or more other regulatory genes such as TTG1 (GenBank Accession No. AJ133743; SEQ ID NO: 21, SEQ ID NO:22), TT1 (GenBank Accession No. AF190298; SEQ ID NO:23, SEQ ID NO:24), and TT8 (GenBank Accession No. AJ277509; SEQ ID NO: 25, SEQ ID NO:26). Benefit may also be obtained from use of any of LAP1-LAP4 in conjunction with TT12 (GenBank Accession No. AJ294464; SEQ ID NO:19, SEQ ID NO:20) for transport of PA to the vacuole. Any combination of the foregoing sequences may therefore be used with the invention.

A LAP sequence may be used in conjunction with another sequence encoding an ANR (BAN) homolog, for example, from barley (SEQ ID NO:27, SEQ ID NO:29, SEQ ID NO:31 and SEQ ID NO:33), Brassica napus (SEQ ID NO:35), cotton (SEQ ID NO:37) and grape (SEQ ID NO:39). The corresponding encoded polypeptides are given in SEQ ID NO:28, SEQ ID NO: SEQ ID NO:30, SEQ ID NO:32, SEQ ID NO:34, SEQ ID NO:36, SEQ ID NO:38, SEQ ID NO:40. Other ANR sequences which may be utilized include those from M. truncatula (e.g. SEQ ID NO:43) or A. thaliana (e.g. SEQ ID NO:45). The corresponding encoded peptides are given in SEQ ID NO:44 and SEQ ID NO:46. One aspect of the invention thus provides a LAP-encoding sequence, such as LAP1-LAP4 (SEQ ID NOs:1-4), used in conjunction with another PA biosynthesis sequence. Also provided are nucleic acids hybridizing to any of the foregoing nucleic acid sequences and encoding a polypeptide conferring a LAP phenotype.

As indicated above, a modulation of the phenotype of a gene may be obtained in accordance with the invention by introduction of recombinant nucleic acids comprising a LAP coding sequence. Other aspects of the invention are sequences that hybridize to the LAP1-LAP4 coding sequences provided herein under high stringency conditions. As used herein, "hybridization" or "hybridizes" is understood to mean the forming of a double or triple stranded molecule or a molecule with partial double or triple stranded nature. As used herein "stringent condition(s)" or "high stringency" are those conditions that allow hybridization between or within one or more nucleic acid strand(s) containing complementary sequence(s), but precludes hybridization of random sequences.

Stringent conditions tolerate little mismatch between a nucleic acid and a target strand. Such conditions are well known to those of ordinary skill in the art, and are preferred for applications requiring high selectivity. Medium stringent conditions may comprise relatively low salt and/or relatively high temperature conditions, such as provided by about 1×SSC, and 65° C. High stringency may be defined as 0.02M to 0.10M NaCl and 50° C. to 70° C. Specific examples of such conditions include 0.02M NaCl and 50° C.; 0.02M NaCl and 60° C.; and 0.02M NaCl and 70° C.

Alterations of the native amino acid sequence to produce variant polypeptides can be prepared by a variety of means known to those ordinarily skilled in the art. For instance, amino acid substitutions can be conveniently introduced into the polypeptides by changing the sequence of the nucleic acid molecule at the time of synthesis. Site-specific mutations can also be introduced by ligating into an expression vector a synthesized oligonucleotide comprising the modified sequence. Alternately, oligonucleotide-directed, site-specific mutagenesis procedures can be used, such as disclosed in Walder et al. (1986); and U.S. Pat. Nos. 4,518,584 and 4,737,462.

In making such changes, the hydropathic index of amino acids may be considered. The importance of the hydropathic amino acid index in conferring interactive biological function on a protein is generally understood in the art (e.g. Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid may be assigned a hydropathic index on the basis of their hydrophobicity and charge characteristics. These are, for instance: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate/glutamine/aspartate/asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biologically functional protein. In making such changes, the substitution of amino acids whose hydropathic indices are within .+−.2 is preferred, those within .+−.1 are more preferred, and those within .+−.0.5 are most preferred.

It is also understood in the art that the substitution of like amino acids may be made effectively on the basis of hydrophilicity. U.S. Pat. No. 4,554,101 states that the greatest local average hydrophilicity of a protein, as governed by the hydrophilicity of its adjacent amino acids, correlates with a biological property of the protein. The following hydrophilicity values have been assigned to amino acids: arginine/lysine (+3.0); aspartate/glutamate (+3.0.+−.1); serine (+0.3); asparagine/glutamine (+0.2); glycine (0); threonine (−0.4); proline (−0.5.+−.1); alanine/histidine (−0.5); cysteine (−1.0); methionine (−1.3); valine (−1.5); leucine/isoleucine (−1.8); tyrosine (−2.3); phenylalanine (−2.5); and tryptophan (−3.4).

It is understood that an amino acid may be substituted by another amino acid having a similar hydrophilicity score and still result in a protein with similar biological activity, i.e., still obtain a biologically functional protein. In making such changes, the substitution of amino acids whose hydropathic indices are within .+−.2 is preferred, those within .+−.1 are more preferred, and those within .+−.0.5 are most preferred.

As outlined above, amino acid substitutions are therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine, and isoleucine.

It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture. It is also understood that compositions and conditions for hybridization are mentioned by way of non-limiting examples only, and that the desired stringency for a particular hybridization reaction in a plant cell is often determined empirically by comparison to one or more positive or negative controls. Depending on the application envisioned it is preferred to employ varying conditions of hybridization to achieve varying degrees of selectivity of a nucleic acid towards a target sequence. Thus, nucleotide sequences displaying 95%, 98%, 99%, or greater similarity over the length of their coding regions to the LAP1-LAP4 coding sequences (SEQ ID NOs:1-4) provided herein, and that encode a functional LAP protein, are also an aspect of the invention, as is a LAP protein encoded by such a gene.

II. Plant Transformation Constructs

Certain embodiments of the current invention concern plant transformation constructs. For example, one aspect of the current invention is a plant transformation vector comprising a LAP1, LAP2, LAP3, or LAP4 coding sequence alone, or in combination with one or more PA biosynthesis gene(s). Examples of PA biosynthesis genes include BAN (i.e. ANR), PAP-1, TTG1 TTG2, TT1, and/or TT8. Exemplary PA biosynthesis coding sequences for use with the invention also include the *Arabidopsis* TT2 coding sequence (SEQ ID NO:41), which encodes the polypeptide sequence of SEQ ID NO:42, as well as a *Medicago truncatula* or *A. thaliana* BAN DNA sequence or encoded BAN polypeptide (e.g. SEQ ID NOs:43-46). Such LAP coding sequences may encode a polypeptide of any of SEQ ID NOs:5-8, for instance comprising the nucleotide sequence of any of SEQ ID NOs: 1-4. Such coding sequences may be present in one or more plant expression cassettes and/or transformation vectors for introduction to a plant cell.

In certain embodiments of the invention, coding sequences are provided operably linked to a heterologous promoter, in either sense or antisense orientation. Expression constructs are also provided comprising these sequences, as are plants and plant cells transformed with the sequences.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with sense or antisense PA biosynthesis genes. The PA biosynthesis gene may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with the PA biosynthesis coding sequences will often depend on the purpose of the transformation. One of the major purposes of transformation of crop plants is to add commercially desirable, agronomically important traits to the plant. As PAs are known to confer many beneficial effects on health, one such trait is increased biosynthesis of tannins. Alternatively, plants may be engineered to decrease synthesis of PA and increase anthocyanin content, for instance to promote production of a food colorant. Identification and engineered expression of LAP coding sequences as well as sequences from additional anthocyanin and PA biosynthesis-related functions allows for rational manipulation of the biosynthetic flux through these pathways.

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. However, this may not always be the case, and the present invention also encompasses transgenic plants incorporating non-expressed transgenes. Preferred components likely to be included with vectors used in the current invention are as follows.

A. Regulatory Elements

Exemplary promoters for expression of a nucleic acid sequence include plant promoter such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those associated with the R gene complex (Chandler et al., 1989). Tissue specific promoters such as root cell promoters (Conkling et al., 1990) and tissue specific enhancers (Fromm et al., 1986) are also contemplated to be particularly useful, as are inducible promoters such as ABA- and turgor-inducible promoters. In certain embodiments of the invention, the native promoter of a PA biosynthesis gene may be used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is specifically envisioned that PA biosynthesis coding sequences may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, and an α-tubulin gene that also directs expression in roots.

B. Terminators

Transformation constructs prepared in accordance with the invention will typically include a 3' end DNA sequence that acts as a signal to terminate transcription and allow for the poly-adenylation of the mRNA produced by coding sequences operably linked to a PA biosynthesis gene. In one embodiment of the invention, the native terminator of a PA biosynthesis gene is used. Alternatively, a heterologous 3' end may enhance the expression of sense or antisense PA biosynthesis genes. Terminators which are deemed to be particularly useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms "selectable" or "screenable markers" also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

III. Antisense and RNAi Constructs

Antisense treatments represent one way of altering PA biosynthesis in accordance with the invention. In this manner, the accumulation of PA precursors, including anthocyanidins, could also be achieved. As such, antisense technology may be used to "knock-out" the function of an anthocyanin biosynthesis gene or homologous sequences thereof, such as UGT78G1, to increase the pool of anthocyanidin available for PA formation.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see above) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

RNA interference (RNAi) is a process utilizing endogenous cellular pathways whereby a double stranded RNA (dsRNA) specific target gene results in the degradation of the mRNA of interest. In recent years, RNAi has been used to perform gene "knockdown" in a number of species and experimental systems, from the nematode *C. elegans*, to plants, to insect embryos and cells in tissue culture (Fire et al., 1998; Martinez et al., 2002; McManus and Sharp, 2002). RNAi works through an endogenous pathway including the Dicer protein complex that generates 21-nucleotide small interfering RNAs (siRNAs) from the original dsRNA and the RNA-induced silencing complex (RISC) that uses siRNA guides to recognize and degrade the corresponding mRNAs. Only transcripts complementary to the siRNA are cleaved and degraded, and thus the knock-down of mRNA expression is usually sequence specific. One of skill in the art would routinely be able to identify portions of, for instance, the UGT78G1 sequence, as targets for RNAi-mediated gene suppression to increase proanthocyanidin levels in alfalfa.

IV. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bacto™ agar (Difco-BD, Franklin Lakes, N.J.), Hazelton agar (Hazleton, Lenexa, Kans., USA), Gelrite® (Sigma, St. Louis, Mo.), PHYTAGEL (Sigma-Aldrich, St. Louis, Mo.), and GELGRO (ICN-MP Biochemicals, Irvine, Calif., USA) are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, callus, immature embryos and gametic cells such as microspores, pollen, sperm and egg cells. Callus may be initiated from tissue sources including, but not limited to, immature embryos, seedling apical meristems, root, leaf, microspores and the like. Those cells which are capable of proliferating as callus also are candidate recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population, for example by manual selection and culture of friable, embryogenic tissue. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al., (1975) and MS media (Murashige and Skoog, 1962).

V. Methods for Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616), wheat (McCormac et al., 1998), barley (Tingay et al., 1997; McCormac et al., 1998), alfalfa (e.g. Thomas et al., 1990; McKersie et al., 1993) and maize (Ishida et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics® Particle Delivery System (Dupont), which can be used to propel particles coated with DNA or cells through a screen, such as a stainless steel or nylon screen (e.g. NYTEX screen; Sefar America, Depew, N.Y. USA), onto a filter surface covered with plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994), wheat (U.S. Pat. No. 5,563,055), and sorghum (Casa et al., 1993); as well as a number of dicots including tobacco (Tomes et al., 1990; Buising and Benbow, 1994), soybean (U.S. Pat. No. 5,322,783), sunflower (Knittel et al., 1994), peanut (Singsit et al., 1997), cotton (McCabe and Martinell, 1993), tomato (VanEck et al., 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of plants from protoplasts have been described (Toriyama et al., 1986; Yamada et al., 1986; Abdullah et al., 1986; Omirulleh et al., 1993 and U.S. Pat. No. 5,508,184). Examples of the use of direct uptake transformation of protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128; (Thompson, 1995) and rice (Nagatani, 1997).

VI. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one experiment. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al., 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

It further is contemplated that the herbicide DALAPON, 2,2-dichloropropionic acid, may be useful for identification of transformed cells. The enzyme 2,2-dichloropropionic acid dehalogenase (deh) inactivates the herbicidal activity of 2,2-dichloropropionic acid and therefore confers herbicidal resistance on cells or plants expressing a gene encoding the dehalogenase enzyme (Buchanan-Wollaston et al., 1992; U.S. Pat. No. 5,508,468).

Alternatively, a gene encoding anthranilate synthase, which confers resistance to certain amino acid analogs, e.g., 5-methyltryptophan or 6-methyl anthranilate, may be useful as a selectable marker gene. The use of an anthranilate synthase gene as a selectable marker was described in U.S. Pat. No. 5,508,468.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soiless plant growth mix, and hardened, e.g., in an environmentally controlled chamber, for example, at about 85% relative humidity, 600 ppm $CO_2$, and 25-250 microeinsteins $m^{-2}s^{-1}$ of light. Plants are preferably matured either in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plantcon™ containers (MP-ICN Biomedicals, Solon, Ohio, USA). Regenerating plants are preferably grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$ M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and northern blotting and PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR analysis. In addition, it is not typically possible using PCR™ techniques to determine whether transformants have exogenous genes introduced into different sites in the genome, i.e., whether transformants are of independent origin. It is contemplated that using PCR techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR, e.g., the presence of a gene, but also demonstrates integration into the genome and characterizes each individual transformant.

Whereas DNA analysis techniques may be conducted using DNA isolated from any part of a plant, RNA will only be expressed in particular cells or tissue types and hence it will be necessary to prepare RNA for analysis from these tissues. PCR techniques also may be used for detection and quantitation of RNA produced from introduced genes. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

E. Gene Expression

While Southern blotting and PCR may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

VII. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected CT biosynthesis gene can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VIII. Definitions

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Proanthocyanidin (PA) biosynthesis gene: A gene encoding a polypeptide that catalyzes one or more steps in the biosynthesis of condensed tannins (proanthocyanidins).

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule capable of replication in a host cell and/or to which another DNA segment can be operatively linked so as to bring about replication of the attached segment. A plasmid is an exemplary vector.

IX. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

The *Arabidopsis* PAP1 Myb Transcription Factor Does Not Induce Anthocyanin Production in Legumes The PAP1 (producer of anthocyanin pigmentation) gene of *Arabidopsis* encodes a MYB transcription factor (Borevitz et al., 2000). The PAP1 gene of *Arabidopsis* is a global regulator of the anthocyanin biosynthetic pathway, and its ectopic expression in *Arabidopsis* results in a deep purple phenotype associated with accumulation of anthocyanins (Borevitz et al., 2000; Tohge et al., 2005). A similar phenotype is observed when AtPAP1 is expressed in tobacco (Borevitz et al., 2000; Xie et al., 2006), suggesting that AtPAP1 function might not be species-specific. During attempts to introduce anthocyanin as substrate for conversion into PAs in forage legumes, a 35S-AtPAP1 construct was introduced by *Agrobacterium*-mediated transformation into alfalfa, *Medicago truncatula* and white clover. Multiple independent transgenic lines were verified as expressing the PAP1 transgene, but the plants never demonstrated a purple phenotype (e.g. FIG. 3A), and foliar anthocyanins could not be detected by HPLC analysis. Thus, over-expression of PAP1 leads to strong constitutive induction of the complete pathway leading to anthocyanins in *Arabidopsis* and tobacco, but not in leguminous plants.

Example 2

Identification of *Medicago* Anthocyanin Pathway Regulatory Genes

To overcome the above limitation in expressing PA's and/or anthocyanins in legumes including alfalfa, a bioinformatics search was undertaken to identify transcription factors from *M. truncatula* (a close relative of alfalfa) which might regulate anthocyanin synthesis in legumes in a similar manner to the effects of expression of AtPAP1 in *Arabidopsis* and tobacco. Since transcription factors are expressed at very low levels they are rarely found in traditional EST collections. Indeed, the *Arabidopsis* PAP1 and PAP2 genes were first identified using an activation tagging screen (Borevitz et al., 2000). Searches of the publicly available *M. truncatula* EST collections (e.g. *Medicago truncatula* Gene Index at Dana Farber Cancer Institute (www.compbio.dfci.harvard.edu/tgi/cgi-bin/tgi/gimain.pl?gudb=medicago) led to no *Medicago* sequences apparently homologous to *Arabidopsis* PAP1 or PAP2. The approach subsequently taken was therefore to identify similar genes from other plant species and use them as templates for further BLAST analysis.

There are several PAP1-like MYB genes in various species including tomato, grape, strawberry and petunia, all of which have been shown to regulate anthocyanin synthesis in the respective species (Quattrocchio et al., 1999; Aharoni et al., 2001; Mathews et al., 2003; Deluc et al., 2006). However, although all these transcription factors share the conserved R2-R3 MYB domain, the C-terminal regions of the open reading frames appears to exhibit marginal cross-species similarity, and it is not possible to ascribe a function based on overall sequence similarity. Using the AtPAP1 sequence, BLAST analysis (e.g. NCBI BLAST found at www.ncbi.nlm.nih.gov/BLAST) was performed against the currently known genomic sequence of *M. truncatula*, and several MYB-like sequences were identified. To better identify true anthocyanin-regulatory genes, two functional orthologs of PAP1, AN2 from Petunia and Anthocyanin 1 from tomato (SEQ ID NOs:95-96), were then compared with the *Medicago* MYB genes. Four *Medicago* genomic sequences with moderate similarity to both AN2 and AtPAP1 were identified and named MtLAP1-MtLAP4 (for Legume Anthocyanin Producer: gi|84662902|gb|AC152405.15|, 100321-101295 bases (SEQ ID NO:89); gi|86604519|emb|CT573509.1|, 52130-53141 bases (SEQ ID NO:90); gi|86361369|gb|AC172742.2|, 29610-32813 bases (SEQ ID NO:91; and gi|86604519|emb|CT573509.1|, 13597-15603 bases (SEQ ID NO:92). These genes were not represented by ESTs in GenBank or the TIGR *M. truncatula* database, indicating that the encoded transcription factors are either expressed at very low levels, or have temporally and or/spatially limited expression patterns.

Figure 4A:
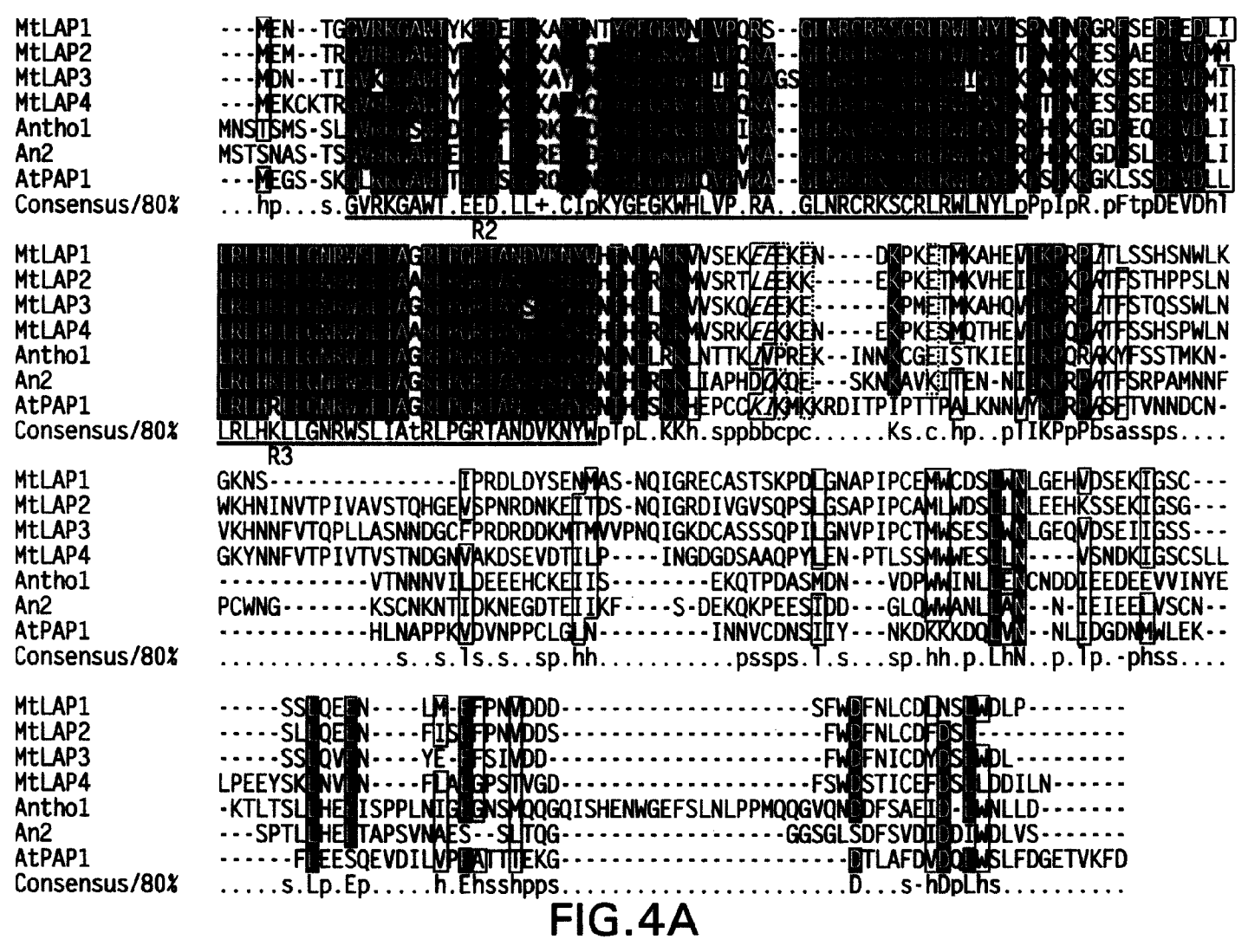
Figure 4B:
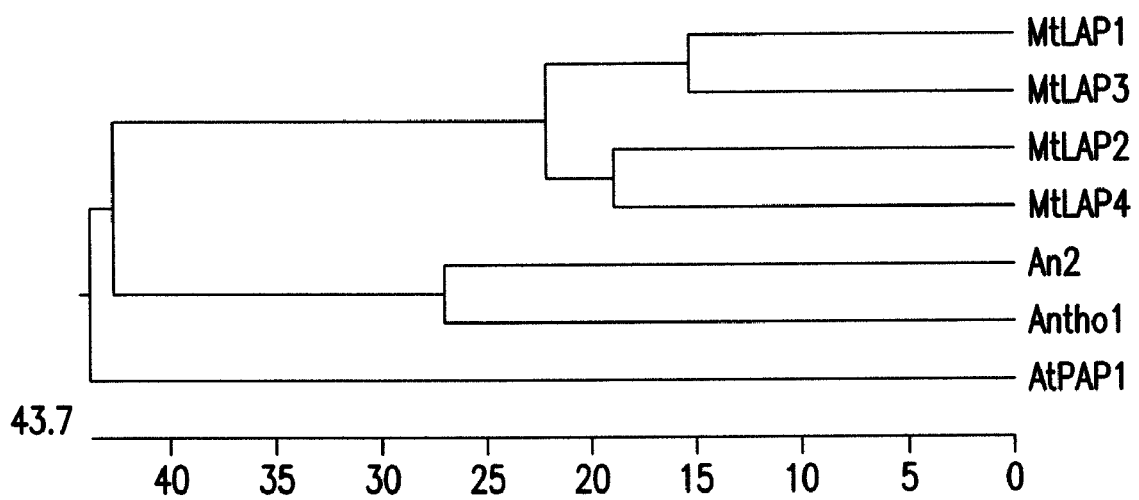

FIG. 4A shows the predicted open reading frames of *Medicago* LAP1-LAP4 aligned with the *Arabidopsis*, tomato and petunia anthocyanin regulatory transcription factors. All of these proteins share the conserved R2R3MYB-like domain; however, past this region there is very little similarity. FIG. 4B shows the phylogenetic relationships between the predicted ORFs. MtLAP1 and MtLAP3 were the most similar pair, with close to 73% identity. The other MtLAP members have between 59.5 and 69% identity to one another, whereas AtPAP1 and AN2 proteins are between 36 and 47% identical, with MtLAP1 sharing only 41% amino acid identity to AtPAP1. This lack of similarity probably explains the lack of an anthocyanin phenotype in alfalfa plants expressing AtPAP1.

Primers were designed to amplify the three exons of MtLAP1 and MtLAP2 separately (Table 1; SEQ ID NOs:47-52), and the PCR products were then combined to amplify the corresponding complete open reading frame which was cloned directionally into the pENTR-D vector (Invitrogen, Carlsbad, Calif.) and transformed into *E. coli* DH5α. After sequencing to confirm that no errors had been introduced, the ORFs were transferred into the binary expression vector pB2GW7. The plasmids (pB2-MtLAP1, pB2-MtLAP2, and pB2-GUS as control) were then re-sequenced to confirm proper orientation and transformed into *Agrobacterium tumefaciens* strain AGL1 (Lazo et al., 1991).

TABLE 1

Primers used to amplify the MtLAP1 ORF from genomic sequences (SEQ ID NOs: 47-52).

| Primer Name | Sequence(5'-3') |
|---|---|
| 5'MtLAP1Gen-1 | CACCATGGAGAATACCGGAGGTGTGAGAAAA |
| 3'MtLAP1Gen-1 | TATTCAATCCAGATCTCTGAGGAACTAAATT |
| 5'MtLAP1Gen-2 | AGAGATCTGGATTGAATAGATGCAGAAAAAG |
| 3'MtLAP1Gen-2 | AATGACCATCTATTTCCTAGTAGTTTGTGTA |
| 5'MtLAP1Gen-3 | AGGAAATAGATGGTCATTGATTGCTGGAAGG |
| 3'MtLAP1Gen-3 | TCAAGGTAGATCCCAAAGAGAATTCAAATCACAA |

Example 3

Plant Transformation and Visible Phenotypes Arising from LAP1 Expression in Transgenic Plants Constructs harboring MtLAP1, MtLAP2 or GUS (for controls) were transformed into *Medicago truncatula* R108, *Nicotiana tabacum* and white clover (*Trifolium pratense*) using published protocols (Horsch et al., 1985; Thomas et al., 1990; Wright et al., 2006). Transgene DNA was isolated using the Dellaporta method (Dellaporta et al., 1983) and analyzed by qualitative PCR using 35S promoter- and transgene-specific primers. Plants were maintained in the greenhouse and allowed to self pollinate. In the case of the *Medicago truncatula* transformation, a total of 34 independent lines (each derived from a single embryo transformant) were obtained for the MtLAP1 and GUS transgenes, and 15 independent lines for the MtLAP2 transgene. MtLAP1 transformed into clover yielded 20 lines, while transformation of MtLAP1 into MtANR-expressing alfalfa (see below) yielded 20 independent lines (each line derived from a separate callus).

The open reading frame of MtANR was sub-cloned into the binary vector pBI121 under control of the cauliflower mosaic virus 35S promoter with kanamycin as the plant selectable marker. Alfalfa plants of cultivar R2336 (Forage Genetics International, Nampa, Id.) were transformed following published protocols (Thomas et al., 1990) and selected for kanamycin resistance. From this population of primary transformants, a single line designated R15 was selected and used for further transformation with MtLAP1. Plants were transformed as above and plantlets screened for both kanamycin and phosphinothricin resistance.

Figure 3A:
Figure 3B:
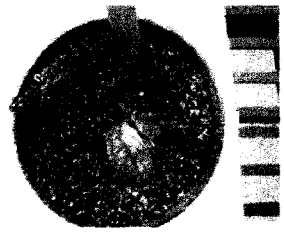
Figure 3C:
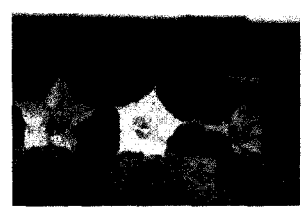

The open reading frame of MtLAP1 was obtained using primers designed to amplify the three exons of the gene separately (Table 1); the exons were then combined prior to cloning as described in Example 2. LAP1 was initially expressed in transgenic tobacco under control of the 35S-promoter. FIG. 3B shows the mottled anthocyanin phenotype of the leaves, and the clearly enhanced pink phenotype of the flowers is shown in FIG. 3C. Interestingly, the observed phenotype was not as strong or uniform as seen when AtPAP1 is similarly expressed in tobacco (Xie et al., 2006).

Figure 3D:
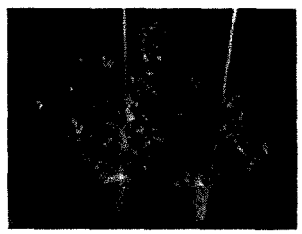
Figure 3E:
Figure 3F:
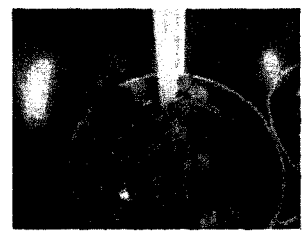
Figure 3G:
Figure 3H:
Figure 3I:
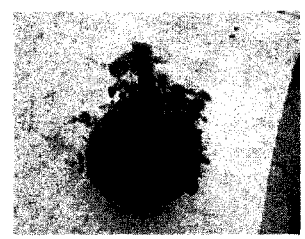

The 35S-MtLAP1 construct was then introduced into *M. truncatula* and alfalfa by *Agrobacterium*-mediated transformation. The alfalfa line used for transformation also contained a 35S-promoter driven copy of the *Medicago* ANR gene. An intense, uniform purple phenotype was observed in both species. FIG. 3D and FIG. 3E show the strong pigmentation in *M. truncatula* leaves, stems and seed pods. The roots also appeared to be strongly pigmented (data not shown). Alfalfa plants co-expressing LAP1 and ANR exhibited a strong but more diffuse purple phenotype than the *M. truncatula* lines expressing LAP1 alone (FIG. 3F). Similarly, a significant proportion of the purple pigmentation resulting from AtPAP1 expression is lost in tobacco plants co-expressing AtPAP1 and ANR (Xie et al., 2006). Expression of MtLAP2 also resulted in purple pigmentation of alfalfa foliage (FIG. 5), indicating increased anthocyanin production as well. Transformation of white clover (*Trifolium pratense*) with 35S-LAP1 resulted in strong anthocyanin pigmentation throughout the leaf, except for the central region around the major leaf vein (FIG. 3H), as compared to the untransformed control plant (FIG. 3I).

Example 4

Anthocyanin and Proanthocyanidin Content and Composition in *Medicago* Leaf Tissue Expressing LAP1

A. Anthocyanins

Total flavanoids were extracted from 100-500 mg samples (i.e. samples of Example 5) using 10 volumes of methanol: HCl (99:1 v/v). The first extraction was overnight at 4° C. and the $2^{nd}$ and $3^{rd}$ extractions were for 2 h each. The supernatants were combined and dried under a stream of nitrogen or in a Speed Vac (Thermo-Savant, Waltham, Mass.). The dried samples were resuspended in 1 ml of methanol mixed with 500 µl of chloroform and 600 µl $ddH_2O$. Following centrifugation at 12,000 g for 5 min, the aqueous supernatant was removed and dried. The dried samples were resuspended in methanol (1 mg/ml); one aliquot was re-dried in a speed vac, and the absorbance of another aliquot was measured at 535 nm (diluting samples where necessary) for total anthocyanin content using cyanidin as a reference standard. The samples were then resuspended in 2N HCl and heated at 90° C. for 2 h to hydrolyze glycosidic bonds. Following cooling to room temperature the aglycones were extracted with ethyl acetate (3×250 µl), dried under nitrogen, and then resuspended in methanol. Samples were analyzed on an HP 1100 series HPLC (Agilent Technologies, Palo Alto, Calif.) on a 250×4.6 mm C18 reversed phase column (Waters Sperisorb 5µ ODS2, Metachem Technologies Inc., Palo Alto, Calif.) with UV detection. The solvents used in the separation were 0.1% phosphoric acid (A) and acetonitrile (B). The gradient used for analysis was the same as reported previously (Xie et al., 2006). Individual compounds were identified by retention times and absorption spectra by comparison with authentic standards injected separately.

Mass spectra of anthocyanins were acquired using a Bruker Esquire LC equipped with an electrospray ionization source in the positive mode (Bruker Optics, Billerica, Mass.). Positive ion ESI was performed using a source voltage of 3000 and capillary offset voltage of −70.7 V. Nebulization was achieved using Nitrogen gas at a pressure of 70 psi. Desolvation was aided by using nitrogen at a pressure of 12 psi as counter current gas. The capillary temperature was set at 350° C. Mass spectra were recorded over the range of 50-2200 m/z. The Bruker ion trap was operated under an ion current control of 20,000 with a max acquire time of 100 ms and a trap drive setting of 50. Automated MS/MS was performed by isolating the parent ion between 100-1900 m/z using an isolation width of 2.0, a fragmentation amplitude of 0.9, and a threshold of 1,500 with a max acquire time of 100 ms.

B. Proanthocyanidins

PAs were extracted by the method of Gu (Gu et al., 2002) with the following modifications; frozen ground tissues (0.5 g) were extracted with 5 ml 70% acetone/0.5% acetic acid first by vortexing then by sonication at 30° C. for 30 min. Following centrifugation at 3,000 g, the supernatant was decanted into a 50 ml tube, while the residue was re-extracted again as above. The samples were then treated with 20 ml of chloroform to separate hydrophilic from hydrophobic compounds. Following centrifugation as above, the supernatant was retained and extracted a further two times with an equal volume of chloroform, then three times with hexanes (to remove residual fats). The samples were briefly dried under a stream of nitrogen, then freeze-dried for 48 h. The dried samples were resuspended in extraction (70% acetone/0.5% acetic acid) (3 mg/µl initial weight). Total PAs were measured using a modified microplate assay: Samples (2.5 µl) were mixed with 197.5 µl DMACA (dimethylaminocinnamaldehyde) reagent (0.2% w/v in methanol: 6N HCl (1/1)) in a well of a microplate. Samples were incubated for 5 min, then the absorbance at 630 nm was recorded on a Victor2 microplate reader (Victor2™ multilabel counter, Perkin Elmer) equipped with a 630 nm emission filter. Blanks consisted of samples mixed with methanol: 6N HCl (1/1). Amounts are reported as catechin equivalents.

The polymer size of the PAs was examined using a combination of HPLC methods. Samples (5-20 µl) were analyzed on a 250×4.6 mm Silica column (Luna 5µ Supleco, St. Louis, Mo.). The solvents and gradients were similar to those reported previously (Gu et al., 2002) with the following modifications: starting solvent composition was 82% methylene chloride (Solvent B), 14% methanol (Solvent C); 0-30 min 14-28.4% B; 30-45 min 28.4-39.6% B, 45-50 min 39.6-96% B; hold for 10 min then 60-65 min 96-14% B with 10 min re-equilibration. The individual components were detected by a modification of a post-column reaction system (Treutter, 1989; Treutter et al., 1994; Pascual-Teresa et al., 1998). The effluent from the column was combined with 1% DMACA in methanol (acidified with $H_2SO_4$, 1.5 N) via a mixing tee connected to an auxiliary pump (Alltech 460; Alltech Associates, Deerfield, Ill., USA). The sample passed through 8 m of 0.2 mm i.d. PEEK tubing before detection at 640 nm.

C. Summary

Figure 6A:
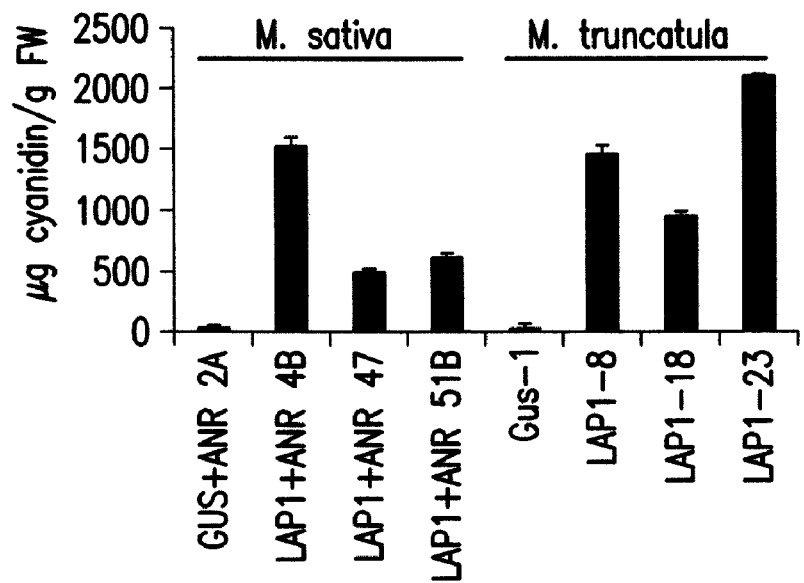
Figure 6B:
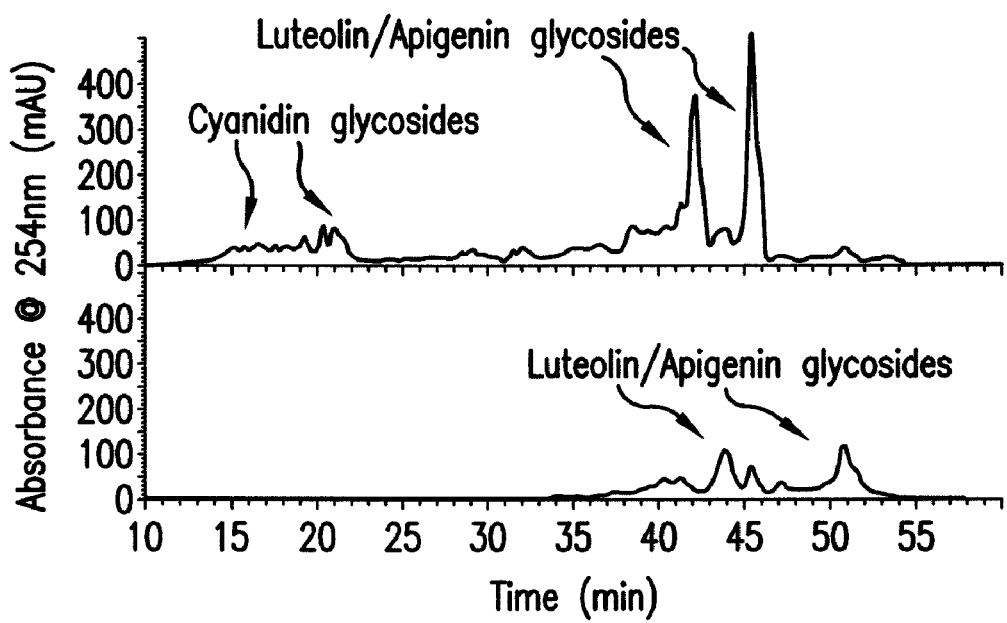
Figure 6C:
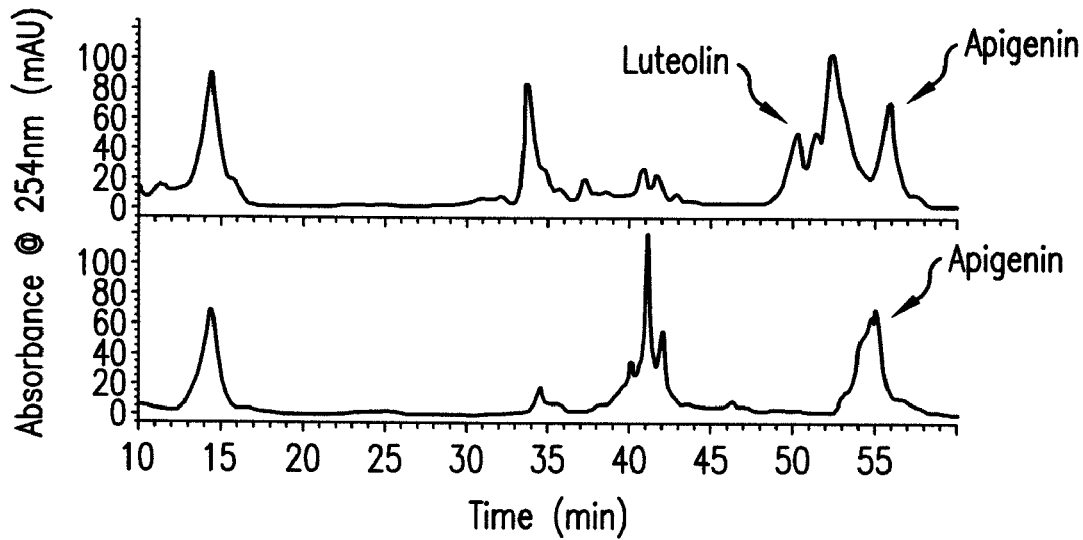
Figure 6D:
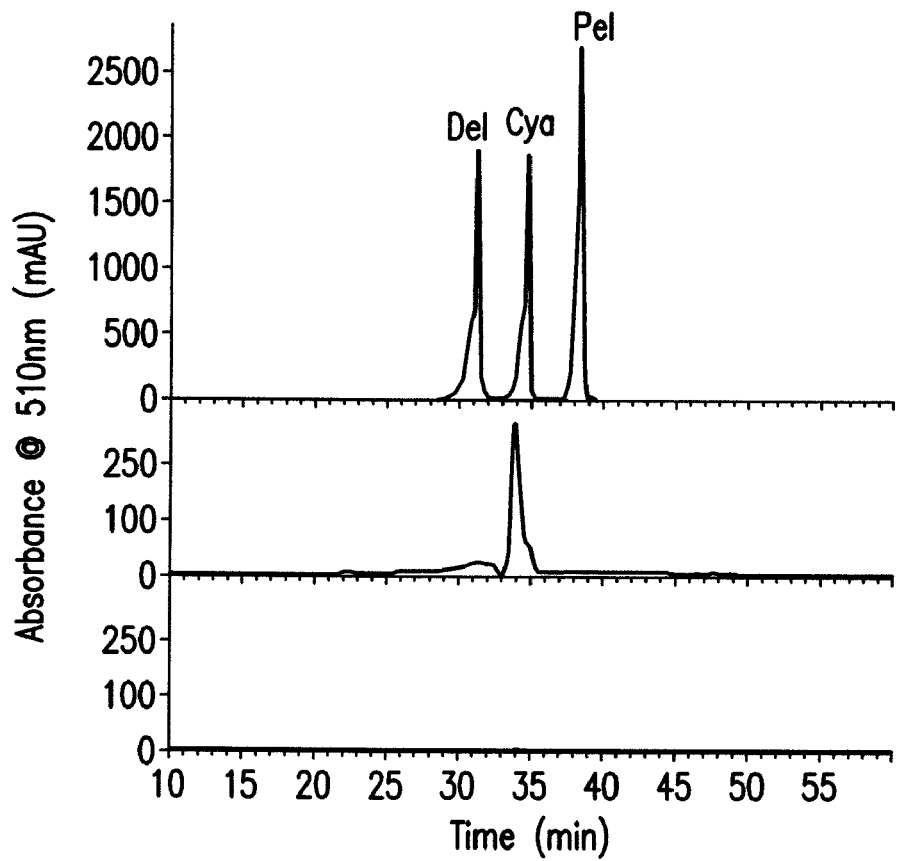

To qualitatively and quantitatively determine the metabolic effects of constitutive expression of LAP1 in *M. truncatula*, leaves were extracted in acidic methanol. *M. truncatula* leaves over-expressing MtLAP1 accumulate high levels of anthocyanins (1.0-2.3 mg/g FW, as determined by absorption spectroscopy) (FIG. 6A). When these leaf extracts were analyzed by reverse phase-HPLC, the presence of several cyanidin conjugates was observed as well as increased levels of flavone (luteolin, apigenin) glycosides in the MtLAP1-expressing lines (FIG. 6B). Following acid hydrolysis of the leaf extracts, the majority of the anthocyanidin released was cyanidin, indicating that MtLAP1 expression leads to the accumulation of predominately cyanidin conjugates (glycosides and/or other esters) (FIG. 6C). FIG. 6D shows the hydrolysed anthocyanin extract from MsLAP1:MtANR leaf extracts, showing cyanidin as the major anthocyanin backbone.

Figure 7A:
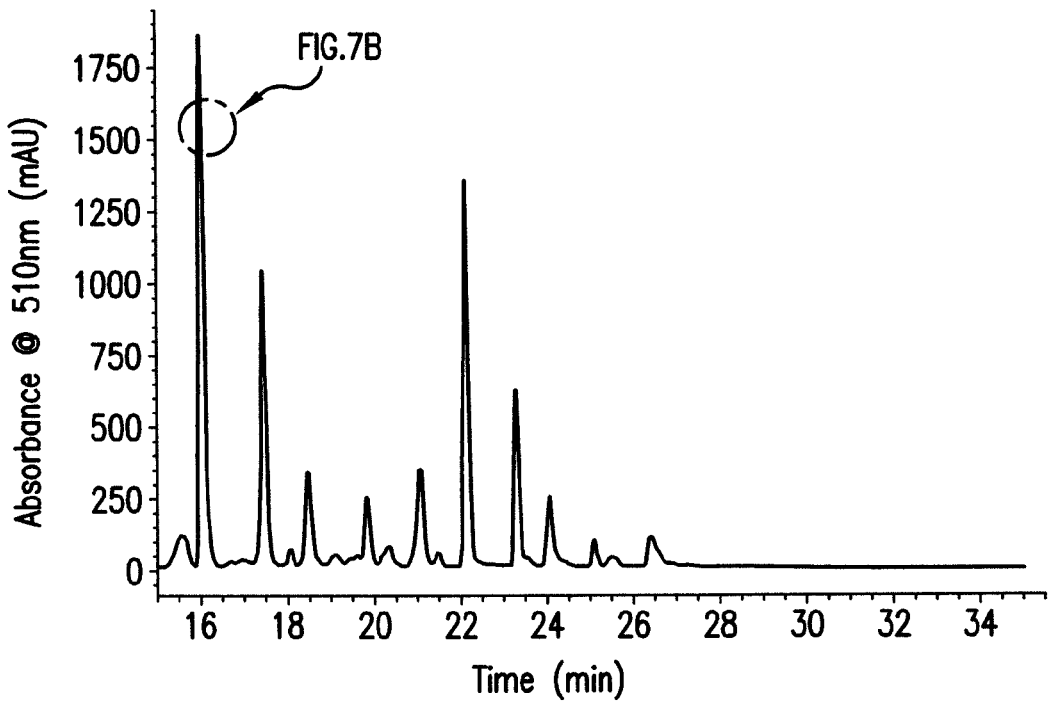
Figure 7B:
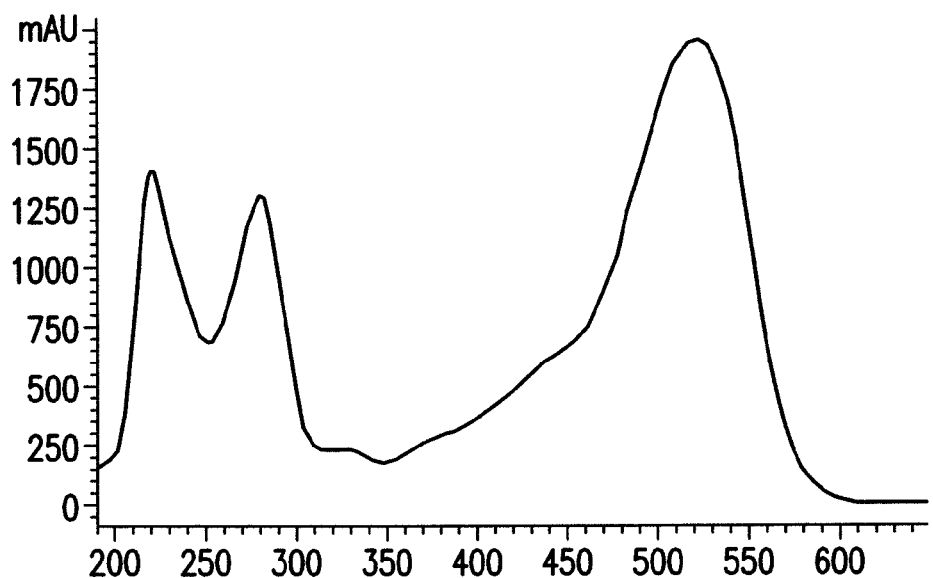
Figure 7C:
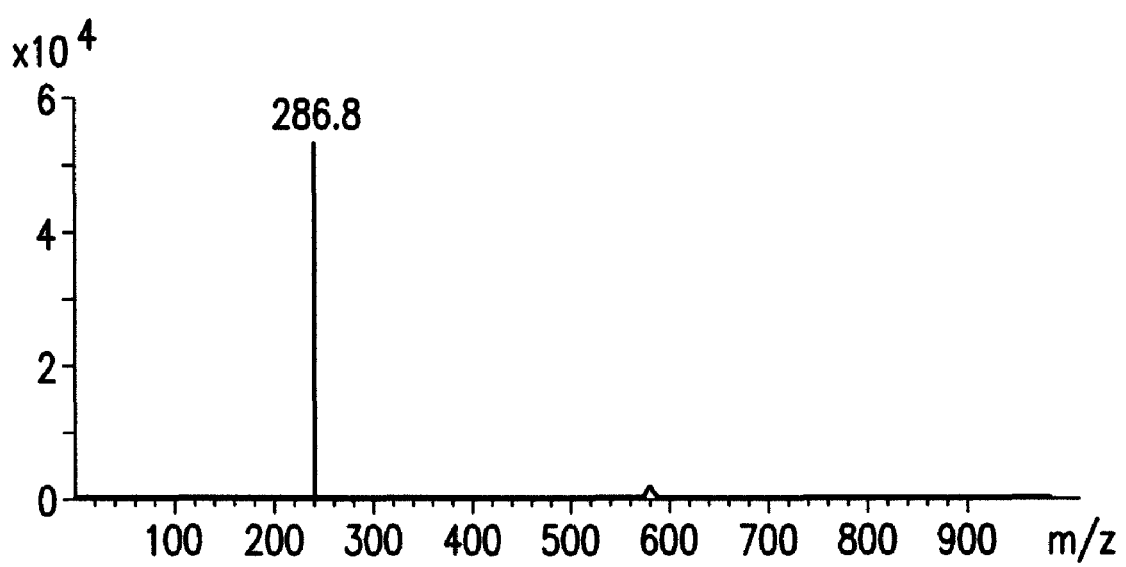
Figure 7D:
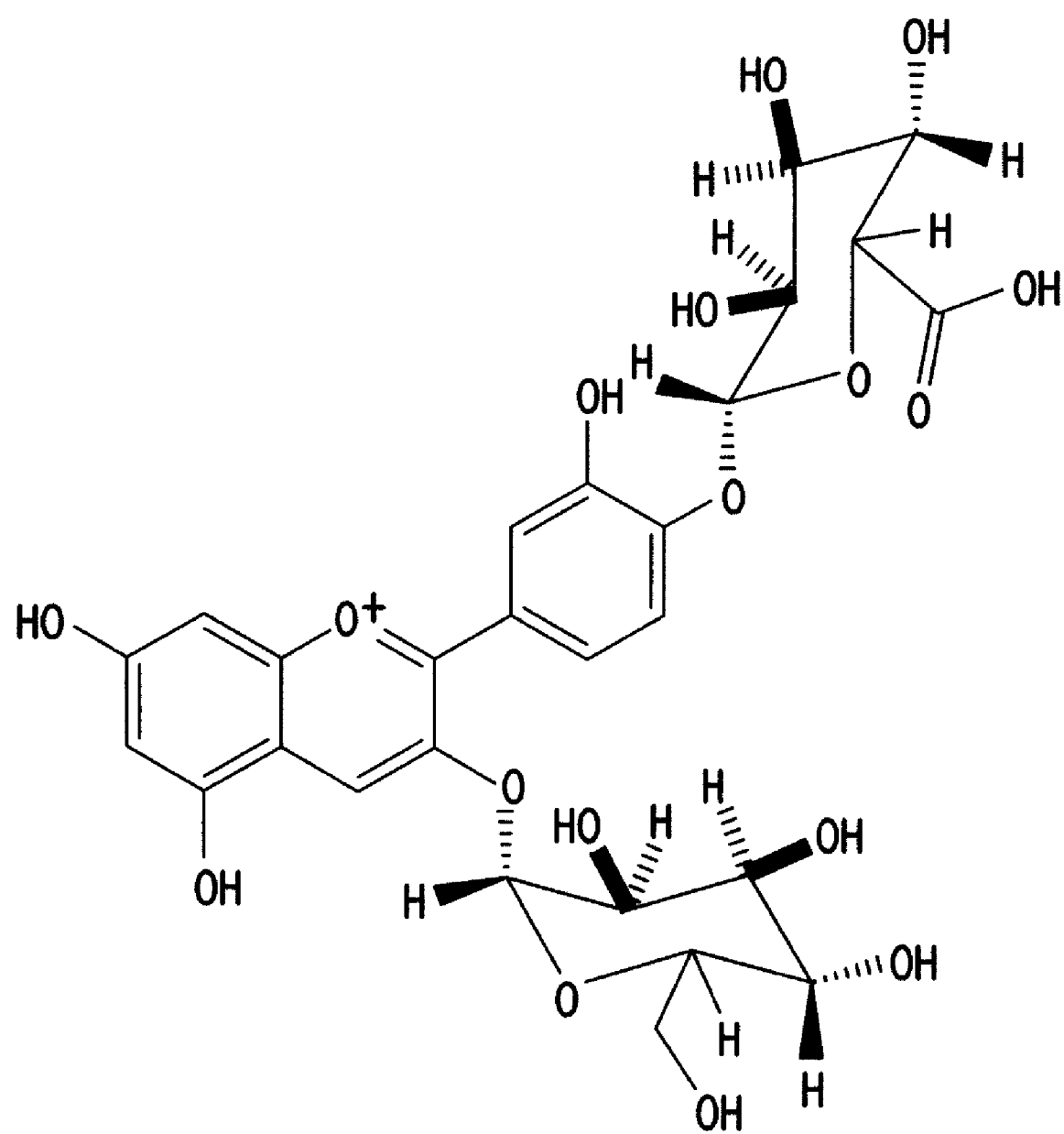

Methanolic extracts from leaves of alfalfa plants co-expressing LAP1 and ANR were subjected to LC MS/MS analysis to obtain further information as to the nature of the induced anthocyanins. FIG. 7A shows a typical chromatogram which reveals several cyanidin-containing peaks. All anthocyanins detected were derived from the cyanidin backbone, but differed in the type and degree of glycosylation. Eight major cyanidin derivatives were identified, most of which were multiply conjugated, with glucuronic acid conjugates predominating. UV and MS/MS analysis of the major compound eluting in the chromatograph shown in FIG. 7B revealed cyanidin conjugated with a glucuronic acid and a hexose (presumably glucose; tentative structure in FIG. 7D).

Example 5

Genes Regulated by LAP1 in *Medicago truncatula*

RNA was extracted from leaves of *M. truncatula* expressing LAP1, and alfalfa co-expressing LAP1 and MtANR, and subjected to RT-PCR analysis to monitor transcript levels for genes known to be involved in anthocyanin biosynthesis. The primers used are shown in Table 2.

TABLE 2

Primers used for RT-PCR analysis of anthocyanin and proanthocyanidin pathway gene expression. (SEQ ID NOs: 53-78)

| Primer Name | Sequence(5'-3') |
| --- | --- |
| 3'MtCHI | GTGTGCCACACAGTTCTCCA |
| 5'MtCHI | ATGGCTGCATCAATCACCGC |
| 3'MtF3'H | ATCTTCCTCCTATACATTTCAG |
| 5'MtF3'H | GGCACTATTACTCTATTGCT |
| 3'MtDFR-1 | CATCCCACAAGGGCTTTTGA |
| 5'MtDFR-1 | ATGGGTTCTATGGCCGAAACTG |
| 3'MtDFR-2 | CATCAATTACAGAATTTTGTTGCTCAG |
| 5'MtDFR-2 | ATGGGTTCAGTCTCAGAAACAG |
| 3'MtANS | TCCATAACCTTGAATCTTCC |
| 5'MtANS | CAAGTTCCAACAATAGACCT |
| 3'MtLAR | TGATAGATTTCATGGCTTCC |
| 5'MtLAR | TAACTGAGGCAAGTATTTCC |
| 3'MtActin | TAACCCTCATAGATTGGCAC |

TABLE 2-continued

Primers used for RT-PCR analysis of anthocyanin and proanthocyanidin pathway gene expression. (SEQ ID NOs: 53-78)

| Primer Name | Sequence(5'-3') |
| --- | --- |
| 5'MtActin | AGTAACTGGGATGACATGGA |
| 3'MtLAP1 | TGACAAAGTTATAGGACGAG |
| 5'MtLAP1 | AAGTTGTAGATTGAGGTGG |
| 5'MtBAN | TGCAAACAAAACATCTCACCTCATAG |
| 3'MtBAN | AATTTCCACGCAGCCTTTTCAG |
| 5'MtPAL | ACAGGGAGTCATTTGGATGAGGTG |
| 3'MtPAL | GGAACTCCTAATCAACATGTTGACG |
| 5'MtC4H | AGCTAGTGAACCACCAAGGCATCC |
| 3'MtC4H | ACTGTCCTCCTTTCTCAGAAGTGTC |
| 5'MtCHS | AGTCTCAATGGTAAGTCCTGGTCC |
| 3'MtCHS | GGACAAGCACTATTTGGAGATGGAG |
| 5'MtF3H | AGACCAAGTGGGTGGTCTTCAAGC |
| 3'MtF3H | ATCTCTGAGATACACGATCAAGGAC |

RNA was also analyzed from leaves of control plants transformed with the β-glucuronidase (GUS) gene. Several flavonoid pathway genes were induced more than 10-fold as a result of LAP1 expression. These included chalcone synthase (CHS), flavanone 3'-hydroxylase (F3H'), dihydroflavonol reductase 1 (DFR1), and anthocyanidin synthase (ANS) (FIG. 8). However, neither phenylalanine ammonia-lyase (PAL) nor cinnamate 4-hydroxylase (C4H), the first two enzymes of the phenylpropanoid pathway, were up-regulated, suggesting that MtLAP1 acts only on anthocyanin pathway-specific genes. In contrast, PAL and C4H are strongly up-regulated by AtPAP1 expression in *Arabidopsis* (Borevitz et al., 2000). However, transcripts encoding chalcone isomerase, the second enzyme in the flavonoid branch, were not up-regulated by LAP1, and DFR2 was strongly induced in alfalfa but not in *M. truncatula*. LAP1 did not induce the PA-pathway specific enzymes leucoanthocyanidin reductase (LAR) or ANR.

A more global assessment of transcript induction in response to LAP1 expression was obtained by Affymetrix microarray comparison (Affymetrix Corp., Santa Clara, Calif., USA) of transcripts from *M. truncatula* expressing MtLAP1 or GUS. Three independent MtLAP1 and GUS control lines were examined.

Plants used for the microarray experiment were grown and maintained in the greenhouse under standard conditions (16 hr light/8 hr dark, 24° C./18° C.). Leaves from MtLAP1- and MtGUS-expressing plants were harvested directly into liquid nitrogen; care was taken to select leaves that were the same age and developmental stage to minimize variations between samples and treatments. Total RNA was isolated using Tri-Reagent™ (Sigma-Aldrich) according to the manufacturer's directions. Total RNA was then further purified, and DNA removed using Qiagen's RNeaSy™ MinElute Cleanup Kit. Samples were diluted to 250 ng/ul. RNA from three independent lines from each transformation were subjected to microarray analysis using the Affymetrix *Medicago* Gene Chip® as described (Deavours et al., 2006; Modolo et al., 2007).

Table 3 provides a summary of the relative transcript levels and annotations of all the genes present on the chip that were induced 1.5-fold or more as a result of LAP1 expression. All the major anthocyanin biosynthetic genes were up-regulated, including 4-coumarate CoA ligase (4CL; 4.9-fold), CHS (multiple genes, 5-96-fold), F3'H (110-fold), DFR-1 (109-fold), DFR-2 (6.6-fold) and ANS (32-fold). Several uridine diphosphate glycosyltransferases (UGTs) were up-regulated by LAP1 expression. These included a gene with homology to *Arabidopsis* UGT75CI that has previously been ascribed a role in the glycosylation of anthocyanidins (Tohge et al., 2005). Another glucosyltransferase, represented by TC105632, was up-regulated almost 30-fold in MtLAP1 leaf tissues. This enzyme has recently been classified as UGT78G1 (SEQ ID NO:10), and shows activity with anthocyanidins (cyanidin, delphinidin, and pelargonidin) although isoflavones are preferred substrates in vitro (Modolo et al, 2007).

In addition to biosynthetic enzymes involved in flavonoid biosynthesis, the other groups of induced genes encoded transcription factors, transporters, and a number of proteins of unknown function (Table 3) Two of the MYB transcription factor probes may be hybridizing to the LAP1 transgene product. It remains to be determined whether the more highly induced transcription factors, transporters and unknown proteins are directly involved in anthocyanin production and accumulation.

TABLE 3

Genes induced by LAP1 expression.

| | Fold Increase | TC/Gene | Medicago annotation | Link to homolog/est | Description |
|---|---|---|---|---|---|
| 1 | 1.500459438 | TC108827 | | ABE94086 | VQ (Medicago truncatula). VQ motif; pfam05678 |
| 1 | 1.50431511 | CX527054 | AI498860. | NP_568578 | Unknown |
| 1 | 1.508595402 | AI498860. | | | Unknown |
| 1 | 1.526219104 | AC137701 | genomic clone bases 104725 106607 | | Unknown |
| 1 | 1.533385131 | TC103649 | | NP_201288 | unknown protein (Arabidopsis thaliana). |
| 1 | 1.564856352 | BI311172 | | ABE80976 | Yeast 73.5 kDa hypothetical-related protein |
| 1 | 1.595350872 | AL381833 | | NP_683304. | unknown protein (Arabidopsis thaliana) |
| 1 | 1.637723584 | TC102352 | | | Unknown protein |
| 1 | 1.645928157 | BG588732 | | | Unknown |
| 1 | 1.701040537 | TC94794 | | ABD32591 | conserved hypothetical protein (Medicago truncatula) |
| 1 | 1.730560109 | BI263622 | | BAD43289. | Unknown Protein |
| 1 | 1.781167825 | AC151666. | genomic clone bases 41495 40597 | ABE86457. | hypothetical protein like |
| 1 | 1.968633719 | TC111020 | | ABD32591 | conserved hypothetical protein (Medicago truncatula) |
| 1 | 2.123920941 | CB892051 | | AAM63790. | Unknown Protein |
| 1 | 2.948376671 | TC107896 | | NP_190741 | unknown protein (Arabidopsis thaliana). saposin B domain-containing protein eukaryotic aspartyl protease |
| 1 | 3.952930904 | AC132565 | genomic clone bases 77742 74206 | NP_198869 | Unknown Protein? |
| 1 | 4.726130066 | BF637940 | | BF637940 | Phsphate starved leaf library clone Mt. unkown |
| 1 | 5.719636462 | AC145330 | genomic clone bases 112146 110346 | ABE91561 | Protein of unknown function DUF341 (Medicago truncatula). |
| 1 | 17.51410973 | BG647066 | | Unknown | EST508685 HOGA Medicago truncatula cDNA clone pHOGA-15H19 5' end, RNA sequence |
| 1 | 56.1393086 | AC154034 | genomic clone bases 58483 61171 | NP_001055680 | Eukaryotic protein of unknown function (DUF914); |
| 2 | 1.57632892 | TC102174 | | NP_201474 | Zinc Finger Protein |
| 2 | 1.610893163 | AC146720 | ABE89629. | AC146720 | Zinc finger, GATA-type |
| 2 | 1.659262196 | TC105690 | | AAY30857. | MADS-box transcription factor (Prunus dulcis). Involved in flower development? |
| 2 | 1.707336474 | TC102175 | | NP_201474. | Zinc-Finger like protein Arabidopsis |
| 2 | 3.237013509 | AC149079 | genomic clone bases 98811 99796 | ABE83707.1 | transcription factor-like protein - Arabidopsis thaliana (Medicago truncatula). AP2 like may be involved with ethylene response |
| 2 | 5.277956696 | AL368418 | | ABE79293 | IQ calmodulin-binding region (Medicago truncatula). |
| 2 | 5.777555021 | TC105769 | | Q9ZUU0 | (Q9ZUU0) WRKY transcription factor 44 (WRKY DNA-binding protein 44) |

TABLE 3-continued

Genes induced by LAP1 expression.

| Fold Increase | TC/Gene | Medicago annotation | Link to homolog/est | Description |
|---|---|---|---|---|
| 2 | 6.086416289 | TC97762 | | AAS55706. | (TRANSPARENT TESTA GLABRA 2) WRKY2 [Nicotiana benthamiana]. Involvement of MEK1 MAPKK, NTF6 MAPK, WRKY/MYB transcription factors, COI1 and CTR1 in N-mediated resistance to tobacco mosaic virus Plant J. 38 (5), 800-809 (2004) |
| 2 | 15.32543616 | BI312112 | | AAM97321 | Homeodomain protein GhHOX1 involved with development? |
| 2 | 23.78314984 | BQ147051 | | AAN28286. | Myb like transcription factor similar to severa cotton Mybs but also to a Strawberry Myb that negatively regulates anthocyanin and flavanol accumulation |
| 2 | 37.40303349 | AC135317 | genomic clone bases 9174 16609 | AAG25927 | anthocyanin 1 (Petunia x hybrida). anthocyanin1 of petunia encodes a basic helix-loop-helix protein that directly activates transcription of structural anthocyanin genes Plant Cell 12 (9), 1619-1632 (2000) |
| 3 | 1.516857391 | TC101144 | | CAA93316 | nitrite transporter (Cucumis sativus). |
| 3 | 1.673305706 | CR932966 | | AAL05427 | Vacuolar acid invertase |
| 3 | 2.271546919 | BG450094 | | ABE85045. | ABC transporter, transmembrane region, type 1 (Medicago) |
| 3 | 2.302502449 | CB892086 | | AAF15946 | Cloning and expression of amino acid transporters from broad bean. Plant Mol. Biol. 41 (2), 259-268 (1999) |
| 3 | 2.516468468 | BE316901 | | NP_191829 | ATMRP10 [Arabidopsis thaliana]. ABC-type multidrug transport system, ATPase and permease components (Defense mechanisms) |
| 3 | 7.291492933 | BQ147947 | | NP_001053053 | Transmembrane amino acid transporter protein; pfam01490 Rice LeOPT1 (Lycopersicon esculentum). |
| 3 | 8.871794434 | BF639602 | | AAD01600 | Oligopeptide transporter? |
| 3 | 17.39794094 | CX540228 | | Q7XYX0 | Na+/H+ antiporter NHX6. Molecular characterization of Na+/H+ antiporters (ZmNHX) of maize (Zea mays L.) and their expression under salt stress J. Plant Physiol. 162 (1), 55-66 (2005) |
| 4 | 1.511489409 | TC109128 | | AAO22131 | quinone oxidoreductase 3 |
| 4 | 1.514604938 | TC688 | | AAY23356 | 3-ketoacyl-CoA reductase 3 (Gossypium hirsutum). |
| 4 | 1.5492671 | TC107174 | | Q6VAB3 | GT from Stevia making sweet glycosides UDP Glucosyltransferase |
| 4 | 1.561701368 | BI268054. | | | UDP-glycosyltransferase/transferase, |

TABLE 3-continued

Genes induced by LAP1 expression.

| Fold Increase | TC/Gene | Medicago annotation | Link to homolog/est | Description |
|---|---|---|---|---|
| 4 | 1.569246005 | BE322778 | | S39507 | transferring glycosyl groups glucuronosyl transferase homolog, ripening-related - tomato |
| 4 | 1.597672972 | U01020 | | U01020 | Medicago sativa clone MsCHS6-4 chalcone synthase |
| 4 | 1.61744966 | TC102229 | | gi|92892500|gb|ABE91274.1| | Anthocyanin acytransferase |
| 4 | 1.695040148 | AL381856 | | ABL74480 | Molecular cloning of Sweet potato (Ipomoea batatas L.) involved in anthocyanin production |
| 4 | 1.790778397 | TC102062 | | AAR13305 | phytochelatin synthetase-like protein (Phaseolus vulgaris) |
| 4 | 1.882478846 | TC105988 | | BAE72096 | Lactuca sativa short-chain dehydrogenase/reductase 1. Abscisic acid biosynthetic genes of lettuce |
| 4 | 1.934971944 | AC125473 | genomic clone bases 53689 57789 | ABE83980.1 | probable UDP-glucose, sterol glucosyltransferase |
| 4 | 2.012678128 | AC125473 | genomic clone bases 50127 52935 | ABE83979.1 | Glycosyl transferase, family 28 |
| 4 | 2.06856077 | AW684295 | | ABE90441 | Type III polyketide synthase (Medicago truncatula). Predicted naringenin-chalcone synthase |
| 4 | 2.091294444 | BE321766 | | Q9LZJ5 | Multidrug resistance-associated protein 10 (Glutathione S-conjugate-transporting ATPase 10) (ATP-energized glutathioneS-conjugate pump 10). |
| 4 | 2.117167571 | AC140035 | genomic clone bases 67938 67189 | Q9LZJ5 | Multidrug resistance-associated protein 10 (GlutathioneS-conjugate-transporting ATPase 10) (ATP-energized glutathioneS-conjugate pump 10). |
| 4 | 2.204715236 | BG450101 | | BAC78438. | cDNA cloning and expression of isoflavonoid-specific glucosyltransferase from Glycyrrhiza echinata cell-suspensioncultures Planta 218 (3), 456-459 (2004) |
| 4 | 2.957758028 | TC100292 | | BAC78656 | beta-primeverosidase [Camellia sinensis]. glycosyl hydrolase Cloning of beta-primeverosidase from tea leaves, a key enzyme in tea aroma formation Plant Physiol. 130 (4), 2164-2176 (2002) |
| 4 | 3.929191593 | TC100294 | | AAZ31067. | beta-glucosidase (Medicago sativa). Molecular analysis of the effect of thidiazuron on morphogenesis of the Medicago sativa callus |
| 4 | 4.09441353 | AC146789 | genomic clone bases 34320 32141 | P93149 | Cytochrome P450 93B1 (Licodione synthase) ((2S)-flavanone2-hydroxylase) (Flavone synthase II) |

TABLE 3-continued

Genes induced by LAP1 expression.

| Fold Increase | TC/Gene | Medicago annotation | Link to homolog/est | Description |
|---|---|---|---|---|
| 4.813343338 | AC146342 | genomic clone bases 5219 6819 | AAO22131 | (CYP GE-5). Two new cytochrome P450 cDNAs from elicitor-induced Licorice (*Glycyrrhiza echinata* L.) cells Zinc-containing alcohol dehydrogenase superfamily quinone oxidoreductase (*Fragaria* x *ananassa*). FaQR, Required for the Biosynthesis of the Strawberry Flavor Compound 4-Hydroxy-2,5-Dimethyl-3(2H)-Furanone, Encodes an Enone Oxidoreductase. Plant Cell 18 (4), 1023-1037 (2006) |
| 4.963582493 | TC108579 | | P31687 | 4-coumarate--CoA ligase (*Glycine max*). Molecular cloning and expression of 4-coumarate:coenzyme A ligase, an enzyme involved in the resistance response of soybean (*Glycine max* L.) against pathogen attack. Plant Physiol. 102 (4), 1147-1156 (1993) |
| 5.308798334 | AC146650 | genomic clone bases 79531 80861 | ABE90076 | Naringenin-chalcone synthase Type III polyketide synthase (*Medicago truncatula*). Chalcone and stilbene synthases; plant-specific polyketide synthases (PKS) and related enzymes, also called type III PKSs |
| 6.559801163 | TC101521 | | NP_194260 | iron ion binding/isopenicillin-N synthase/oxidoreductase oxidoreductase, 2OG-Fe(II) oxygenase family protein, similar to flavonol synthase (*Petunia* x *hybrida*)(GI: 311658), anthocyanidin synthase (*Torenia fournieri*)(GI: 12583673) |
| 6.598831576 | TC103465 | | AAR27015 | dihydroflavonal-4-reductase 2 (*Medicago truncatula*). |
| 7.348495446 | AC146575 | genomic clone bases 96668 95373 | ABE90441 | Naringenin-chalcone synthase Type III polyketide synthase (*Medicago truncatula*). |
| 9.76505364 | BI311259 | | ABE89970 | chalcone synthase 3 Type III polyketide synthase (*Medicago truncatula*). |
| 18.53831328 | AC146575 | genomic clone bases 92557 91179 | ABE90440. | Naringenin-chalcone synthase; Type III polyketide synthase |
| 19.59706853 | BF635325 | | AAD10774. | Cytochrome b5 DIF-FA cytochrome b5 is required for full activity of flavonoid 3',5'-hydroxylase, a cytochrome P450 involved in the |

TABLE 3-continued

Genes induced by LAP1 expression.

| | Fold Increase | TC/Gene | Medicago annotation | Link to homolog/est | Description |
|---|---|---|---|---|---|
| 4 | 22.09700291 | AC138453 | genomic clone bases 120053 122730 | ABE81099 | formation of blue flower colors. Proc. Natl. Acad. Sci. U.S.A. 96 (2), 778-783 (1999) 2OG-Fe(II) oxygenase (*Medicago truncatula*). Similar to Gibberellin and Flavanone hydroxylases |
| 4 | 29.89064908 | TC105632 | | BAE72453 | UDP-glucose: flavonol 3-O-glucosyltransferase (Rosa hybrid) Novel Anthocyanin Synthesis Pathway in Rosa hybrida Uses a Single Enzyme for Glucosyltransferase Activity at Two Sites |
| 4 | 32.00486522 | BI311113 | | AAR26526 | anthocyanidin synthase 2 (*Glycine max*). |
| 4 | 35.25649325 | CX526507 | | AAL07435 | Aphid infested shoots of *Medicago truncatula*; similar to Prunasin hydrolase A |
| 4 | 37.10455896 | AC146683 | genomic clone bases 54170 52902 | ABE89969 | Naringenin-chalcone synthase; Type III polyketide synthase |
| 4 | 40.12194709 | TC100057 | | ABE91274 | anthocyanin 5-aromatic acyltransferase/benzoyltransferase-like protein/anthocyanin acyltransferase-like protein-related [*Medicago* |
| 4 | 45.31027702 | AC147472 | genomic clone bases 118222 120283 | ABA42223 | Glutathione S-transferase, C-terminal; Thioredoxin-like fold Similar to Blood Orange GST |
| 4 | 46.05536469 | X80222 | | X80222 | *M. sativa* mRNA for dihydroflavonol-4-reductase |
| 4 | 64.32267886 | TC98548 | | ABE91274 | anthocyanin acyltransferase-like protein-related (*Medicago*) |
| 4 | 68.35044523 | AC146575 | genomic clone bases 82667 81204 | ABE90437 | Naringenin-chalcone synthase; Type III polyketide synthase |
| 4 | 81.68289535 | BM812824 | | AAR26526 | anthocyanidin synthase 2 [*Glycine max*]. |
| 4 | 96.28192087 | AC146683 | genomic clone bases 50180 48876 | P51082 | Chalcone synthase 1B (Naringenin-chalcone synthase 1B). |
| 4 | 100.8305355 | BQ147749 | | BAE71221 | Noble est BQ147749 Similar to putative flavonoid 3'-hydroxylase [Trifolium pratense]. |
| 4 | 109.6525563 | TC102034 | | Q6TQT1 | DFR-1 *Medicago truncatula* |
| 4 | 110.9283997 | BE248436 | | BAE71221 | putative flavonoid 3'-hydroxylase (Trifolium pratense). |
| 5 | 1.501179982 | TC109624 | | NP_001042139 | Putative receptor protein kinase |
| 5 | 1.518332136 | TC105110 | | NP_198442 | AMP binding/catalytic |
| 5 | 1.561081065 | TC98122 | | ABE82689 | Tyrosine protein kinase, active site [*Medicago truncatula* |

TABLE 3-continued

Genes induced by LAP1 expression.

| | Fold Increase | TC/Gene | Medicago annotation | Link to homolog/est | Description |
|---|---|---|---|---|---|
| 5 | 1.575299914 | CX529437 | | CX529437 | Latent Membrane Protein From Methyl Jasmonate elicted Roots cultures |
| 5 | 1.57717807 | AJ499132 | | Q9M011 | Light inducible protein |
| 5 | 1.586842934 | TC109710 | | AAR99376 | ring domain containing protein (*Capsicum annuum*). |
| 5 | 1.689120618 | BQ153446 | | AAN07898 | Xyloglucan endotransglycosylase |
| 5 | 1.692612124 | CB893247 | | NP_198442. | AMP binding/catalytic (*Arabidopsis thaliana*). |
| 5 | 1.729894042 | AJ499132 | | CAB82281. | light-inducible protein ATLS1 (*Arabidopsis thaliana*). |
| 5 | 1.756047217 | AC127018 | genomic clone bases 39514 34926 | ABE92051. | RNA-directed DNA polymerase (Reverse transcriptase); Polynucleotidyl transferase, Ribonuclease H fold [*Medicago truncatula*]. |
| 5 | 1.761465656 | TC97484 | | NP_567636. | TOM1 (TOBAMOVIRUS MULTIPLICATION 1) [*Arabidopsis thaliana*]. Transmembrane domain? |
| 5 | 1.766759229 | TC97483 | | BAE43836 | tobamovirus multiplication 1 [*Nicotiana tabacum*]. |
| 5 | 1.867177685 | BF651140 | | AAQ76706 | microtubule-associated protein 1 light chain 3 [*Gossypium hirsutum*]. GABA-receptor-associated protein) belongs ot a large family of proteins that mediate intracellular membrane trafficking and/or fusion |
| 5 | 1.894328458 | TC98046 | | NP 171993 | phosphoprotein phosphatase [*Arabidopsis thaliana*]. |
| 5 | 1.935798086 | AC 134049 | genomic clone bases 3231 1339 | ABE82689.1 | Tyrosine protein kinase, active site |
| 5 | 2.016545422 | AC142222 | genomic clone bases 28683 27870 | ABL97946 | copper ion binding/electron transporter [*Brassica rapa*]. Plastocyanin-like domain |
| 5 | 2.065367484 | BQ154698 | | ABE88271 | IMP dehydrogenase/GMP reductase [*Medicago truncatula*]. |
| 5 | 2.113493752 | AC146862 | genomic clone bases 18999 13099 | ABE91459 | Protein kinase; NAF [*Medicago truncatula*]. Serine/Threonine protein kinases, catalytic domain |
| 5 | 2.246515768 | TC109490 | | ABE88271 | IMP dehydrogenase/GMP reductase [*Medicago truncatula*]. |
| 5 | 2.347021892 | TC110695 | | NP 194589 | NPGR2 (NO POLLEN GERMINATION RELATED 2); calmodulin binding [*Arabidopsis thaliana*]. |
| 5 | 2.55133089 | AC149637 | | ABE88374 | Peptidase C1A, papain |
| 5 | 3.497575404 | CO516065 | est | CO516065 | Glandular trichome clone-ATP citrate lyase b-subunit [*Lupinus albus*]. |
| 5 | 3.980711007 | BF634212 | | Q9FXS7 | EIG-I24 protein TRANSFERASE. Characterizaton of Elicitor-inducible Tobacco Genes Isolated by Differential |

TABLE 3-continued

Genes induced by LAP1 expression.

| Fold Increase | TC/Gene | Medicago annotation | Link to homolog/est | Description |
|---|---|---|---|---|
| 4.144032233 | BQ147614 | | CAC24477 | Hybridization J. Gen Plant Pathol. 67:89-96 (2001). GTP binding protein. Characterisation of cDNAs homologous to Rab5-GTP binding protein expressed during early somatic embryogenesis in hickory Plant Sci. 163:413-422(2002) |
| 4.411209254 | TC112152 | | AAU14999 | MtN19-like protein Treatment of pea pods with Bruchin B results in up-regulation of a gene similar to MtN19 Plant Physiol. Biochem. 43 (3), 225-231 (2005) |
| 4.871792955 | TC525 | | ABE90151 | Cytochrome c oxidase assembly protein CtaG/Cox11, putative [Medicago truncatula]. |
| 4.959858613 | CX539005 | | ABE78861. | Leucine-rich repeats (LRRs), ribonuclease inhibitor Medicago, very weak similarity |
| 12.42467905 | AC146755 | genomic clone bases 64745 61928 | BAD13141 | ="myosin heavy chain-related-like |
| 17.41195083 | BQ147874 | | CAB77393. | Germin-like protein from Bean |
| 22.11465366 | AW736653 | | NP_850317 | Fructose-bisphosphate aldolase(7%)/unknown |
| 26.2220735 | AC127169 | genomic clone bases 95538 98294 | ABE83405 | Protein kinase [Medicago truncatula]. |

Example 6

Cloning and Expression of UGT78G1

The *M. truncatula* EST clone NF083F04ST (GT83F, corresponding to TIGR clone TC105632) was PCR amplified from pBluescript II SK+ (Stratagene, La Jolla, Calif., USA) with addition of BamHI and NotI sites (5'-C<u>GGATCC</u>ATGTCTACCTTCAAAAATG-3'; (SEQ ID NO:83), upstream primer; 5'-T<u>GCGGCCGC</u>ACTAGTGACAATTTG-3', downstream primer) (SEQ ID NO:84). The PCR product was purified, ligated to pGEMTeasy vector (Promega, Madison, Wis., USA), sequenced, excised and re-cloned between the BamHI and NotI sites of pET28a(+) (Novagen, Madison, Wis., USA) with a hexahistidine tag and a thrombin cleavage site. *E. coli* BL21 (DE3) cells harboring the expression construct were grown to an $OD_{600}$ of 0.4-0.5, and expression was initiated by addition of isopropyl 1-thio-β-D-galactopyranoside (IPTG) at a final concentration of 0.2 mM, with further incubation with shaking overnight at 16° C. The enzyme was purified from *E. coli* lysates by nickel affinity chromatography.

Example 7

Analysis of UGT78G1 Activity

Enzyme reactions were performed with 1-2.5 µg of enzyme in a total volume of 50 or 200 µl containing 50 mM Tris-HCl pH 7.0, 1.0-5.0 mM UDP-glucose, UDP-galactose or UDP-glucuronic acid, and 100-250 µM acceptor substrate at 30° C. Reactions were stopped with TCA and products analyzed by HPLC as described above.

For kinetic analysis of GT83F, purified enzyme (1.25 µg) was added to reaction mixtures (50 µl final volume) containing 50 mM Tris-HCl pH 7.0, 10 µM UDP-[U-$^{14}$C]-glucose (0.3 Ci/mmol), 490 µM UDP-glucose (unlabelled), and 0-500 µM acceptor substrate. Reactions were stopped with TCA after 15 min incubation at 30° C. Samples were extracted with 250 µl of ethyl acetate, and 200 µl were taken for liquid scintillation counting (Beckman LS6500). Data were analyzed using Hyper32 software for the analysis of enzyme-kinetic data (J. S. Easterby, University of Liverpool, Liverpool, UK; available at www.liv.ac.uk/~jse/software.html).

Example 8 qRT-PCR Experiments to Determine the Expression Pattern of UGT78G1

PCR primers (Table 5) were designed using Primer3 software (Rozen and Skaletsky, 2000; www.primer3.sourceforge.net/). Design criteria were Tm values of 60° C.±1° C., PCR amplicon lengths of 60 to 150 bp, and 18 to 24 nucleotide primers with GC content of 40% to 60%. Primer quality was checked using NetPrimer software (PREMIER Biosoft, Palo Alto, Calif.). The specificity of the primer pair sequences was checked against the *Medicago truncatula* transcript database using nucleotide-nucleotide BLAST (e.g. Altschul et al., 1990).

Total RNA was isolated from tissues or cultured cells using TRIreagent (Molecular Research Center, Inc, Cincinnati, Ohio, USA) according to the manufacturer's instructions. RNA samples were treated with TURBO DNA-free DNase I (Ambion) according to the manufacturer's instructions, and checked for genomic DNA contamination by PCR using the primers 5'-GTCCTCTAAGGTTTAATGAACCGG-3' (upstream) (SEQ ID NO:85) and 5'-GAAAGACACAGCCAAGTTGCAC-3' (downstream) (SEQ ID NO:86) designed to amplify an intron sequence of the *M. truncatula* ubiquitin gene (TC# 102473), and the primers 5'-ATTGCCTGCCCAAGAGTGTAAG-3' (upstream) (SEQ ID NO:87) and 5'-CAGCCAAGTTGCACAAAACAAC-3' (downstream) (SEQ ID NO:88) designed to amplify an intron/exon fragment of the same gene. RNA integrity was evaluated with an Agilent 2100 Bioanalyzer (Agilent, Santa Clara, Calif.) using RNA nano chips. RT reactions were done using the DNase I-treated RNAs and SuperScript III reverse transcriptase (Invitrogen), according to the manufacturer's instructions.

PCR reactions were performed in an optical 384-well plate with an ABI PRISM 7900 HT sequence detection system (Applied Biosystems, Foster City, Calif., USA), using SYBR Green to monitor dsDNA synthesis. Reactions contained 2.5 µl of SYBR Green Master Mix reagent (Applied Biosystems), 0.5 µl of cDNA, and 200 nM of each gene-specific primer in a final volume of 5 µl. PCR reactions were performed as described elsewhere (Czechowski et al, 2005). Data were analyzed using the SDS 2.2.1 software (Applied Biosystems). PCR efficiency (E) was estimated using the LinReg-PCR software (Ramakers et al, 2003) and the transcript levels were determined by relative quantification (Pfaffl, 2001) using the actin gene (TC# 107326) as a reference.

Example 9

Properties of UGT78G1

A. UGT78G1 Substrate Specificity and Products

Glucosyltransferase UGT78G1 (SEQ ID NO:10) was shown, in a preliminary screen, to exhibit activity with a wide range of flavonoid substrates (FIG. 9), and these compounds were therefore selected for in-depth kinetic analysis of substrate specificity. UGT78G1 displayed typical Michaelis-Menten kinetics for the various acceptor substrates FIG. 10, Table 4). A comparison of substrate structure-activity relationships revealed that the carbonyl group on ring C of the (iso)flavonoid acceptor is not critical, since the enzyme glycosylates anthocyanidins, which lack this group (Table 4). Substitution of the B-ring hydroxyl group at C4' with a methyl group increases the catalytic specificity ($K_{cat}/K_m$ ratio) for the substrate when no hydroxyl group is present at C5 of the A ring. Thus, UGT78G1 prefers formononetin to daidzein by about 2-fold. Although the $K_m$ values for biochanin A (4'-methoxy genistein) and genistein are different (11.7 and 36.7 µM, respectively), UGT78G1 exhibits similar overall specificity for these compounds under the experimental conditions used. Likewise, only slight differences in specificity were observed between genistein and daidzein, even though the $K_m$ for the former is 23-fold higher than for the latter.

TABLE 4
Kinetic parameters for UGT78G1 toward different (iso) flavonoids. * indicates the position of glycosylation.
| Substrate | V$_{max}$ (μmol/min) | K$_m$ (μM) | K$_{cat}$ (s$^{-1}$) | K$_{cat}$/K$_m$ (s$^{-1}$ M$^{-1}$) |
|---|---|---|---|---|
| 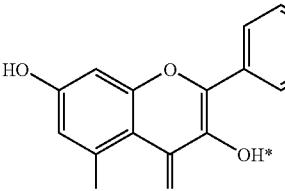 Kaempferol | 1.5830 | 89.8 | 5.3 × 10$^{-2}$ | 589.5 |
| 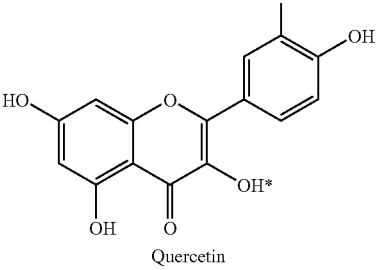 Quercetin | 0.8557 | 28.7 | 2.9 × 10$^{-2}$ | 997.0 |
| 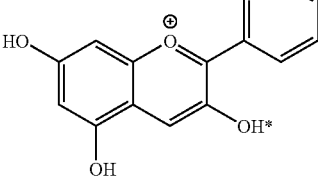 Pelargonidin | 0.2025 | 52.0 | 6.8 × 10$^{-3}$ | 130.2 |
| 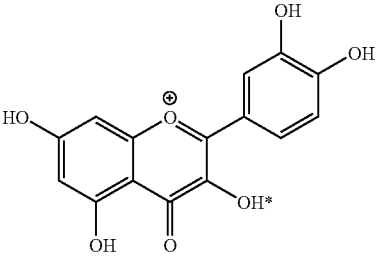 Cyanidin | 0.1698 | 71.8 | 5.7 × 10$^{-3}$ | 79.1 |
| 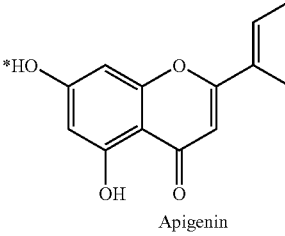 Apigenin | 0.0688 | 1.5 | 2.3 × 10$^{-3}$ | 1,534.2 |

TABLE 4-continued

Kinetic parameters for UGT78G1 toward different (iso) flavonoids. * indicates the position of glycosylation.

| Substrate | $V_{max}$ (μmol/min) | $K_m$ (μM) | $K_{cat}$ (s$^{-1}$) | $K_{cat}/K_m$ (s$^{-1}$ M$^{-1}$) |
|---|---|---|---|---|
| 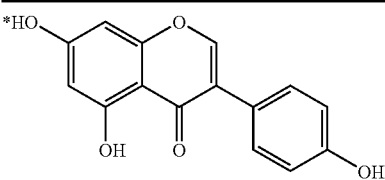 Genistein | 1.2050 | 36.7 | $4.0 \times 10^{-3}$ | 1,098.0 |
| 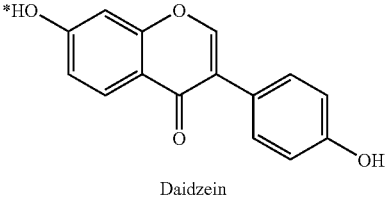 Daidzein | 0.0530 | 1.6 | $1.8 \times 10^{-3}$ | 1,107.7 |
| 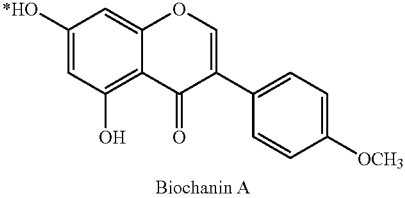 Biochanin A | 0.3666 | 11.7 | $1.2 \times 10^{-2}$ | 1,047.8 |
| 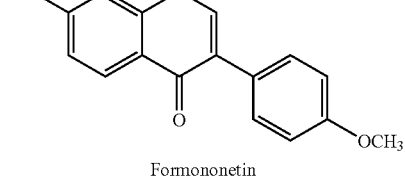 Formononetin | 0.0879 | 1.5 | $2.9 \times 10^{-3}$ | 1,959.8 |

The position of the aromatic B ring only slightly affects substrate binding/turnover (Table 4). Thus, the $K_{cat}/K_m$ ratio for apigenin (a flavone) is 1,534 whereas the $K_{cat}/K_m$ ratio is 1,098 for its corresponding isoflavone (genistein). UGT78G1 glycosylates apigenin, genistein, biochanin A, daidzein, and formononetin at the 7-O-position (Table 4). However, the $V_{max}$ of UGT78G1 for the flavonols kaempferol and quercetin, both of which have OH groups at C7 and C3, is much higher when compared with that for most of the other substrates, and the flavonols are glycosylated at the 3-position. However, anthocyanidins (cyanidin and pelargonidin), which also possess a 3-OH group, were relatively poor substrates for UGT78G1 in vitro. Nevertheless, UGT78G1 was the only enzyme, from among eight tested *Medicago* UGTs active with flavonoids, that could glycosylate anthocyanidins (data not shown).

B. Tissue-Specific Expression Patterns of *Medicago* UGT78G1

The in vitro substrate specificity of a UGT does not necessarily reflect the enzyme's in vivo function (Achnine et al., 2005). The strong induction of UGT78G1 as a result of ectopic expression of LAP1 in *M. truncatula* suggests that this particular UGT might be involved in anthocyanin glycosylation in vivo. To further address potential in vivo functions of UGT78G1, the expression pattern of this gene was evaluated by real time quantitative RT-PCR (qRT-PCR) using gene-specific primers (FIG. 11, Table 5). Stem, flower, root, leaf, and bud were the tissues examined, and root-derived cell suspension cultures also included in these analyses. Leaves were also wounded and inoculated with spores of the leaf spot pathogen *Phoma medicaginis*, a treatment that induces accumulation of isoflavonoid aglycones (He and Dixon, 2000; Deavours and Dixon, 2005). Cell suspension cultures were treated with yeast extract (YE), an inducer of isoflavonoid biosynthesis, or MeJA (methyl jasmonate), an inducer of triterpene saponin biosynthesis (Achnine et al., 2005; Suzuki et al., 2005).

TABLE 5

Primers used for the quantification of the transcript levels of *M truncatula* (iso)flavonoid glycosyltransferase genes by qRT-PCR. (SEQ ID NOs: 79-82).

| Gene | Primer |
|---|---|
| Actin (upstream) | 5'-TCAATGTGCCTGCCATGTATGT-3' |
| Actin (downstream) | 5'-ACTCACACCGTCACCAGAATCC-3' |

TABLE 5-continued

Primers used for the quantification of the transcript levels of M truncatula (iso)flavonoid glycosyltransferase genes by qRT-PCR. (SEQ ID NOs: 79-82).

| Gene | Primer |
|---|---|
| UGT78G1 (upstream) | 5'-GGCAGAGACAGGGAAGAACA-3' |
| UGT78G1 (downstream) | 5'-TAAATCCGCACCAAACCAA-3' |

UGT78G1 was expressed in all plant organs examined by qRT-PCR, but was most strongly expressed in buds. Its expression was strongly down-regulated by wounding of leaves, and also by application of MeJA to cell cultures. Expression in buds is consistent with involvement in anthocyanin synthesis.

Example 10

Production of Pas in Transgenic Alfalfa Co-Expressing LAP1 and ANR

Figure 12B:
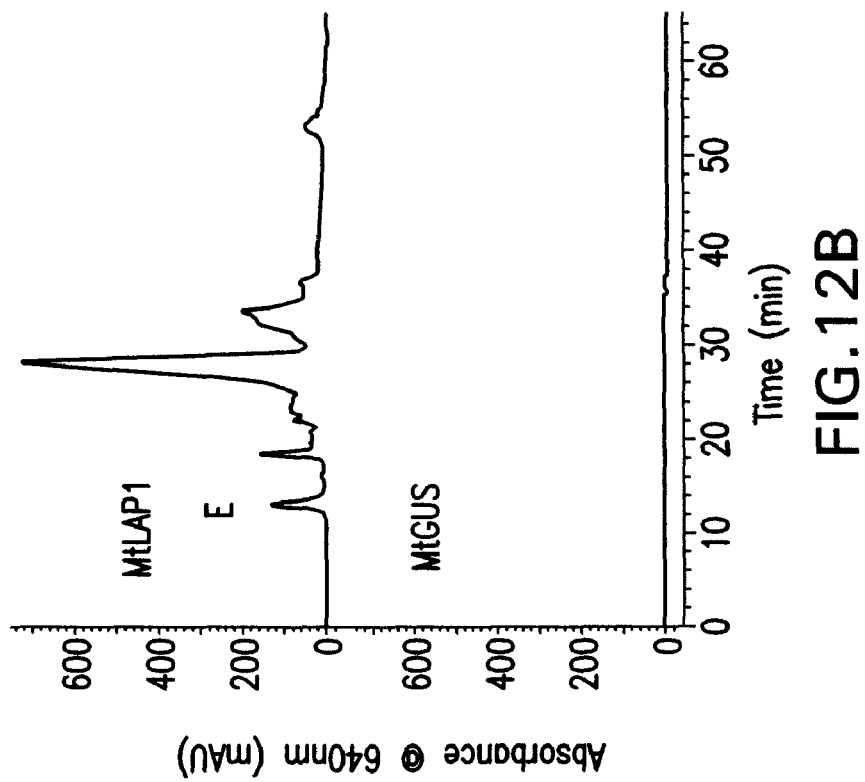
Figure 12A:
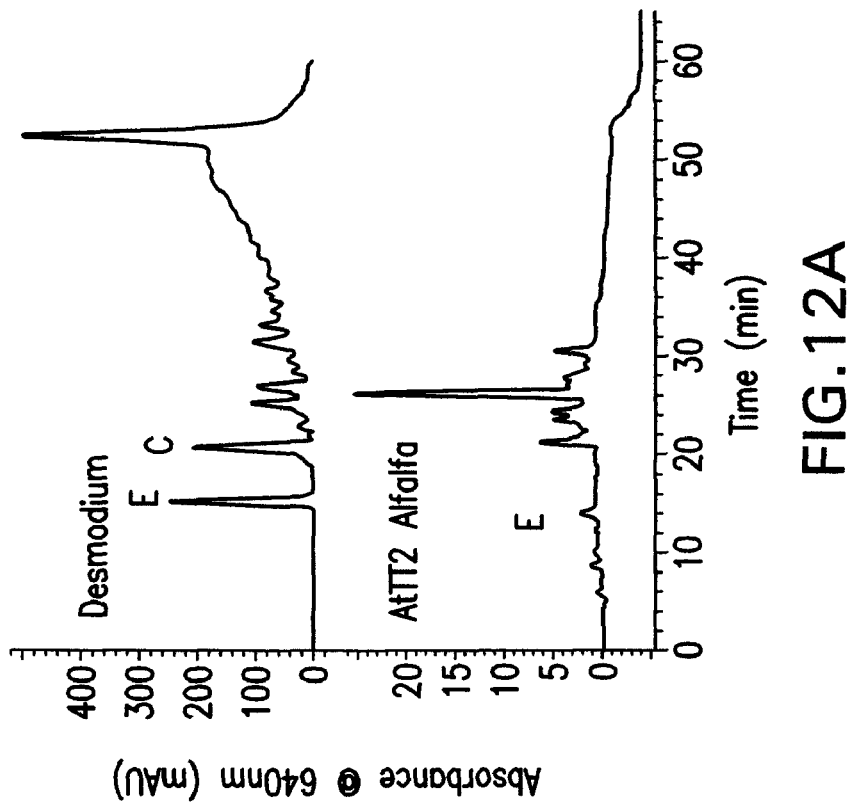

To identify PAs in the transgenic tissues, a modified post column reaction HPLC analysis was performed (e.g. Peel and Dixon, 2007). This protocol allows for the detection of monomeric as well as simple oligomeric PAs. When leaf extracts from the tannin-rich legume *Desmodium uncinatum* are run under these conditions, monomeric PA units (catechin and epicatechin) as well as various oligomers of increasing size are separated easily (FIG. 12A). Extracts from leaves of LAP 1-expressing *M. truncatula* plants were prepared with aqueous acidic acetone and analyzed in the same way for oligomeric PAs by normal phase HPLC followed by post-column derivatization with DMACA reagent (FIG. 12B). Control plants expressing GUS were analyzed in parallel, and shown to yield no detectable DMACA-positive material. In contrast, plants expressing MtLAP1 produced (−)-epicatechin and small amounts of oligomeric PAs. Since LAP1 expression did not increase expression of transcripts encoding ANR or LAR (FIG. 8), it is likely that the massively elevated pool of anthocyanins in MtLAP1-expressing plants simply leaks towards formation of epicatechin and oligomeric PAs through low basal levels of endogenous ANR and/or LAR activity.

Figure 12D:
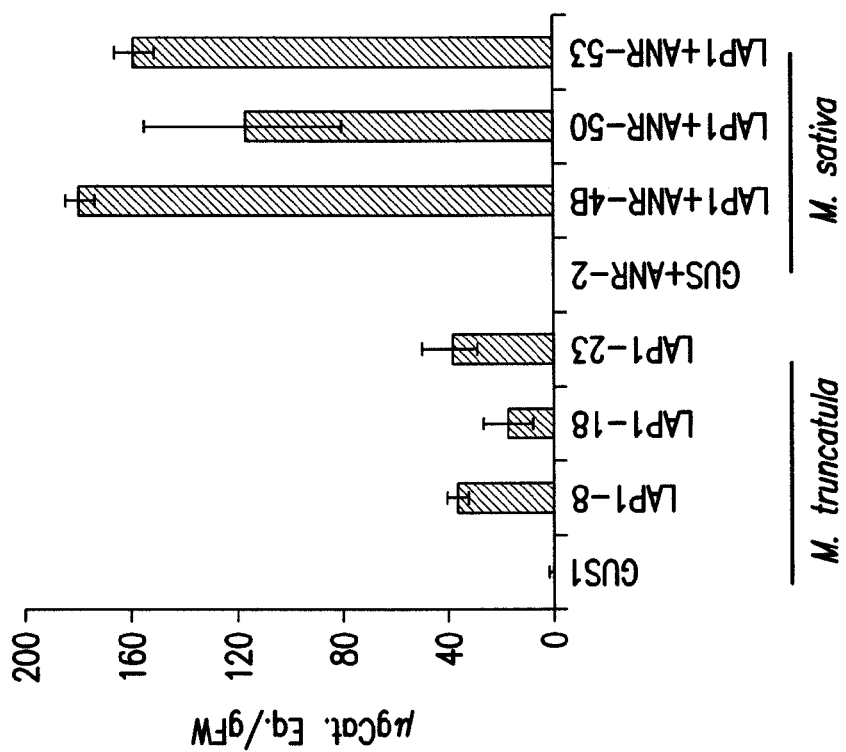
Figure 12C:
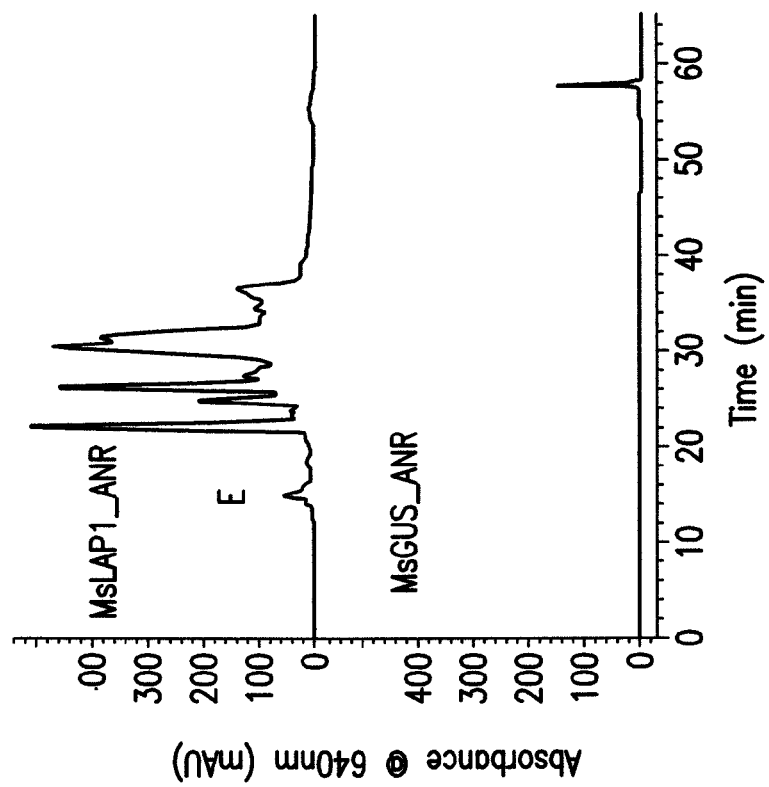

The above observation suggests that co-expression of ANR with MtLAP1 should lead to high levels of PA synthesis, as previously reported for co-expression of AtPAP1 and MtANR in tobacco (Xie et al., 2006). To test this hypothesis, leaves of transgenic alfalfa co-expressing MtLAP1 and MtANR were analyzed. It is already known that alfalfa foliage contains no detectable PA levels (Jackson and Barry, 1996), and this was confirmed by normal phase HPLC analysis of extracts from alfalfa plants co-expressing MtANR and GUS (FIG. 12C). Anthocyanidin supply is presumably limiting for PA production in such plants. However, in alfalfa plants co-expressing MtLAP1 and MtANR, small amounts of free epicatechin and catechin, plus significant levels of a range of oligomeric PAs, were observed (FIG. 12C). PA production was considerably higher than observed in *M. truncatula* plants expressing LAP1 alone (FIG. 12A). Overall levels of PAs in three independent lines of *M. truncatula* expressing LAP1, and alfalfa co-expressing LAP1 and MtANR, are shown in FIG. 12D. Importantly, the PA levels achieved in the alfalfa plants were within the range described as necessary for pasture bloat reduction (Li et al., 1996).

Example 11

Production of Insoluble Pas in Transgenic Alfalfa Co-Expressing LAP1 and ANR

Leaf extracts from transgenic alfalfa plants at 3 weeks after cut-back were analyzed for insoluble PA polymers using the butanol-HCl method described below.

For analysis of insoluble PAs, 0.5 g of ground samples were extracted with 5 ml of 70% acetone/0.5% acetic acid (extraction solution) by vortexing, and then sonicated at room temperature for 1 hour. Following centrifugation at 2,500 g for 10 min, the residues were re-extracted twice as above. The pooled supernatants were then extracted three times with chloroform and three times with hexane, and the supernatants (containing soluble PAs) and residues (containing insoluble PAs) from each sample were freeze dried separately. For quantification of insoluble PAs, 2 ml of butanol-HCl (95:5, v/v) reagent was added to the dried residues and the mixtures sonicated at room temperature for 1 h, followed by centrifugation at 2,500 g for 10 min. The absorption of the supernatants was measured at 550 nm; the samples were then boiled for 1 h, cooled to room temperature, and the absorbance at 550 nm recorded again, with the first value being subtracted from the second. Absorbance values were converted into PA equivalents using a standard curve of procyanidin B1 (Indofine, N.J., USA). Transgenic alfalfa plants co-expressing LAP1 and ANR produced at least four times more insoluble PAs than plants expressing LAP1 alone (FIG. 13). Control plants expressing GUS alone had very low levels of insoluble tannins.

Example 12

Effects of Ectopic Expression of *Arabidopsis* TT2 in Alfalfa

TT2 is a MYB transcription factor that controls the downstream, PA-specific branch of flavonoid biosynthesis in the *Arabidopsis* seed coat. Ectopic expression of AtTT2 in *Medicago truncatula* hairy roots leads to accumulation of PAs which when propagated normally accumulate large levels of anthocyanins. The same construct has been transformed into *Medicago sativa* plants, which do not accumulate significant levels of anthocyanins under normal conditions; however analysis of leaf tissues was able to show small amounts of oligomeric PA accumulation (FIG. 12A). Thus it appears that without an adequate supply of anthocyanidins, no accumulation of PAs can occur regardless of which downstream PA specific genes are expressed. It follows that co-expression of LAP1 and TT2 represents another strategy for introducing tannins to combat pasture bloat in alfalfa.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,518,584; U.S. Pat. No. 4,535,060; U.S. Pat. No. 4,554,101; U.S. Pat. No. 4,737,462; U.S. Pat. No. 5,302,523; U.S. Pat. No. 5,322,783; U.S. Pat. No. 5,384,253; U.S. Pat. No. 5,464,765; U.S. Pat. No. 5,508,184; U.S. Pat. No. 5,508,468; U.S. Pat. No. 5,538,877; U.S. Pat. No. 5,538,880; U.S. Pat. No. 5,545,818; U.S. Pat. No. 5,550,318; U.S. Pat. No. 5,563,055; U.S. Pat. No. 5,591,616; U.S. Pat. No. 5,610,042

U.S. Patent Publn. 2004/0191787; U.S. Patent Publn 2004/0093632; U.S. Patent Publn.

Abdullah et al., *Biotechnology*, 4:1087, 1986.
Achnine et al., *Plant J.*, 41:875-887, 2005.
Aerts et al., *Agri. Ecosys. Environ.*, 75:1-12, 1999.
Aharoni et al., *Plant J.*, 28:319-332, 2001.
Albrecht and Muck, *Crop Science*, 31:464-469, 1991.
Altschul et al., *J. Mol. Biol.*, 215:403-410, 1990.
Aziz et al., *Planta*, 221:28-38, 2005.
Bagchi et al., *Toxicology*, 148:187-197, 2000.
Barry and McNabb, *Brit. J. Nutrition*, 81:263-272, 1999.
Bates, *Mol. Biotechnol.*, 2(2):135-145, 1994.
Battraw and Hall, *Theor. App. Genet.*, 82(2):161-168, 1991.
Bending and Read, *Soil Biol. Biochem.*, 28:1603-1612, 1996.
Bevan et al., *Nucleic Acids Research*, 11(2):369-385, 1983.
Bhattacharjee et al., *J. Plant Bioch. and Biotech.*, 6, (2):69-73. 1997.
Borevitz et al., *Plant Cell*, 12:2383-2393, 2000.
Bouchez et al., *EMBO Journal*, 8(13):4197-4204, 1989.
Brevetti et al., *Ann. Oftalmol. Clin. Ocul.*, 115:109-116, 1989.
Buchanan-Wollaston et al., *Plant Cell Reports*, 11:627-631. 1992
Buising and Benbow, *Mol. Gen. Genet.*, 243(1):71-81. 1994.
Callis et al., *Genes Dev.*, 1:1183-1200, 1987.
Casa et al., *Proc. Natl. Acad. Sci. USA*, 90(23):11212-11216, 1993.
Chandler et al., *Plant Cell*, 1:1175-1183, 1989.
Christou; et al., *Proc. Natl. Acad. Sci. USA*, 84(12):3962-3966, 1987.
Chu et al., *Scientia Sinica*, 18:659-668, 1975.
Conkling et al., *Plant Physiol.*, 93:1203-1211, 1990.
DE 3642 829
De Block et al., *EMBO J.*, 6(9):2513-2518, 1987.
De Block et al., *Plant Physiol.*, 91:694-701, 1989.
Deavours and Dixon, *Plant Physiology*, 138:2245-2259, 2005.
Deavours et al., *Plant Molec. Biol.*, 62:715-733, 2006.
Debeaujon et al., *Plant Cell*, 13:853-871, 2001.
Dellaporta et al., In: *Chromosome Structure and Function: Impact of New Concepts*, 18th Stadler Genetics Symposium, 11:263-282, 1988.
Dellaporta et al., *Plant Mol. Biol. Rep.*, 1:19-21, 1983.
Deluc et al., *Plant Physiol.*, 140:499-511, 2006.
deMajnik et al., *Aust. J. Plant Physiol.*, 27:659-667, 2000.
D'Halluin et al., *Plant Cell*, 4(12):1495-1505, 1992.
Dixon et al., *New Phytologist*, 165:9-28, 2005.
Douglas et al., *NZ J. Agricultural Res.*, 42:55-64, 1999.
Dufresne and Farnworth, *J. Nutritional Biochem.*, 12:404-421, 2001.
Ebert et al., *Proc. Natl. Acad. Sci. USA*, 84:5745-5749, 1987.
Ellis et al., *EMBO J.*, 6(11):3203-3208, 1987.
European Patent Appln. 154,204.
Fire et al., *Nature*, 391(6669):806-811, 1998.
Foo and Porter, *Phytochemistry*, 19:1747-1754, 1980.
Foo et al., *Phytochemistry*, 54:173-81, 2000.
Fraley et al., *Bio/Technology*, 3:629-635, 1985.
Fromm et al., *Nature*, 319:791-793, 1986.
Gallie et al., *Plant Cell*, 1:301-311, 1989.
Gelvin et al., In: *Plant Molecular Biology Manual*, 1990.
Ghosh-Biswas et al., *J. Biotechnol.*, 32:1-10, 1994.
Gu et al., *J. Agric. Food Chem.*, 50:4852-4860, 2002.
Hall et al., *Canadian Veterinay J.*, 35:702-705, 1994.
Hamilton et al., *Proc. Natl. Acad. Sci. USA*, 93:9975-9979, 1996.
Haseloff et al., *Proc. Natl. Acad. Sci. USA*, 94:2122-2127, 1997.
He and Dixon, *Plant Cell*, 12:1689-1702, 2000.
He et al., *Plant Cell Reports*, 14 (2-3):192-196, 1994.
Hiei et al., *Plant. Mol. Biol.*, 35:205-218, 1997.
Hinchee et al., *Bio/technol.*, 6:915-922, 1988.
Horsch et al., *Science*, 227:1229-1231, 1985.
Hou and Lin, *Plant Physiology*, 111: 166, 1996.
Hudspeth and Grula, *Plant Mol. Biol.*, 12:579-589, 1989.
Ikuta et al., *Bio/technol.*, 8:241-242, 1990.
Ishidia et al., *Nat. Biotechnol.*, 14:745-750, 1996.
Jackson and Barry, *J. Sci. Food Agric.*, 71:103-110, 1996.
Kaeppler et al., *Plant Cell Reports* 9: 415-418, 1990.
Kaeppler, Somers, Rines, Cockburn, *Theor. Appl. Genet.*, 84:560-566, 1992.
Katz et al., *J. Gen. Microbiol.*, 129:2703-2714, 1983.
Kitamura et al., *Plant J.*, 37:104-114, 2004.
Klee et al., *Bio-Technology*, 3:637-642, 1985.
Knittel et al., *Plant Cell Reports*, 14(2-3):81-86, 1994.
Koupai-Abyazani et al., *J. Agri. Food Chem.*, 41:565-569, 1993.
Kyte and Doolittle, *J. Mol. Biol.*, 157:105 132, 1982.
Lawton et al., *Plant Mol. Biol.* 9:315-324, 1987.
Lazo et al., *Biotechnology.*, 9(10):963-967, 1991.
Lazzeri, *Methods Mol. Biol.*, 49:95-106, 1995.
Lee et al., *Brit. J. Nutr.*, 93:895-800, 2005.
Lee et al., *Korean J. Genet.*, 11:65-72, 1989.
Lees, *Basic Life Sci.*, 59:915-934, 1992.
Li et al., *J. Sci. Food Agric.*, 70:89-101, 1996.
Lin et al., *J. Nat. Prod.*, 65:505-8, 2002.
Liu et al., *Proc. Natl. Acad. Sci USA*, 99, 14578-14583, 2002.
Lorz et al., *Mol Gen Genet*, 199:178-182, 1985.
Marcotte et al, *Nature*, 335:454, 1988.
Martinez et al., *Cell*, 110:563-574, 2002.
Mathews et al., *Plant Cell*, 15:1689-1703, 2003.
McCabe and Martinell, *Bio-Technology*, 11(5):596-598, 1993.
McCormac et al., *Euphytica*, 99(1):17-25, 1998.
McKersie et al., *Plant Physiol.* 103:1155-1163, 1993.
McKhann and Hirsch, *Plant Mol Biol.* 24(5):767-77, 1994
McManus and Sharp, *Nat. Rev. Genet.* 3:737-47, 2002.
Modolo et al., *Plant Molec. Biol.* 64:499-518, 2007.
Morris and Robbins, In: *Biotechnology and the Improvement of Forage Legumes*, McKersie and Brown (Eds.), CAB International, Wallingford, Conn., 147-173, 1997.
Murakami et al., *Mol. Gen. Genet.*, 205:42-50, 1986.
Murashige and Skoog, *Physiol. Plant.*, 15:473-497, 1962.
Nagatani et al., *Biotech. Tech.*, 11(7):471-473, 1997.
Odell et al., *Nature*, 313:810-812, 1985.
Ogawa et al., *Sci. Rep.*, 13:42-48, 1973.

Omirulleh et al., *Plant Mol. Biol.*, 21(3):415-428, 1993.
Ow et al., *Science*, 234:856-859, 1986.
Pascual-Teresa et al., *J. Agric. Food Chem.*, 46:4209-4213, 1998.
Pataki et al., *Am. J. Clin. Nutr.*, 75:894-899, 2002.
PCT Appln. WO 06/010096
PCT Appln. WO 9217598
PCT Appln. WO 94/09699
PCT Appln. WO 95/06128
PCT Appln. WO 97/4103
PCT Appln. WO 97/41228
Peel and Dixon, *Natural Products Communications*, 2:1009-1014, 2007.
Peel et al., abstr. 1351 (P43006), presented at Botany & Plant Biology Joint Congress, Chicago, Ill., Jul. 8, 2007.
Porter, *Methods in Plant Biochemistry*, 1:389-419, 1989.
Potrykus et al., *Mol. Gen. Genet.*, 199:183-188, 1985.
Pourcel et al., *Plant Cell*, 17:2966-2980, 2005.
Prasher et al., *Biochem. Biophys. Res. Commun.*, 126(3):1259-1268, 1985.
Quattrocchio et al., *Plant Cell*, 11: 14433-1444, 1999.
Ramakers et al, *Neuroscience Letters* 339:62-66, 2003.
Ray et al., *Plant Physiol.*, 132:1448-1463, 2003.
Reddy et al., *Plant Physiol.*, 105:1059-1066, 1994.
Reed, *J. Animal Sci.*, 73:1516-1528, 1995.
Reichel et al., *Proc. Natl. Acad. Sci. USA*, 93 (12) p. 5888-5893. 1996.
Rhodes et al., *Methods Mol. Biol.*, 55:121-131, 1995.
Ritala et al., *Plant Mol. Biol.*, 24(2):317-325, 1994.
Rogers et al., *Methods Enzymol.*, 153:253-277, 1987.
Rozen and Skaletsky, In: *Bioinformatics methods and protocols: methods in molecular biology*, Krawetz and Misener (Eds.), Humana Press, NJ, 365-386, 2000.
Sambrook et al., In: *Molecular Cloning—A Laboratory Manual* (second edition), Cold Spring Harbour Laboratory Press, 1989.
Schemske et al., *Proc. Natl. Acad. Sci. USA*, 96:11910-11915, 1999.
Schultz and Baldwin, *Science*, 217:149-151, 1982.
Sharma and Dixon, *Plant J.*, 44:62-75, 2005.
Sheen et al., *Plant Journal*, 8(5):777-784, 1995.
Singsit et al., *Transgenic Res.*, 6(2):169-176, 1997.
Skadhauge et al., *Am. J. Bot.*, 84:494-502, 1997.
Spencer et al., *Plant Molecular Biology*, 18:201-210, 1992.
Stalker et al., *Science*, 242:419-422, 1988.
Sullivan et al., *Mol. Gen. Genet.*, 215(3):431-440, 1989.
Sutcliffe, *Proc. Natl. Acad. Sci. USA*, 75:3737-3741, 1978.
Suzuki et al., *Planta*, 220:698-707, 2005.
Tanner et al., *Austr. J. Agric. Res.*, 46:1101-1109, 1995.
Tanner et al., *J. Biol. Chem.*, 278:31647-31656, 2003.
Thillet et al., *J. Biol. Chem.*, 263:12500-12508, 1988.
Thomas et al., *Plant Sci.*, 69:189-198, 1990.
Thompson et al., *EMBO J.*, 6(9):2519-2523, 1987.
Tian et al., *Plant Cell Rep.*, 16:267-271, 1997.
Tingay et al., *Plant J.*, 11(6):1369-1376, 1997.
Tohge et al., *Plant J.*, 42:218-235, 2005.
Tomes et al., *Plant. Mol. Biol.* 14(2):261-268, 1990.
Toriyama et al., *Theor Appl. Genet.*, 73:16, 1986.
Treutter et al., *Acta Horticulturae*, 789-796, 1994.
Treutter, *J. Chromatography*, 467:185-193, 1989.
Tsukada et al., *Plant Cell Physiol.*, 30(4)599-604, 1989.
Twell et al., *Plant Physiol* 91:1270-1274, 1989.
Uchimiya et al., *Mol. Gen. Genet.*, 204:204, 1986.
Van Eck et al., *Plant Cell Reports*, 14(5):299-304, 1995.
Vasil et al., *Plant Physiol.*, 91:1575-1579, 1989.
Walder et al., *Gene*, 42:133, 1986.
Walker et al., *Proc. Natl. Acad. Sci. USA*, 84:6624-6628, 1987.
Wang et al., *Molecular and Cellular Biology*, 12(8):3399-3406, 1992.
Wright et al., In: *Agrobacterium Protocols*, Wang (Ed.), Humana Press, 343:129-136, 2006.
Xiao et al., *Molecular Breeding*, 15:221-231, 2005.
Xie and Dixon, *Phytochemistry*, 66:2126-2143, 2005.
Xie et al., *Plant J.*, 45:895-907, 2006.
Xie et al., *Science*, 299:396-399, 2003.
Yamada et al., *Plant Cell Rep.*, 4:85, 1986.
Yang and Russell, *Proc. Natl. Acad. Sci. USA*, 87:4144-4148, 1990.
Zheng and Edwards, *J. Gen. Virol.*, 71:1865-1868, 1990.
Zhou et al., *Plant Cell Reports*, 12(11).612-616, 1993.
Zukowsky et al., *Proc. Natl. Acad. Sci. USA*, 80:1101-1105, 1983.

What is claimed is:

1. An isolated nucleic acid sequence selected from the group consisting of:
    (a) a nucleic acid sequence encoding the polypeptide sequence of SEQ ID NO:5;
    (b) a nucleic acid sequence comprising SEQ ID NO: 1;
    (c) the full-length complement of a nucleic acid sequence that hybridizes to SEQ ID NO: 1, under stringent conditions of 0.02M NaCl and 70° C. and wherein said nucleic acid sequence encodes a polypeptide that activates anthocyanin or proanthocyanidin biosynthesis in a plant; and
    (d) a nucleic acid sequence encoding a polypeptide with at least 85% amino acid identity to SEQ ID NO:5, that activates anthocyanin or proanthocyanidin biosynthesis in a plant;
    (e) a nucleic acid sequence with at least 85% identity to SEQ ID NO: 1; and
    (f) a complement of a sequence of (a)-(e).

2. The isolated nucleic acid sequence of claim 1, wherein the nucleic acid sequence is operably linked to a heterologous promoter.

3. A recombinant vector comprising a nucleic acid sequence selected from the group consisting of:
    (a) a nucleic acid sequence encoding the polypeptide sequence of SEQ ID NO:5;
    (b) a nucleic acid sequence comprising SEQ ID NO: 1;
    (c) the full-length complement of a nucleic acid sequence that hybridizes to SEQ ID NO: 1, under stringent conditions of 0.02M NaCl and 70° C. and wherein said nucleic acid sequence encodes a polypeptide that activates anthocyanin or proanthocyanidin biosynthesis in a plant; and
    (d) a nucleic acid sequence encoding a polypeptide with at least 85% amino acid identity to SEQ ID NO:5, that activates anthocyanin or proanthocyanidin biosynthesis in a plant.

4. The recombinant vector of claim 3, further comprising at least one additional sequence chosen from the group consisting of a regulatory sequence, a selectable marker, a leader sequence and a terminator.

5. The recombinant vector of claim 4, wherein the additional sequence is a heterologous sequence.

6. The recombinant vector of claim 3, wherein the promoter is a plant developmentally-regulated, organelle-specific, inducible, tissue-specific, constitutive, or cell-specific promoter.

7. The recombinant vector of claim 3, defined as an isolated expression cassette.

8. A transgenic plant transformed with the recombinant vector of claim 3.

9. The transgenic plant of claim 8, wherein the plant is a *Medicago* plant.

10. The transgenic *Medicago* plant of claim 9, wherein the plant expresses the recombinant vector and exhibits increased proanthocyanidin biosynthesis in selected tissues of the transgenic *Medicago* plant relative to those tissues in a second non-transgenic *Medicago* plant that differs from the transgenic plant only in that the recombinant vector is absent.

11. The transgenic plant of claim 8, further defined as transformed with the recombinant vector comprising a nucleic acid sequence encoding a LAP1 polypeptide comprising SEQ ID NO:5 and having anthocyanin or proanthocyanidin biosynthesis activity when expressed in said transgenic plant.

12. The transgenic plant of claim 8, further defined as transformed with the recombinant vector comprising a nucleic acid sequence encoding the polypeptide of SEQ ID NO: 5.

13. The transgenic plant of claim 8, further defined as a forage crop.

14. The transgenic plant of claim 13, wherein the plant is a forage legume.

15. The transgenic plant of claim 14, wherein the forage legume is alfalfa (*Medicago sativa*).

16. The transgenic plant of claim 8, further defined as a fertile R0 transgenic plant.

17. The transgenic plant of claim 8, further defined as a progeny plant of any generation of a fertile R0 transgenic plant, wherein the progeny plant comprises the recombinant vector.

18. A transgenic seed of the transgenic plant of claim 8, transformed with the recombinant vector.

19. A cell transformed with the isolated nucleic acid of claim 1.

* * * * *

UNITED STATES PATENT AND TRADEMARK OFFICE
CERTIFICATE OF CORRECTION

PATENT NO. : 7,880,059 B2  Page 1 of 1
APPLICATION NO. : 12/108332
DATED : February 1, 2011
INVENTOR(S) : Dixon et al.

It is certified that error appears in the above-identified patent and that said Letters Patent is hereby corrected as shown below:

In claim 1, column 167, line 64, delete "(e) a nucleic acid sequence with at least 85% identity to SEQ ID NO: 1; and (f) a complement of a sequence of (a)-(e)".

Signed and Sealed this
Fourth Day of October, 2011

David J. Kappos
*Director of the United States Patent and Trademark Office*